(12) United States Patent
Wisniewski et al.

(10) Patent No.: US 11,969,033 B2
(45) Date of Patent: Apr. 30, 2024

(54) METHODS AND DEVICES TO REDUCE DAMAGING EFFECTS OF CONCUSSIVE OR BLAST FORCES ON A SUBJECT

(71) Applicant: Q30 SPORTS SCIENCE, LLC, Westport, CT (US)

(72) Inventors: Daniel Francis Wisniewski, Columbus, OH (US); Sherry Lynn Jones, Pataskala, OH (US); James Huang Lua, Columbus, OH (US); Kevin John Vititoe, Westerville, OH (US); Joseph M. Lehman, New Albany, OH (US); Jamison Joseph Float, Lewis Center, OH (US)

(73) Assignee: Q30 SPORTS SCIENCE, LLC, Westport, CT (US)

( * ) Notice: Subject to any disclaimer, the term of this patent is extended or adjusted under 35 U.S.C. 154(b) by 0 days.

(21) Appl. No.: 16/114,831

(22) Filed: Aug. 28, 2018

(65) Prior Publication Data

US 2019/0297966 A1 Oct. 3, 2019

Related U.S. Application Data

(63) Continuation of application No. PCT/US2017/020445, filed on Mar. 2, 2017.

(60) Provisional application No. 62/302,509, filed on Mar. 2, 2016.

(51) Int. Cl.
| | | |
|---|---|---|
| *A41D 13/05* | (2006.01) | |
| *A61B 17/132* | (2006.01) | |
| *A61F 13/12* | (2006.01) | |
| *A61B 90/00* | (2016.01) | |

(52) U.S. Cl.
CPC ........ *A41D 13/0512* (2013.01); *A61B 17/132* (2013.01); *A61B 17/1325* (2013.01); *A61F 13/128* (2013.01); *A61B 2090/065* (2016.02); *A63B 2225/62* (2013.01)

(58) Field of Classification Search
CPC .............. A41D 13/0512; A61B 17/132; A61B 17/1325; A61F 5/30; A61F 13/128
USPC ............................................ 2/468; 606/201
See application file for complete search history.

(56) References Cited

U.S. PATENT DOCUMENTS

| | | | |
|---|---|---|---|
| 428,926 A | 5/1890 | Martin | |
| 519,894 A | 5/1894 | Schutz et al. | |
| 1,123,873 A | 1/1915 | Heflin | |
| 1,280,742 A | 10/1918 | Hurd | |
| 1,473,041 A | 11/1923 | Henderson | |

(Continued)

FOREIGN PATENT DOCUMENTS

| | | | |
|---|---|---|---|
| CA | 2823184 | 9/2015 | |
| CA | 3005557 A1 * | 5/2017 | ......... A61B 17/1355 |

(Continued)

OTHER PUBLICATIONS

EP, 17760816.3 Extended Search Report, dated Oct. 29, 2019.

(Continued)

*Primary Examiner* — Alissa L Hoey
(74) *Attorney, Agent, or Firm* — Ruggiero, McAllister & McMahon LLC

(57) ABSTRACT

The disclosure provides systems, devices, and associated methods for mitigating traumatic brain injury, injury to an ocular structure, or injury to the inner ear of a subject by applying pressure to one or more neck veins before and during an injurious event.

13 Claims, 40 Drawing Sheets

(56) References Cited

U.S. PATENT DOCUMENTS

| | | | |
|---|---|---|---|
| 1,481,354 A | 1/1924 | Dingfeld | |
| 1,592,496 A | 7/1926 | Madden | |
| 1,691,856 A | 11/1928 | Robbins Maurice | |
| 2,091,276 A | 8/1937 | Gilbert | |
| 2,234,921 A | 3/1941 | Webb | |
| 2,271,927 A | 2/1942 | Saighman | |
| 2,284,205 A | 5/1942 | Hansen | |
| 2,320,183 A | 5/1943 | Martin | |
| 2,385,638 A | 9/1945 | Norwood | |
| 2,676,586 A | 4/1954 | Coakwell, Jr. | |
| 2,715,994 A | 8/1955 | Steinacker | |
| 3,008,464 A | 11/1961 | Atkins | |
| 3,078,844 A | 2/1963 | Scholz | |
| 3,171,409 A | 3/1965 | Cetrone | |
| 3,477,425 A | 11/1969 | Grassl | |
| 3,490,448 A | 1/1970 | Grubb | |
| 3,497,872 A * | 3/1970 | Mitchell | A63B 71/10 2/468 |
| 3,500,472 A | 3/1970 | Castellani | |
| 3,595,225 A | 7/1971 | Beeman | |
| 3,628,536 A | 12/1971 | Glesne | |
| 3,657,739 A * | 4/1972 | Holmes, Sr. | A41D 13/0512 2/468 |
| 3,765,412 A | 10/1973 | Ommaya et al. | |
| 3,832,105 A | 8/1974 | Takahashi | |
| 3,850,164 A | 11/1974 | Hare | |
| 3,901,230 A | 8/1975 | Henkin | |
| 3,945,042 A | 3/1976 | Lobo | |
| 4,121,582 A | 10/1978 | Remiro | |
| 4,159,020 A | 6/1979 | von Soiron et al. | |
| 4,188,946 A | 2/1980 | Watson et al. | |
| 4,204,547 A | 5/1980 | Allocca | |
| 4,243,028 A | 1/1981 | Puyana | |
| 4,272,011 A | 6/1981 | Nagatomo et al. | |
| 4,336,807 A | 6/1982 | Benckhuijsen | |
| 4,343,303 A * | 8/1982 | Williams | A61H 23/02 601/39 |
| 4,377,159 A | 3/1983 | Hansen | |
| 4,479,495 A | 10/1984 | Isaacson | |
| 4,549,998 A | 10/1985 | Porter et al. | |
| 4,576,150 A | 3/1986 | Auracher | |
| 4,628,926 A | 12/1986 | Duncan et al. | |
| 4,646,728 A | 3/1987 | Takeda | |
| 4,716,898 A | 1/1988 | Chauve et al. | |
| 4,817,595 A | 4/1989 | Maass | |
| 4,991,576 A | 2/1991 | Henkin et al. | |
| 4,997,438 A | 3/1991 | Nipper | |
| 5,078,728 A | 1/1992 | Giarratano | |
| 5,152,302 A | 10/1992 | Fareed | |
| 5,234,459 A | 8/1993 | Lee | |
| 5,255,675 A | 10/1993 | Kolobow | |
| 5,295,949 A * | 3/1994 | Hathaway | A61F 5/055 482/10 |
| 5,295,996 A | 3/1994 | Blair | |
| 5,302,806 A | 4/1994 | Simmons et al. | |
| 5,312,350 A | 5/1994 | Jacobs | |
| 5,320,093 A | 6/1994 | Raemer | |
| 5,338,290 A | 8/1994 | Aboud | |
| 5,375,261 A | 12/1994 | Lipke | |
| 5,381,558 A | 1/1995 | Lo | |
| 5,398,675 A | 3/1995 | Henkin et al. | |
| 5,403,266 A | 4/1995 | Bragg et al. | |
| 5,413,582 A | 5/1995 | Eaton | |
| 5,497,767 A | 3/1996 | Olsson et al. | |
| 5,501,697 A | 3/1996 | Fisher | |
| 5,507,280 A | 4/1996 | Henkin et al. | |
| 5,507,721 A | 4/1996 | Shippert | |
| D369,660 S | 5/1996 | Myoga | |
| 5,582,585 A | 12/1996 | Nash-Morgan | |
| 5,584,853 A | 12/1996 | McEwen | |
| 5,601,598 A | 2/1997 | Fisher | |
| 5,643,315 A | 7/1997 | Daneshvar | |
| 5,695,520 A * | 12/1997 | Bruckner | A61B 17/1325 606/201 |
| 5,709,647 A | 1/1998 | Ferber | |
| 5,752,927 A | 5/1998 | Rogachevsky | |
| 5,776,123 A | 7/1998 | Goerg et al. | |
| 5,792,176 A | 8/1998 | Chang | |
| 5,806,093 A | 9/1998 | Summers | |
| 5,817,218 A | 10/1998 | Hayashi et al. | |
| 5,848,981 A | 12/1998 | Herbranson | |
| 5,940,888 A | 8/1999 | Sher | |
| 5,957,128 A | 9/1999 | Hecker et al. | |
| 5,978,965 A | 11/1999 | Summers | |
| 6,007,503 A | 12/1999 | Berger et al. | |
| D419,267 S | 1/2000 | Hartunian | |
| 6,038,701 A | 3/2000 | Regan | |
| 6,058,517 A * | 5/2000 | Hartunian | A41D 13/0512 2/468 |
| 6,158,434 A | 12/2000 | Lugtigheid et al. | |
| 6,165,105 A | 12/2000 | Boutellier et al. | |
| 6,217,601 B1 * | 4/2001 | Chao | A61B 17/1325 606/203 |
| 6,227,196 B1 | 5/2001 | Jaffe et al. | |
| 6,238,413 B1 | 5/2001 | Wexler | |
| 6,245,024 B1 | 6/2001 | Montagnino et al. | |
| 6,274,786 B1 | 8/2001 | Heller | |
| 6,344,021 B1 | 2/2002 | Juster et al. | |
| 6,354,292 B1 | 3/2002 | Fisher | |
| 6,398,749 B1 | 6/2002 | Slautterback | |
| 6,423,020 B1 | 7/2002 | Koledin | |
| 6,554,787 B1 | 4/2003 | Griffin et al. | |
| D475,139 S | 5/2003 | Myoga | |
| 6,558,407 B1 | 5/2003 | Ivanko et al. | |
| 6,612,308 B2 | 9/2003 | Fisher et al. | |
| 6,622,725 B1 | 9/2003 | Fisher et al. | |
| 6,623,835 B2 | 9/2003 | Chang | |
| 6,655,382 B1 | 12/2003 | Kolobow | |
| 6,659,689 B1 | 12/2003 | Courtney et al. | |
| 6,663,653 B2 | 12/2003 | Akerfeldt | |
| 6,700,031 B1 | 3/2004 | Hahn | |
| 6,711,750 B1 * | 3/2004 | Yoo | A61F 7/02 2/338 |
| 6,766,570 B1 | 7/2004 | Klemm et al. | |
| 6,799,470 B2 | 10/2004 | Harada | |
| 6,799,570 B2 | 10/2004 | Fisher et al. | |
| 6,802,814 B2 | 10/2004 | Narimatsu | |
| 6,854,134 B2 | 2/2005 | Cleveland | |
| 7,069,598 B2 | 7/2006 | Welch | |
| 7,100,251 B2 | 9/2006 | Howell | |
| 7,100,606 B2 | 9/2006 | Fisher et al. | |
| 7,141,031 B2 | 11/2006 | Garth et al. | |
| D539,425 S | 3/2007 | Harrison | |
| 7,207,953 B1 | 4/2007 | Goicaj | |
| D555,836 S | 11/2007 | Foust et al. | |
| 7,452,339 B2 | 11/2008 | Mattison | |
| 7,618,386 B2 | 11/2009 | Nordt, III et al. | |
| 7,653,948 B2 | 2/2010 | Schwenner | |
| 7,981,135 B2 | 7/2011 | Thorpe | |
| D653,018 S | 1/2012 | Webbe et al. | |
| 8,109,963 B1 | 2/2012 | Korrol | |
| 8,376,975 B1 * | 2/2013 | Harris, Jr. | A61F 5/0104 602/17 |
| 8,381,362 B2 | 2/2013 | Hammerslag et al. | |
| 8,900,169 B2 | 12/2014 | Smith et al. | |
| 8,955,165 B1 | 2/2015 | Romero | |
| 8,985,120 B2 | 3/2015 | Smith | |
| 9,168,045 B2 * | 10/2015 | Smith | A41D 13/0512 |
| 9,173,660 B2 | 11/2015 | Smith et al. | |
| D763,518 S | 8/2016 | Fletcher et al. | |
| 9,913,501 B1 * | 3/2018 | Flug | A41D 31/285 |
| 10,905,180 B1 * | 2/2021 | Minaev | A41D 13/0512 |
| 11,452,322 B2 * | 9/2022 | Elvira | A61B 17/1325 |
| 2002/0004948 A1 | 1/2002 | Son | |
| 2003/0130690 A1 | 7/2003 | Porrata et al. | |
| 2003/0221554 A1 | 12/2003 | TeGrotenhuis et al. | |
| 2004/0127937 A1 | 7/2004 | Newton | |
| 2004/0128744 A1 | 7/2004 | Cleveland | |
| 2004/0243044 A1 * | 12/2004 | Penegor | A61B 17/0057 602/48 |
| 2004/0267178 A1 * | 12/2004 | Benckendorff | A61F 5/055 602/18 |
| 2005/0131322 A1 | 6/2005 | Harris, Jr. et al. | |

(56) References Cited

U.S. PATENT DOCUMENTS

| | | |
|---|---|---|
| 2005/0262618 A1 | 12/2005 | Musal |
| 2006/0015048 A1 | 1/2006 | Pillai |
| 2006/0122550 A1 | 1/2006 | Weaver |
| 2006/0048293 A1 | 3/2006 | Lewis et al. |
| 2006/0095072 A1 | 5/2006 | TenBrink |
| 2006/0108215 A1 | 5/2006 | Tzedakis et al. |
| 2006/0142675 A1* | 6/2006 | Sargent .................. A61H 39/04 601/134 |
| 2006/0200195 A1 | 9/2006 | Yang |
| 2007/0033696 A1 | 2/2007 | Sellier |
| 2007/0060949 A1 | 3/2007 | Curry |
| 2007/0123796 A1 | 5/2007 | Lenhardt et al. |
| 2007/0260167 A1 | 11/2007 | Heart |
| 2007/0287806 A1 | 12/2007 | Ong et al. |
| 2008/0021498 A1 | 1/2008 | Di Lustro |
| 2008/0038115 A1 | 2/2008 | Burns et al. |
| 2008/0071202 A1 | 3/2008 | Nardi et al. |
| 2008/0132820 A1 | 6/2008 | Buckman et al. |
| 2008/0154140 A1 | 6/2008 | Chang et al. |
| 2008/0200853 A1 | 8/2008 | Tielve |
| 2008/0267843 A1 | 10/2008 | Burns et al. |
| 2008/0319473 A1* | 12/2008 | Rosenbaum ....... A61B 17/1325 606/201 |
| 2009/0076421 A1 | 3/2009 | Grant, Jr. |
| 2009/0099496 A1 | 4/2009 | Heegaard |
| 2009/0105625 A1 | 4/2009 | Kohner et al. |
| 2009/0131973 A1 | 5/2009 | Zacharias |
| 2009/0143706 A1 | 6/2009 | Acosta |
| 2009/0173340 A1* | 7/2009 | Lee ...................... A61F 5/0193 128/106.1 |
| 2009/0192423 A1* | 7/2009 | Halmos ................. A61H 11/00 601/134 |
| 2009/0209925 A1 | 8/2009 | Marinello et al. |
| 2009/0234261 A1 | 9/2009 | Singh |
| 2009/0299242 A1* | 12/2009 | Hasegawa ............... A61F 5/055 602/18 |
| 2010/0000548 A1 | 1/2010 | Haworth et al. |
| 2010/0042138 A1* | 2/2010 | Duelo Riu ............ A61H 7/006 606/204 |
| 2010/0071169 A1 | 3/2010 | Williams et al. |
| 2010/0088808 A1 | 4/2010 | Rietdyk et al. |
| 2010/0122404 A1 | 5/2010 | Bowlus et al. |
| 2010/0137768 A1 | 6/2010 | Thorgilsdottir et al. |
| 2010/0139671 A1 | 6/2010 | Tull et al. |
| 2010/0152771 A1 | 6/2010 | Di Lustro |
| 2010/0179586 A1 | 7/2010 | Ward et al. |
| 2010/0204628 A1 | 8/2010 | Ghajar |
| 2010/0294284 A1 | 11/2010 | Hohenhorst et al. |
| 2010/0318114 A1 | 12/2010 | Pranevicius et al. |
| 2011/0010829 A1 | 1/2011 | Norman |
| 2011/0026934 A1 | 2/2011 | Boyd |
| 2011/0028934 A1* | 2/2011 | Buckman ............ A61B 17/135 604/385.12 |
| 2011/0040265 A1 | 2/2011 | Lu et al. |
| 2011/0065637 A1 | 3/2011 | Smith |
| 2011/0093003 A1 | 4/2011 | Lee |
| 2011/0107492 A1 | 5/2011 | Hinchey et al. |
| 2011/0257571 A1 | 10/2011 | Fritsch et al. |
| 2011/0270299 A1 | 11/2011 | Rose et al. |
| 2011/0295174 A1 | 12/2011 | Richards |
| 2011/0295311 A1 | 12/2011 | Adelman |
| 2012/0078157 A1 | 3/2012 | Ravikumar et al. |
| 2012/0197290 A1 | 8/2012 | Smith et al. |
| 2012/0246974 A1 | 10/2012 | Hammerslag et al. |
| 2012/0291189 A1 | 11/2012 | Chambers et al. |
| 2013/0041303 A1 | 2/2013 | Hopman et al. |
| 2013/0055492 A1* | 3/2013 | Husain ............. A42B 3/0473 2/468 |
| 2013/0085426 A1 | 4/2013 | Brodsky |
| 2013/0133648 A1 | 5/2013 | Beach et al. |
| 2013/0146066 A1 | 6/2013 | Croll |
| 2013/0167846 A1 | 7/2013 | Hurley |
| 2013/0239310 A1* | 9/2013 | Flug .................. A41D 13/0512 2/468 |
| 2013/0274638 A1 | 10/2013 | Jennings et al. |
| 2013/0304111 A1 | 11/2013 | Zhadkevich |
| 2013/0333708 A1 | 12/2013 | Hassan |
| 2014/0031781 A1 | 1/2014 | Razon-Domingo |
| 2014/0031787 A1 | 1/2014 | Burnes et al. |
| 2014/0142616 A1* | 5/2014 | Smith ................. A61B 17/1325 606/202 |
| 2014/0166024 A1 | 6/2014 | Davidson et al. |
| 2014/0236221 A1* | 8/2014 | Zhadkevich ........ A61B 17/1325 606/202 |
| 2014/0276278 A1* | 9/2014 | Smith ................... A61B 17/135 601/133 |
| 2014/0277101 A1* | 9/2014 | Smith ................. A61B 17/1325 606/202 |
| 2014/0343599 A1 | 11/2014 | Smith et al. |
| 2015/0190599 A1 | 7/2015 | Colman et al. |
| 2015/0305751 A1 | 10/2015 | Hoff et al. |
| 2015/0313607 A1 | 11/2015 | Zhadkevich |
| 2016/0044981 A1 | 2/2016 | Frank et al. |
| 2016/0045203 A1* | 2/2016 | Pollock ................ A61B 17/132 606/204 |
| 2016/0169630 A1 | 6/2016 | Augustine et al. |
| 2016/0213381 A1* | 7/2016 | Zhadkevich ........ A61B 17/1355 |
| 2016/0317160 A1* | 11/2016 | Smith .................. A61B 17/135 |
| 2017/0215769 A1 | 8/2017 | Lu et al. |
| 2017/0215795 A1 | 8/2017 | Ahmad et al. |
| 2018/0085247 A1 | 3/2018 | Trainor et al. |
| 2018/0263841 A1 | 9/2018 | Satake |
| 2018/0325194 A1* | 11/2018 | Elvira ...................... A61F 5/32 |
| 2018/0333159 A1 | 11/2018 | Smith |
| 2020/0266207 A1 | 8/2020 | Liu |
| 2020/0330323 A1* | 10/2020 | Jolly ...................... A61H 1/00 |
| 2021/0182856 A1 | 6/2021 | Kuchenski et al. |
| 2021/0223580 A1 | 7/2021 | Xu |
| 2021/0254179 A1 | 8/2021 | Xu et al. |

FOREIGN PATENT DOCUMENTS

| | | |
|---|---|---|
| CN | 87103201 | 12/1987 |
| CN | 201189186 Y | 2/2009 |
| CN | 101690658 | 7/2011 |
| CN | 102326890 | 1/2012 |
| CN | 202618320 U | 12/2012 |
| CN | 103384444 | 11/2013 |
| CN | 103385555 | 11/2013 |
| DE | 3409335 | 9/1985 |
| EP | 0067622 | 12/1982 |
| EP | 2637927 | 9/2013 |
| EP | 2777411 | 9/2014 |
| FR | 719730 | 2/1932 |
| FR | 2041596 | 1/1971 |
| GB | 291600 A | 6/1928 |
| GB | 1282097 | 7/1972 |
| GB | 2024644 | 1/1980 |
| JP | 42002568 | 10/1963 |
| JP | S4814547 | 4/1973 |
| JP | S4499310 | 9/1975 |
| JP | H0207814 | 1/1990 |
| JP | H11247001 | 9/1999 |
| JP | 2003135472 | 5/2003 |
| JP | 3098099 U | 2/2004 |
| JP | 2004337393 | 12/2004 |
| JP | 2004036067 | 5/2005 |
| JP | 2005-273094 | 10/2005 |
| JP | 2005292006 | 10/2005 |
| JP | 2010-517654 A | 5/2010 |
| JP | 3171026 | 10/2011 |
| WO | 1996020783 | 7/1996 |
| WO | 1998046144 | 10/1998 |
| WO | 2003020061 | 3/2003 |
| WO | 2008150966 | 12/2008 |
| WO | 2009152649 | 12/2009 |
| WO | WO 2010/056280 A1 | 5/2010 |
| WO | 2011048518 | 4/2011 |
| WO | 2012168449 | 12/2012 |
| WO | 2013055409 | 4/2013 |
| WO | 2012156335 | 9/2014 |
| WO | 2014143853 | 9/2014 |

(56) References Cited

FOREIGN PATENT DOCUMENTS

| WO | WO 2015/061663 A1 | 4/2015 | |
|---|---|---|---|
| WO | WO-2017172964 A1 * | 10/2017 | ......... A41D 13/0512 |
| WO | 202008500 | 1/2020 | |
| WO | 2020005409 | 1/2020 | |
| WO | 2020048518 | 3/2020 | |
| WO | 2020051545 | 3/2020 | |
| WO | 2020054262 | 3/2020 | |
| WO | 2020055409 | 3/2020 | |
| WO | 2020056280 | 3/2020 | |
| WO | 2020061663 | 4/2020 | |
| WO | 2020074350 | 4/2020 | |
| WO | 2020143853 | 7/2020 | |
| WO | 2020150966 | 7/2020 | |
| WO | 2020152649 | 7/2020 | |
| WO | 2020156335 | 8/2020 | |
| WO | 2020168449 | 8/2020 | |
| WO | 2020172964 | 9/2020 | |
| WO | 2020200672 | 10/2020 | |

OTHER PUBLICATIONS

WO, PCT/US2017/020445 ISR and Written Opinion, dated May 10, 2017.
Batson "Anatomical Problems Concerned in the Study of Cerebral Blood Flow, Federation Proceedings" Federation of American Societies for Experimental Biology, 1944, 139-144, vols. 3-4.
Baum "St. X, Moeller aid in concussion prevention study" Cincinnati.com, Jan. 8, 2016.
Cardosoa "Microplate Reader Analysis of Triatomine Saliva Effect on Erythrocyte Aggregation" Antonio ValadÃ£o Cardosoa et al., Materials Research, vol. 10, No. 1, 31-36, 2007.
Ferguson "Cervical Collars: A Potential Risk to the Head-Injured Patient" International Journal of Care for the Injured, (1993), vol. 24, No. 7, pp. 454-456.
Finnie "Animal Models Traumatic Brain Injury" Veterinary Pathology, 2002, 679-689, vol. 39.
Gilland "A Cinemyelographic Study of Cerebrofspinal Fluid Dynamics"Amer J of Roent, 106 (2): 369 (1969).
Gregg "Experimental Approaches to the Study of the Cerebral Circulation" Fed. Proc., 1944, 3:144.
Hartlage "Brain Injury from Motor Vehicle Accidents, Preventable Damage" Brain Vulnerability and Brain Health. New York: Springer Publishing Company 1992.
Kitano "The Elasticity of the Cranial Blood Pool" Journal of Nuclear Medicine 5:613-625, 1964.
Leonard "Comparison of central venous and external jugular venous pressures during repair of proximal femoral fracture" British Journal of Anaesthesia (2008), vol. 101, No. 2, pp. 166-170.
May "Woodpecker Drilling Behavior, an Endorsement of the Rotational Theory of Impact Brain Injury" Arch Neurology, Jun. 1979, 370-373, vol. 36.
Moyer "Effect of Increased Jugular Pressure on Cerebral Hemodynamic" Journal of Applied Physiology, Nov. 1954, 245-247, vol. 7, No. 3.
Omalu "Concussions and NFL: How the name CTE came about" CNN, Dec. 22, 2015.
Orcutt "New Collar Promises to Keep Athletes' Brains from "Sloshing" During Impact" MIT Technology Review, Feb. 3, 2016.
Performance Sports Group Ltd., "Performance Sports Group and Leading Medical Experts Unveil First-of- Its-Kind Technology to Address Mild Traumatic Brain Injury" PR Newswire, Nov. 17, 2015.
Taylor"New wearable neck collar could help reduce brain injuries in athletes"Sports Illustrated, Jun. 15, 2016.
Templer, Donald I., et al., "Preventable Brain Damage, Brain Vulnerability and Brain Health" Part I: Impact Damage; ECT and Permanent Brain Damage, Springer Publishing Company, New York pp. 95-107 (1992).
Torres, "Changes in the electroencephalogram and in systemic blood pressure associated with carotid compression", Neurology 1970; 20:1077-1083.
Tyrell "Observations on the C.S.F Pressure during Compression of the Jugular Veins"Postgrad. Med. J. 1951;27;394-395.
Vannucci "Carbon dioxide protects the perinatal brain from hypoxic-ischemic damage: an experimental study in the immature rat" Department of Pediatrics (Pediatric Neurology), Jun. 1995, 868-874, vol. 95, No. 6.
Walusinski et al. "How Yawning Switches the Default-Mode Network to the Attentional Network by Activating the Cerebrospinal Fluid Flow" Clinical Anatomy 27:20 ⨏ 209 (2014).
Vasavada et al. "Head and Neck Anthropometry, Vertebral Geometry and Neck Strength in Height-Matched Men and Women" J. Biomechanics, 41 (2008) 114-121.
Brain Injury Association of AmericaTransportation-related incidents are leading cause of brain injury www.biausa.org; Apr. 2001.
Boeing "Airplane Vibration"Boeing Aero Magazine, No. 16, Oct. 2001.
Ilic et al "Potential Connections of Cockpit Floor Seat on Passive Vibration Reduction at a Piston Propelled Airplane" Technical Gazette 21, 3(2014) 471-478.
Terhardt "Dominant Spectral Region" The Wayback Machine, Feb. 20, 2000, https://web.archive.org/web/20120426090422/http://www.mmk.e-technik.tu-muench . . . .

* cited by examiner

METHODS AND DEVICES TO REDUCE DAMAGING EFFECTS OF CONCUSSIVE OR BLAST FORCES ON A SUBJECT

CROSS-REFERENCE TO RELATED APPLICATIONS

The subject application is a continuation of International Patent Application No. PCT/US17/20445, filed Mar. 2, 2017, which claims priority to U.S. Provisional Patent Application No. 62/302,509, filed on Mar. 2, 2016, both of which are incorporated by reference herein in their entirety for all purposes.

FIELD

The present disclosure is generally related to methods and devices for reducing the effects of exposure to concussive events.

BACKGROUND

Traumatic brain injury (TBI) continues to be one of the most common causes of death and morbidity in persons under age 45, even in western societies. A reported 1.7 million people suffer from TBI annually in the United States alone, resulting in an estimated per annum total cost of over $60 billion. Historically, prevention of skull and brain injury has focused on the use of helmets as external cranial protection. Although headgear is effective in preventing the most devastating intracranial injuries—penetrating injuries and skull fractures—headgear is somewhat limited in its ability to reduce instances of concussions or damage to the structures within the cranium. The vast majority of concussions and other traumatic brain injuries occur when a person is subjected to high velocity acceleration-deceleration mechanisms which are not sufficiently mitigated by helmets. Such forces also are known to cause injury to the internal structures of the ear, eye, and nose. These injurious forces may be imparted when the body suffers a violent collision, such as in a car accident or during a contact sport such as football, or when the body is subjected to a blast wave. In large part, relative freedom of movement of the human brain within the cranial cavity predisposes it to both linear and rotational force vectors, with resultant energy absorption causing cellular disruption and dysfunction, sometimes with delayed cell death.

It has been discovered that injuries to the brain, eye, ear, and nose caused by concussive forces and blast waves may be reduced or prevented by moderately increasing the blood pressure and/or blood volume within the target structure by fully or partially occluding venous blood flow from that structure. Specifically, elevated intracranial blood pressure/volume mitigates brain injury, elevated intraocular pressure mitigates ocular structure injury; and elevated intracochlear pressure mitigates hearing loss and damage to the inner ear. Fully-circumferential and partially circumferential collars designed to be worn about the neck and that apply pressure to the internal jugular vein(s), external jugular vein(s), and/or other neck veins have been designed. These collars are typically designed to apply about 5-80 mm Hg pressure to the neck veins. However, these collars do not always provide the most convenient device or manner of application for all activities and situations. Accordingly, the present invention encompasses alternate systems, devices, and associated methods for applying pressure to target veins (i.e., fully or partially occluding venous blood flow) from the target structures for which injury mitigation is desired.

SUMMARY OF THE INVENTION

In various aspects, the invention provides systems, devices, and associated methods for applying pressure to one, two, or more neck veins of a subject in order to mitigate traumatic brain injury (TBI) (e.g., concussion and chronic traumatic encephalopathy), injury to an ocular structure, or injury to the inner ear of the subject.

These and other aspects of the invention will now become apparent to those of ordinary skill in the art upon review of the following description of embodiments of the invention in conjunction with the accompanying drawings.

In some embodiments of any of the foregoing aspects of the invention, the pressure applied to the neck vein may less than or equal to about 25, 30, 35, 40, 45, 50, 55, 60, 65, 70, 75, 80 mm Hg, or greater than or equal to about 5, 10, 15, 20, 25, 30, 35, or 40 mm Hg, including between about 10-80 mmHg, such as between about 10-70 mmHg, such as between about 10-60 mmHg, such as between about 10-50 mmHg, such as between about 10-40 mmHg, such as between about 15-80 mmHg, such as between about 15-70 mmHg, such as between about 15-60 mmHg, such as between about 15-50 mmHg, such as between about 15-40 mmHg, such as between about 20-80 mmHg, such as between about 20-70 mmHg, such as between about 20-60 mmHg, such as between about 20-50 mmHg, such as between about 20-40 mmHg.

In other embodiments, the devices are adapted to apply pressure to one or both external jugular veins (EJV), one or both internal jugular veins (IJV). In other embodiments, the devices are adapted to apply pressure to both the EJV and IJV on one side of the neck or simultaneously on both sides of the neck. In other embodiments, the devices are adapted to apply pressure to one or more (e.g., two) vertebral veins alone or in combination with one or both of the EJVs and/or one or both of the IJVs.

Figure 1:
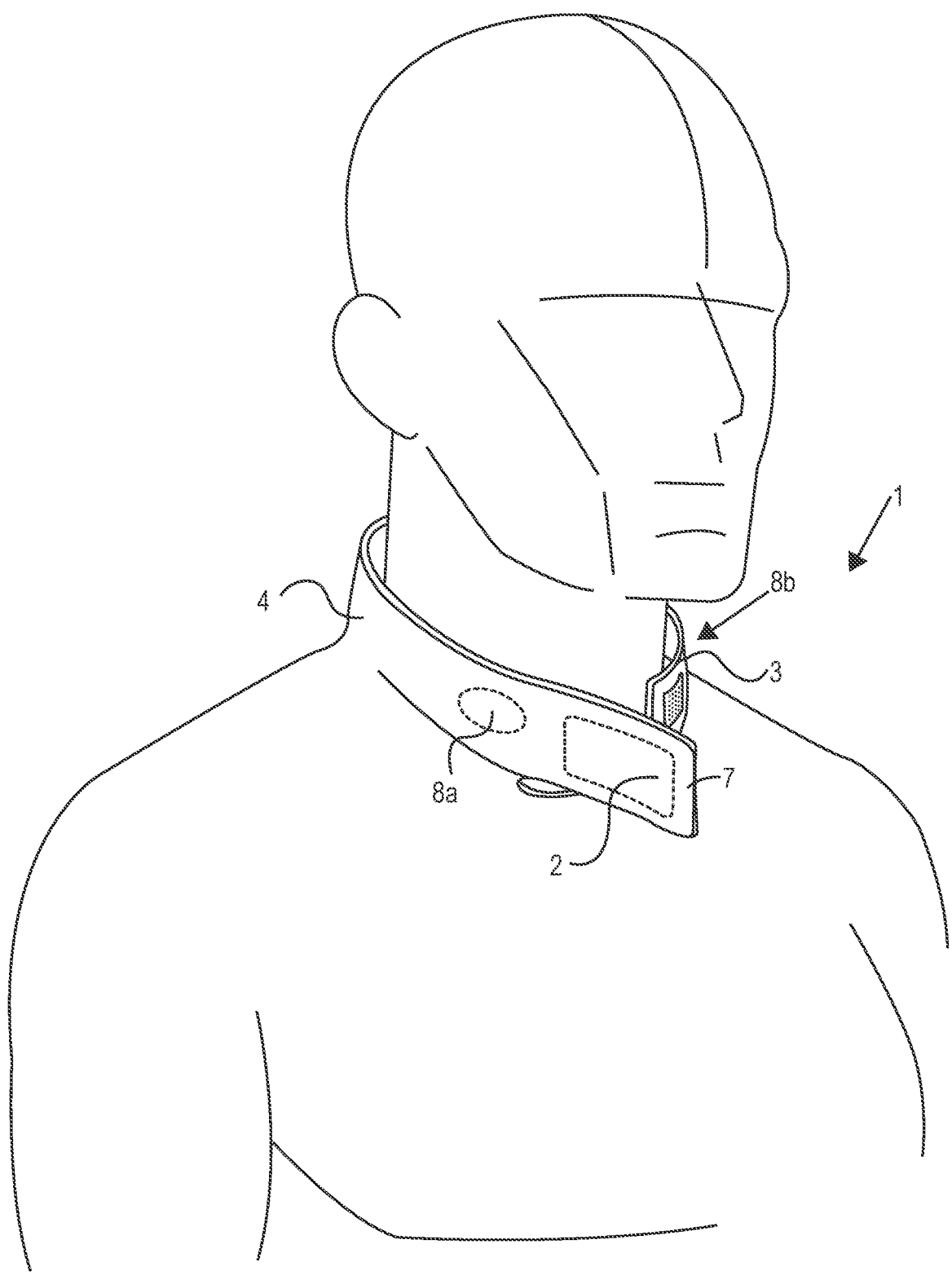
FIG. 1 is an exemplary diagram of a system embodied in an open collar garment for reducing the effects of exposure to concussive events.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION OF THE PREFERRED EMBODIMENTS

Various embodiments or examples may be implemented in numerous ways, including as a system, a process, or an apparatus/device. The invention is described in terms of various features and functionalities. It is understood that any particularly claimed invention may incorporate any one or more of the disclosed features and functionalities in any order or combination. The detailed description and figures are provided to facilitate an understanding of the invention, but are not intended to be limiting in any way.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

The mitigation of blast wave and collision damage is based largely on the principle of energy absorption. To reduce this energy absorption, one must attempt to more closely approximate elastic collisions. Elastic collisions are those that result in no net transfer of energy, chiefly, acoustic, kinetic, vibrational, or thermal (also stated as a coefficient of restitution (r) approximating 1.0). Various embodiments described below may locally alter, elevate, or temporarily maintain an altered physiology of an organism to reduce the likelihood of energy absorption through non-elastic collisions whereby the coefficient of restitution (r) is increased. The coefficient of restitution (r) indicates the variance of an impacting object away from being a complete total elastic collision (r=1.0 represents a perfectly elastic collision with no energy transfer). Blast or energy absorption in an organism can be viewed as a collision of bodies and thus be defined by a transfer of energies through elastic or inelastic collisions. The mechanisms for biological fluids and molecules to absorb energy can thus be identified and the resultant means to mitigate that absorption can be achieved through several mitigation techniques. Dissipation of energies post blast is also potentiated through these techniques.

One technique for mitigating the effects of concussions can be by reversibly increasing pressure or volume within the organs or cells of the organism. Applying this concept to the contents of the skull, the intracranial volume and pressure can be reversibly increased by a device that reduces the flow of one or more of the cranial outflow vessels. One embodiment of such a device would compress the outflow vessels enough to cause an increase in venous resistance, yet not enough to increase an arterial pressure leading into the cranium above approximately 80 mm Hg.

Mitigating the concussive effects by increasing the pressure of the fluid contents of the brain can significantly reduce the propensity for damage to the brain tissue or its blood vessels by reducing the compressibility of the brain. The reduction in compressibility results in reduced absorption of kinetic, acoustic, thermal, and vibrational energy by the brain.

With respect to the inner ear, it is known that the cochlear aqueduct is in direct communication with the cerebrospinal fluid (CSF) and the vein of the aqueduct drains directly into the internal jugular vein (IJV). The venous blood empties either directly into the inferior petrosal sinus or internal jugular vein, or travels through other venous sinuses via the vein of the vestibular or cochlear aqueduct. Reduced outflow of the internal jugular would necessarily congest the cochlear vein and take up the compliance of the inner ear, thereby improving elastic collisions at the macroscopic, cellular, and molecular level and, thus, reducing energy impartation into these structures.

Approximately 30 ml (21%) of a total CSF volume of 140 ml resides within the spinal axis, and about one-third of the compliance of the CSF system has been attributed to the spinal compartment. As in the brain, increasing the pressure and volume of the CSF within the spinal compartment reduces the susceptibility of the spinal compartment to concussive injuries by increasing the elasticity of the contents of the spinal column, thereby reducing the amount of energy absorbed by the contents of the spinal column when subjected to a concussive force.

With respect to ocular injuries, it is known that the woodpecker has a "pectin apparatus" that protects the globe of its eyeball from the 1200 G impact of pecking. The sole purpose of the pectin apparatus appears to be to increase the volume and pressure of the vitreous humor inside the eyeball. The pectin apparatus is situated within the eyeball and fills with blood to briefly elevate intraocular pressure, thereby maintaining firm pressure on the lens and retina to prevent damage that might otherwise occur during the 80 million pecking blows over the average woodpecker's lifetime. While humans lack the pectin apparatus, it is possible to increase intraocular pressure by externally applying pressure on the external jugular veins (EJV).

One aspect of the present invention, therefore, encompasses a device that raises intracranial volume and/or pressure, intraocular pressure, and/or intracochlear pressure when worn by a subject animal or human. The device is configured to apply pressure to the outflow vasculature in the neck (e.g., one or more internal and/or external jugular vein), thus increasing intracranial and/or intraocular pressures and volumes in the wearer. In doing so, the device reduces energy absorption by the wearer due to concussive effects, thus reducing the likelihood of one or more of brain, spine, and eye damage from a concussive event. Devices of the instant invention could be worn preferably before, in anticipation of and during events with traumatic brain injury risks and worn throughout the duration of the actual concussive event (e.g., collision or blast wave).

Safely and reversibly increasing cerebral blood volume by any amount up to 10 cubic centimeters (cm 3 and pressure by any amount up to 80 millimeters of mercury (mmHg) would serve to fill up the compliance of the cerebral vascular tree and thus reduce the ability to absorb external energies through energy absorption. With the application of measured pressure to the neck, the cranial blood volume increases rapidly and plateaus at a new higher level. Moyer et al. reported that cerebral arterial blood flow was not affected by obstructing the venous outflow of blood from the brain. The blood volume venous pressure relationship shows a diminishing increase in volume with each increment of neck pressure over the range 40 to 70 mm of mercury. It is of interest that the cranial blood volume increases from about 10 to about 30 percent (with this neck pressure). Similarly, CSF pressure also increases upon compression of the individual jugular veins. Under the same neck pressure, the average rise in CSF pressure is about 48%. These changes occur very rapidly upon initiation of pressure; jugular compression increases cerebral blood flow to a new plateau in as little as 0.5 seconds. Although lesser cranial pressure and volume increases may still have beneficial effects, it is intended that devices of the instant invention increase cranial blood volume by at least 3 cm 3 through an application of at least 5 mm Hg neck pressure.

Devices of the present invention, therefore, may take many forms, but share the functional feature of constantly or intermittently applying pressure to one or more veins in the neck (specifically, but not limited to the internal and external jugular veins, the vertebral veins, and the cerebral spinal circulation, and most preferably, the interior jugular vein) to restrict blood flow exiting the brain. Thus, the instant devices include at least one inwardly directed protuberance that is inwardly directed and contacts the neck of the wearer of the device, and at least one means for applying pressure to the one or more protuberances such that the protuberances apply pressure to one or more veins in the neck, thereby restricting blood flow exiting the brain.

Inwardly Directed Protuberances that Contact the Neck of the Wearer

In some embodiments, the one or more inwardly directed protuberances are integral to the component of the device responsible for applying pressure to the neck. In alternative embodiments, the one or more inwardly directed protuberances are distinct from the component of the device responsible for applying pressure to the neck. Is to be generally understood that the protuberances may be any suitable shape, e.g., pointed or round, and comprising of any suitable material, such as defined by a rigid or semi-rigid plastic body, a thickened region of a collar, and the like.

In some embodiments, the protuberances may substantially be defined by a bladder, whereby pressure is exerted on the neck of the wearer when the bladder is inflated or filled. In some related embodiments, the bladder may contain reversibly compressible foam that is in fluid communication with the external atmosphere. In further related embodiments, the interior of the bladder is in fluid communication with the external atmosphere via a pressure release valve. In embodiments comprising a bladder, foam, and valve, these components may be configured so that the foam expands within the bladder, drawing air into the bladder through the pressure valve to inflate the bladder to a desired pressure. However, the pressure release valve may be configured to allow for release of air from the bladder upon an application of pressure to the device that may otherwise raise the amount of pressure applied to the neck to an uncomfortable or undesirable level. In other embodiments, the bladder may contain a gas or liquid and may be outfitted or configured to interface with a pump mechanism such that the pressure of the bladder may be user adjusted. The pump mechanism may be any suitable pump mechanism as would be understood in the art, such as e.g., a powered pump, or a hand-compressible pump whereby a liquid, air or a gas can be applied to the bladder. In certain embodiments the device may further comprise a pressure sensor operably linked to the pump mechanism or bladder whereby the degree of inflation may be regulated as to the extent and duration of the pressure applied to an underlying neck vein.

In some embodiments, the protuberance comprises a spring or resilient compressible material. In these embodiments, the spring or resilient compressible material is disposed within the protuberance such that application of the protuberance to the neck at least partially compresses the spring or resilient compressible material. The force exerted by the at least partially compressed spring or resilient compressible material ensures that the protuberance maintains a desired pressure on the neck.

In some embodiments, the device may comprise a resilient arcuate band having a general C, V, or U-shape. The band may be formed of a resilient spring-like material whereby the C, V, or U-shaped band is forced open as the device is applied. After application of the device, spring tension causes compression of the band, resulting in the mid-point or bend-point of the band to extend toward and apply pressure to the neck. Thus, in these embodiments, the mid-point or bend-point of the bands are the protuberances that contact the neck of the wearer.

In some embodiments, at least a portion of an inwardly directed surface of the one or more protuberances may be coated with a suitable adhesive to facilitate placement of the protuberances on the neck, and prevent movement of the protuberance once in place. Additionally or in the alternative, in embodiments where the protuberances are distinct from the component of the device which applies pressure to the neck, at least a portion of an outwardly directed surface of the one or more protuberances may be coated with a suitable adhesive. In such embodiments, the design of the device may such that a protuberance may be paced between a component which applies pressure to the neck and the neck itself. An outwardly directed surface of the protuberance would then contact an inwardly directed surface of the pressure-providing component of the device such that the adhesive on the outwardly directed surface of the protuberance would prevent movement of the protuberance once in place.

One exemplary embodiment of this type (discussed in greater detail below) comprises three pieces: two round or oval plastic protuberances (one for application to either side of the neck) and an elastic collar. The device could be applied by first putting the collar around the neck, and then by placing the plastic protuberances between the collar and the neck at the appropriate locations so as to apply pressure to the internal jugular vein on either side of the neck. As will be appreciated for this example, a mild adhesive coating on the inwardly directed and/or outwardly directed surfaces of the protuberances will assist in preventing movement of the protuberances once they are installed between the collar and the neck. Alternately, if the protuberances have an adhesive coating of sufficient strength at least on the inwardly directed surfaces, the protuberances may be placed on the appropriate locations on the neck prior to installation of the collar. In either case, the collar applies pressure to the protuberances, which in turn applies pressure to the neck veins.

In other embodiments of this type, two protuberances may be secured to one another with a tether of the appropriate length to act as an alignment and spacing guide for application on either side of the neck. In some embodiments, the tether may be removable, so that once the protuberances are applied to the neck, the tether may be pulled or otherwise removed, leaving the protuberances in place on the neck of the wearer.

In some embodiments, the protuberances are compressible pads or solid forms sized to apply pressure substantially only to the internal jugular vein(s) and/or the external jugular vein(s).

It is also understood that the devices need not have a specifically defined protuberance it order to apply pressure to a neck vein. For example, the device may have a pad or thickened region that is adapted to be positioned over the target neck vein(s). The pad or thickened region may be rigid, semi-rigid, or inflatable. For convenience, several of the devices described herein reference protuberances and similar structures. This description is not intended to be limiting and instead is intended to refer generically to that portion of the device that is adapted to positioned over the target neck vein(s) and apply direct pressure thereto.

Circumferential and Semi-Circumferential Collar Type Devices

In some embodiments, the device may be a circumferential or semi-circumferential collar. A circumferential collar is a collar that encircles the entire circumference of the neck when the device is worn by an animal or human subject. A semi-circumferential collar is a collar that encircles a majority of the circumference of the neck when the device is worn by an animal or human subject. The portion of the circumference of the neck that is not encircled by a semi-circumferential collar may be disposed at any location around the circumference of the neck, so long as the encircled portion allows for application of pressure on inwardly directed protuberances specifically located in order to restrict blood flow exiting the brain. Typically, the open portion will be either located at the front of the throat (e.g., in some embodiments, a semi-circumferential collar may encircle the neck except an area substantially defined by laryngeal prominence, also known as the "Adam's apple"), or located at the back of the neck.

In embodiments where the device comprises a circumferential collar, it is contemplated that the applied pressure to the neck may be due to an internal dimension of the collar being less than the neck diameter. This difference in internal dimension of the collar may be achieved by any number of configurations dictated by the materials used to construct the collar. For instance, in a collar comprising inelastic materials, the collar may be sized to apply the appropriate pressure when worn by an individual. In these embodiments, the size of the collar may be such that the collar is tailored to an individual and thus requires no adjustment for fit. Alternatively, the size of the collar may be adjustable by any of a number of means, some of which are discussed further below. In some embodiments, the collar may comprise an elastic material such that the internal dimension of the elastic collar is expanded when the collar is worn, and the collar applies pressure to the neck of the wearer as a result of compressive force exerted by the expanded elastic material. Elastic materials may also confer the benefit of increased comfort for the wearer.

In embodiments where the device comprises a semi-circumferential collar, it is contemplated that the collar comprises a resilient arcuate band having a general C, V, or U-shape. In these embodiments, it is intended that the band extend a majority, if not the entirety, of the length of the collar. In these embodiments, the collar thus semi-rigidly defines a C, V, or U-shape that is expanded as the collar is applied to the neck of a wearer. Spring tension from the expanded resilient arcuate band causes a compressive force that keeps the collar in place on the neck and applies the intended pressure to the neck veins.

In these embodiments, at least one inwardly directed pad or form may be disposed at appropriate locations on opposing sides of the collar, such that the inwardly directed pads or forms are configured to contact the neck and apply pressure to a point above the interior jugular vein. In embodiments where the semi-circumferential collar is open at the front of the throat, the area of the neck not covered by the semi-circumferential collar may define a region approximating the laryngeal prominence, also known as the "Adam's apple." In these embodiments, the inwardly directed pad or forms disposed on opposing sides of the collar may be located at or near the terminal ends of the resilient arcuate band. In embodiments where the semi-circumferential collar is open at the back of the neck, the inwardly directed pads or forms may not be disposed near the terminal ends, but rather may be disposed much closer to the mid-point of the band.

In some embodiments where the device comprises a circumferential collar or a semi-circumferential collar that is open at the back of the neck, the device may comprise a laryngeal bridge that defines a cut-out at the front of the neck. The size and shape of the laryngeal bridge may be configured so as to minimize contact of the collar with the laryngeal prominence in order to make the collar more comfortable for the wearer. In these embodiments, the laryngeal bridge may be of any suitable material as to provide a rigid or semi-rigid continuation of the collar around the front of the neck. In some embodiments, the laryngeal bridge may comprise thick or reinforced textile material, plastic, metal, or any combination thereof.

In some embodiments where the device comprises a circumferential collar, the device comprises two components: a front section comprising the one or more inwardly directed protuberances and a laryngeal bridge, and a back section comprising a length of fabric configured to be removably attached at either end to corresponding ends of the front section. In some embodiments, the length of fabric comprises an elastic material; alternatively, the length of fabric may comprise an inelastic fabric. Removable attachment of either end of the front section to the corresponding end of the back section may be by any suitable method known in the art, such as a hook and ladder attachment, a hook and loop attachment, a snap, a button, a chemical adhesive, or any of a number of attachment mechanisms that would be known to one skilled in the art. A device with removable attachment means could also have a breakaway release mechanism whereby the device can break open or apart at a predetermined force to prevent the device from inadvertently being snagged or compressing too tightly.

Many of the devices described herein are described as potentially comprising an elastic material. More particularly, it is intended that these devices may comprise materials that are elastically elongatable around the circumference of a subject's neck. Elastic materials can be any material which when stretched will attempt to return to the natural state. Exemplary materials may include one or more of textiles, films (woven, non-woven and netting), foams and rubber (synthetics and natural), polychloroprene (e.g. NEOPRENE®), elastane and other polyurethane-polyurea copolymerss (e.g. SPANDEX®, LYCRA®), fleece, warp knits or narrow elastic fabrics, raschel, tricot, milanese knits, satin, twill, nylon, cotton tweed, yarns, rayon, polyester, leather, canvas, polyurethane, rubberized materials, elastomers, and vinyl. There are also a number of elastic materials which are breathable or moisture wicking which may be preferable during extended wearing periods or wearing during periods of exercise. As indicated above, elastic materials may confer the benefit of increased comfort for the wearer by providing sufficient compressive pressure, yet remaining flexible to accommodate a full range of motion and/or muscle flex in the wearer.

In addition, a device constructed with an elastic material may be partially reinforced, coated, or otherwise include one or more protecting materials such as Kevlar® (para-aramid synthetic fibers), Dyneema® (ultra-high-molecular-weight polyethylene), ceramics, or shear thickening fluids. Such reinforced materials may confer the benefit of increasing the devices resistance to lacerations. As such, reinforced devices may provide the user the added benefit of protecting the neck from damage from lacerations.

In some embodiments, circumferential or semi-circumferential collars may be constructed with materials, elastic or otherwise, that are fire resistant.

The device may encompass horizontally, the entire neck or just partially up and down the neck. The width of the devices described herein may range from a mere thread (at a fraction of an inch) to the length of the exposed neck (up to 12 inches in humans or greater in other creatures), the length may range from 6 to 36 inches to circumnavigate the neck. The width of the compression device could be as small as ¼ inch but limited only by the height of the neck in largest width, which would be typically less than 6 inches. The thickness of said device could range from a film being only a fraction of a millimeter to a maximum of that which might be cumbersome yet keeps ones neck warm, such as 2-3 inches thick.

In some embodiments, a circumferential or semi-circumferential collar may comprise a shape memory polymer. In such embodiments, the collar would be applied to the neck of a user and then the appropriate stimulus would be applied to the shape memory polymer, causing the collar to shrink to fit.

In some embodiments, a circumferential or semi-circumferential collar may comprise a bladder whereby the pressure exerted on the neck of the wearer by the collar may be adjusted by inflating or deflating the bladder. In some related embodiments, the bladder may contain reversibly compressible foam that is in fluid communication with the external atmosphere. In further related embodiments, the interior of the bladder is in fluid communication with the external atmosphere via a pressure release valve. In embodiments comprising a bladder, foam, and valve, these components may be configured so that the foam expands within the bladder, drawing air into the bladder through the pressure valve to inflate the bladder to a desired pressure. However, the pressure release valve may be configured to allow for release of air from the bladder upon an application of pressure to a protuberance that may otherwise raise the amount of pressure applied to the neck to an uncomfortable or undesirable level. In other embodiments, the bladder may contain a gas or liquid and may be outfitted or configured to interface with a pump mechanism such that the pressure of the bladder may be user adjusted. The pump mechanism may be any suitable pump mechanism as would be understood in the art, such as e.g., a powered pump, or a hand-compressible pump whereby a liquid, air or a gas can be applied to the bladder. In certain embodiments the device may further comprise a pressure sensor operably linked to the pump mechanism or bladder whereby the degree of inflation may be regulated as to the extent and duration of the pressure applied to an underlying neck vein. In some embodiments, the bladder is disposed to at least include a portion of the collar other than above a protuberance. In some embodiments, the bladder is disposed through a majority of the circumference of the collar.

In some embodiments, a circumferential or semi-circumferential collar may further comprise a pouch or pocket. This pouch or pocket may be externally accessible, i.e., accessible while the collar is being worn, or only accessible when the collar is removed. The dimensions of such a pouch or pocket may be such that the pouch or pocket is suitable to carry one or more items useful for the treatment of TBI related calamities, such as a material enabling $CO_2$ delivery, carbonic anhydrase tablets, methylene blue, DHA, smelling salts, etc.

In some embodiments, a circumferential or semi-circumferential collar may further comprise an electrical circuit comprising a piezoelectric heat pump configured to alter the temperature of the inwardly directed surface of the collar. Such a heat pump may be used to either heat or cool the device, for example by as much as 70° from ambient temperature.

In some embodiments, a circumferential or semi-circumferential collar may further comprise an electrical circuit configured to provide a therapeutic electrical stimulation to the neck of the wearer. For example, an electrical circuit may be configured to provide transcutaneous electrical nerve stimulation.

Non-Collar Type Devices

In some embodiments, the device may be a non-collar type device which consists of two separate elements, intended to be used in pairs, each contacting one or a set of neck veins on one side of the neck. The non-collar type devices may be attached directly to the subject's skin or they may be anchored to another structure such as a garment, protective equipment (e.g., a helmet, shoulder pads, etc.), or headphones, as described herein.

As with collar-type devices, non-collar type devices also utilize inwardly directed protuberances to apply pressure to the neck at specific locations in order to restrict blood flow exiting the brain. Any of the protuberances described above may find use in non-collar type devices.

In some embodiments in which the non-collar devices are affixed directly to the skin, the externally directed side of a protuberance may be covered by flexible material that extends beyond the area defined by the protuberance. In these embodiments, at least a portion of this extended inwardly directed surface contacts the neck when the device is in place. In some embodiments, the at least a portion of the inwardly directed surface of the flexible material that contacts the neck is coated with an appropriate adhesive, such that when applied to the neck, the flexible material holds the protuberance in an appropriate position and applies pressure to a neck vein. The flexible material may be elastic or non-elastic. The flexible material may be any suitable synthetic or natural woven or textile material, or any suitable plastic.

Such embodiments may comprise a pair of material/protuberance combinations for application to both sides of the neck. Some related embodiments may comprise a pair of material/protuberance combinations joined by a tether, as described above. The tether may be of appropriate length so as to serve as an aid to alignment and proper placement of the protuberances at the correct locations on the neck. In some embodiments, the tether may be removably attached to the pair of material/protuberance combinations so that after placement of the protuberances on either side of the neck, the tether is removed.

In some non-collar type devices, the device may comprise a resilient arcuate band having a general C, V, or U-shape. In these embodiments, it is intended that a protuberance is located at or near the terminus of each arm of the band, and that when the device is in place, the band extends around the front of the neck. In these embodiments, the band thus semi-rigidly defines a C, V, or U-shape that is expanded as the device is applied to the neck of a wearer. Spring tension from the expanded resilient arcuate band causes a compressive force that keeps the device in place on the neck and applies the intended pressure to the neck veins via the protuberances. In some embodiments, the resilient arcuate band is sized and shaped such that it does not cross the front of the neck in the general area of the laryngeal prominence. Instead, the band may cross the front of the neck at a position below the laryngeal prominence.

Garments or Other Protective Gear Comprising Integral Protuberances

In yet other embodiments, it is envisioned that protuberances (as described above) may be incorporated into various articles of clothing and/or other protective gear. Such garments and/or other protective gear typically may be designed for specific purposes, e.g., as part of a military uniform, sporting apparel, neck guard for first responders, flame retardant head gear for automobile or motorcycle drivers or firefighters, etc. In any case, protuberances may be included at the appropriate positions in a portion of a garment or protective gear that contacts the neck of the wearer, i.e., the collar, with the collar providing compressive force on the protuberances. As such, any of the closing, alignment, or fitting means, or any other optional feature provided in regards to circumferential or semi-circumferential collar-type devices may be incorporated in garment and/or protective gear embodiments.

In one aspect, the invention provides a system having a garment and a circumferential or semi-circumferential collar, each adapted for use with the other. In one embodiment, the garment has a top portion adapted to receive the collar. For example, the top portion of the garment may have an extended flap which is designed to provide a layer of fabric between the subject's neck and the collar, wherein the extended portion of that flap is folded over, and optionally fastened, to conceal the collar and help hold the collar in place. In another embodiment, the top portion of the garment has a sleeve which is adapted to receive the collar. In another embodiment, the collar is place directly against the subject's skin and the top portion of the garment is adapted to conceal all or part of the collar. Optionally, the inside of the garment and the outside of the collar have a mutually engaging fastening means in order to hold the top portion of the garment in place against the collar. One such suitable fastening means is a hook-and-pile system (e.g., VELCRO®).

In another aspect, the top portion of the garment has integral protuberances permanently affixed therein. Optionally, the top portion of the garment comprises a rigid or semi-rigid member, similar to the stand-alone collar, adapted to apply neck vein pressure via the protuberances. Alternatively or in addition to the rigid member, the top portion of the garment may be fully circumferential with a closing and/or fitting mechanism adapted to apply and control neck vein pressure via the protuberances.

Visual or Tactile Alignment Aids

Any of the embodiments described above may further comprise one or more materials, and/or apply one or more construction methods, designed to provide the user or a $3^{rd}$ party observer with a visual or tactile aid in determining proper alignment and positioning of the protuberances. For instance, a collar type device may include a small strip or patch of a contrasting or reflective material, or a material with a different texture, at the mid-point of the neck. Alternatively or in addition, similar visual or tactile cues may be incorporated into any of the above devices so as to provide an outward indication of the location of a protuberance.

Further, any of the embodiments described above that utilize elastic materials may comprise a dual layered elastic material that exposes a change in graphic or color when sufficiently stretched to apply an appropriate force on an underlying protuberance. In such embodiments, the change in graphic or color may provide a visual cue to the wearer or $3^{rd}$ party observer that the device is applying at least sufficient compressive force.

Incorporated Sensors or Other Electronic Systems

Any of the above devices may also have one or more monitoring, recording, and/or communicating devices attached or embedded. For example, the device may comprise a sensor capable of detecting one or more environmental parameters around the wearer, one or more physiological parameters of the wearer, or some combination thereof. Exemplary environmental parameters that may be detected include time the collar has been worn, barometric pressure, ambient temperature, humidity, acceleration/deceleration (i.e., G forces), positionality (upright/supine), etc. Physiological parameters that may be detected include pulse, blood pressure, plethysmography, dermal temperature, oxygen saturation, carboxyhemoglobin level, methemoglobin level, blood sugar, electrical flow, etc. of the human or animal wearing the device. Any of such sensors may be used to monitor some environmental or physiological characteristic or performance aspect of the wearer. Sensors capable of detecting pulse, blood pressure, and/or plethysmography may serve the additional or alternate purpose of being used as an alignment and/or fit aid, notifying the user when the protuberance is properly placed over a neck vein and is exerting an appropriate pressure so as to restrict blood flow.

In some related embodiments, a device may further comprise an electronic circuit capable of providing visual, auditory, or tactile indicia of malfunction, or an undesirable sensor reading. For instance, an electronic circuit may be configured to vibrate the collar when a pulse or blood pressure sensor detects a reading that is either higher or lower than a predetermined value.

Additionally or in the alternative, any of the above devices may comprise an electronic circuit configured to transmit the location of the wearer. For instance, any of the above devices may comprise an electronic circuit configured to transmit the GPS coordinates of the wearer for tracking the location of the wearer, or for search and rescue purposes.

Additionally or in the alternative, any of the above devices may comprise an electronic circuit configured to transmit and/or receive voice communications between the wearer and a third party.

In some embodiments, the output of such a sensor may be visually or audibly communicated to the user or a third party by another component of the device, e.g., an electronic circuit configured to provide a visual or auditory indication (such as with an LED, piezoelectric speaker, etc.). In some embodiments, the device further comprises a communication means such that a signal from the sensor may be communicated to an external electronic device, such as a smartphone, laptop, or dedicated receiver.

These terms and specifications, including the examples, serve to describe the invention by example and not to limit the invention. It is expected that others will perceive differences, which, while differing from the forgoing, do not depart from the scope of the invention herein described and claimed. In particular, any of the functional elements described herein may be replaced by any other known element having an equivalent function.

Exemplary Embodiments of the Invention

FIG. 1 depicts a system embodied in an upper garment (e.g., shirt, jersey, exercise jacket, etc.) for reducing the effects of exposure to concussive events. In the embodiment depicted in FIG. 1, the garment 1 has an open garment collar 4 that also incorporates a collar extension 7 that includes a reversible closure mechanism (e.g., mating pair members), shown for example as hook-and-pile (e.g., VELCRO®) strips 2 and 3, for closing the open garment collar 4 to form a closed or full collar that fits snugly and entirely around the user's neck. The garment also contains a pair of inwardly directed protuberances 8a and 8b positioned to overly the target neck veins (e.g., EJV and/or IJV) when the collar extension 7 is closed (i.e., the reversible fasteners are closed or mated). The user may control the amount of pressure applied to the neck veins by the protuberances 8a and 8b by the tightness and/or adjustment of collar 4 in the closed configuration. Thus, reversible closure mechanisms that allow for continuous sizing (e.g., VELCRO®) are preferable over closure mechanisms that allow for only discontinuous sizing (e.g., hooks, snaps, etc.) because it allows the user to finely control and customize the fit of collar 4 and the neck vein pressure applied by protuberances 8a and 8b. The garment 1 can be constructed of different types of materials including both elastic and non-elastic fabrics. In particular, collar 4 may be made of elastic or non-elastic fabrics, but elastic fabrics are preferred. Optionally, the protuberances 8a and 8b are placed in pockets on the inside face of the collar 4 and may be permanent (e.g., sewn in) or removable (e.g., an open pocket).

Figure 2:
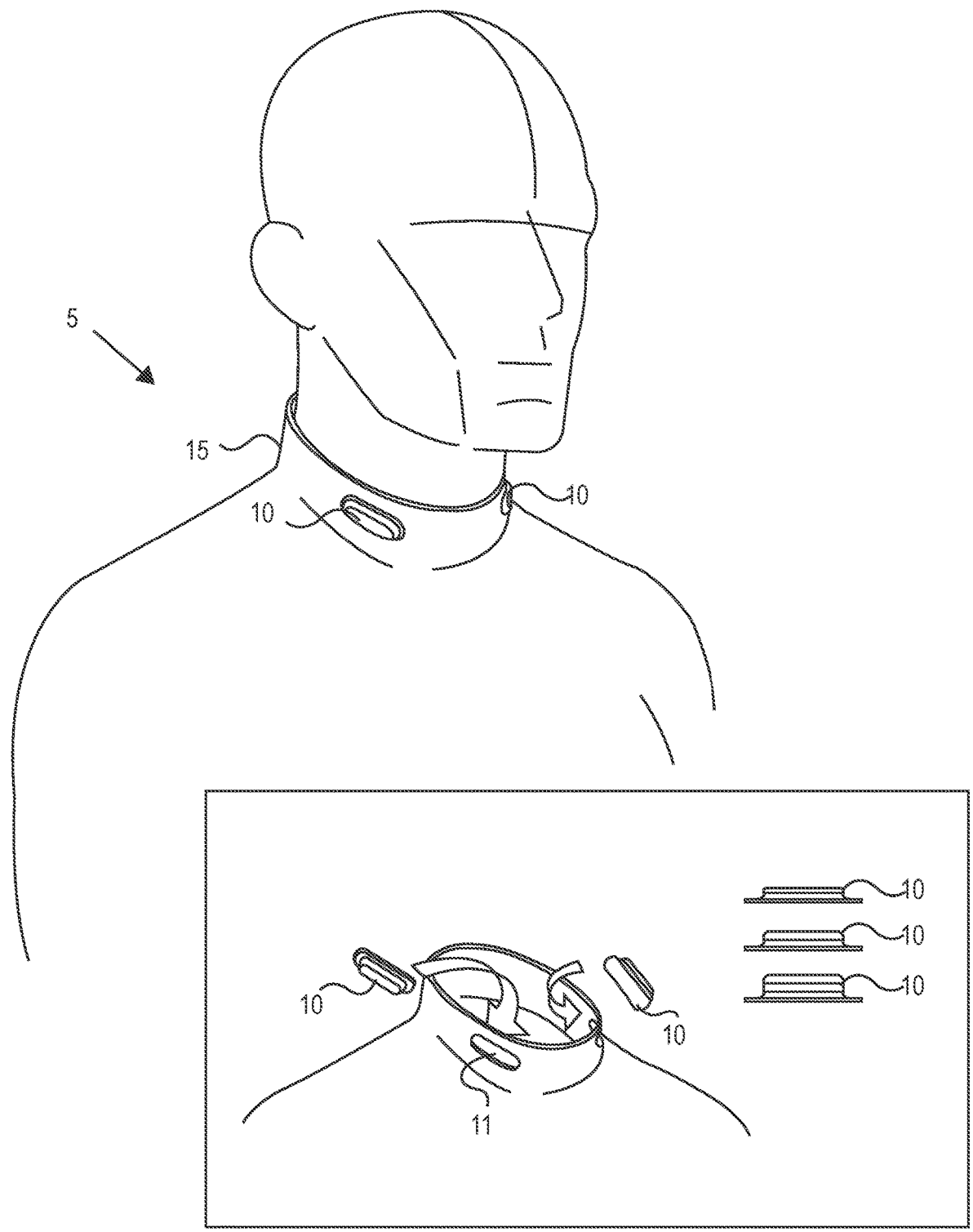
FIG. 2 is an exemplary diagram of a system embodied in a closed collar garment for reducing the effects of exposure to concussive events.

FIG. 2 depicts an exemplary diagram of a system embodied in a closed collar garment for reducing the effects of exposure to concussive events. The embodiment depicted in FIG. 2 has a garment 5 having a flexible and elasticized or a rigid collar 15 which has eyelets 11 positioned to overlie the target neck veins when the garment 5 is worn. Removable protuberances 10 may be disposed through the eyelets 11 to apply pressure on the neck veins. In one embodiment, the invention provides a system comprising the garment 5 and one or more (e.g., two, three, four, five, six, or more) matched pairs of protuberances 10, wherein each matched pair is different is size and/or shape than the other matched pairs so that the user may customize the amount of applied neck vein pressure and/or the size/shape of the area over which the pressure is applied. Garment 5 may be constructed of different types of materials including both elastic and non-elastic fabrics.

Figure 3:
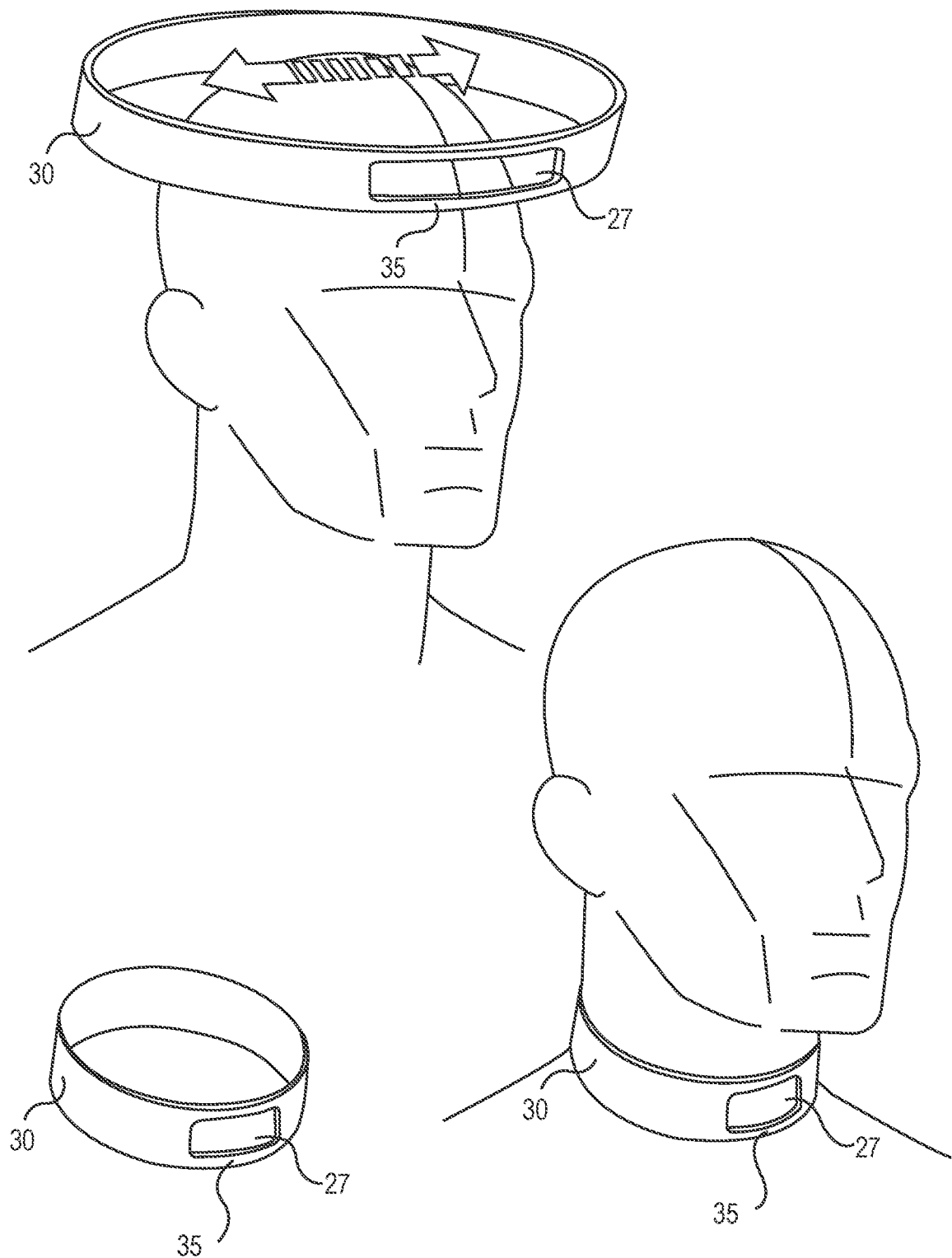
FIG. 3 is an exemplary diagram of an expandable collar device for reducing the effects of exposure to concussive events.

FIG. 3 is an exemplary diagram of a system embodied in a soft collar 30 for reducing the effects of exposure to concussive events. In the embodiment depicted in FIG. 3, the textile neck strap soft collar 30 comprises a collar body and a force zone. The force zone may apply pressure on a plurality of protuberances (not shown) applying pressure on the veins of the wearer's neck or the force zone can apply neck vein pressure without the presence of protuberances. The force zone can be present as a continuous band spanning from one set of neck veins to the other, as illustrated, or it may be present a discontinuous segments that each overlap a set of neck veins. The force zone may be formed of a material different from the material used for the body of the collar 30. The neck band can be comprised of an expandable fabric or a blend of different materials. The device 30 can comprise an expandable seamless neck band that can expand and slide over the head of a wearer. The device 30 can be constructed in various sizes to accommodate different neck sides of wearers.

In some embodiments of the knit collar, a cut-out 27 in the fabric at the tracheal region (i.e., spanning the laryngeal prominence) may be formed for increased comfort of the wearer. In this embodiment, the circumferential area 35 in the tracheal region can be minimized to reduce pressure on the wearer's throat. In one embodiment, the force zone comprises a material that has more resilient elastic properties than that of the body 30. Optionally, the laryngeal bridges 35 are elastic or non-elastic. In another embodiment, the soft collar 30 may be incorporated into a garment and serve as the collar for that garment. The soft collar 30 can also be constructed with different dimensions of the cut-out 27 to accommodate the different physical characteristics of the laryngeal prominence of the wearer.

Figure 4:
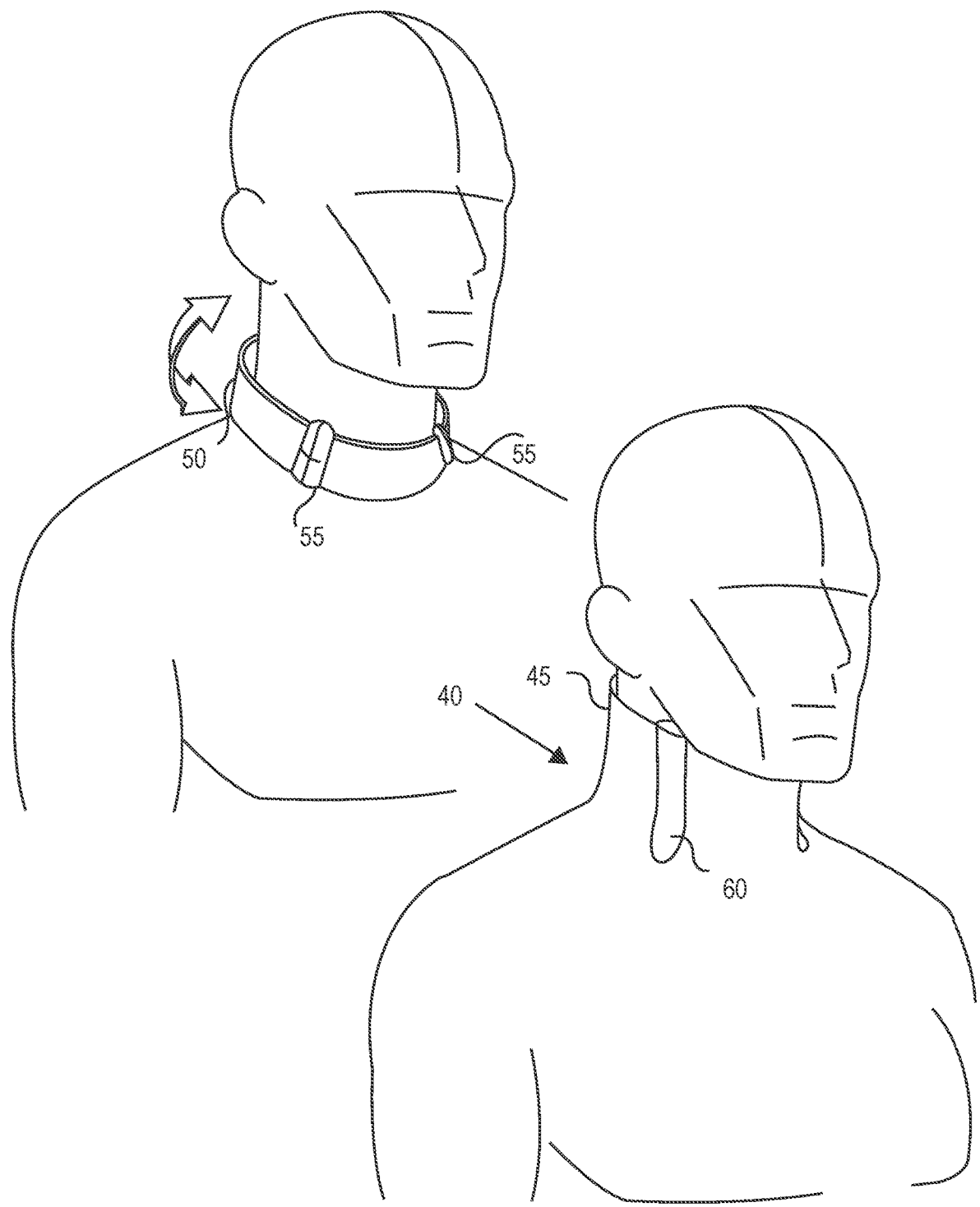
FIG. 4 is an exemplary diagram of a system embodied in a foldable garment for reducing the effects of exposure to concussive events.

FIG. 4 is an exemplary diagram of a system comprising a garment having an elongated and foldable collar with removable clips for reducing the effects of exposure to concussive events. In the embodiment depicted in FIG. 4, the garment 40 has an elongated neck region 45 such as a turtleneck design. The fabric of the neck region 45 can be rolled or folded downward away from the head of the wearer on the remaining fabric 50 and at least one clamp 55 is applied to hold the fabric of the neck region 45 folded. The clamp 55 may be constructed of any conventional material and can be removably coupled to the garment 40. The clamp 55 also acts as a protuberance to apply pressure on the veins of the wearer's neck when properly positioned. Although only one clamp 55 is depicted in FIG. 4, two or more clamps can be worn with the garment 40. The garment 40 can be constructed of different types of materials including both elastic and non-elastic fabrics. The folding of the fabric of the neck region 45 can increase the pressure applied to the clamp 55 and, therefore, the neck veins. Neck vein pressure also may be increased through the use of an elasticized material in the extended neck region 45. The garment 40 can also incorporated an application region 60 that can inform a wearer of the proper placement of the clamp 55. The application region 60 may have a different color or other conventional marking.

Figure 5:
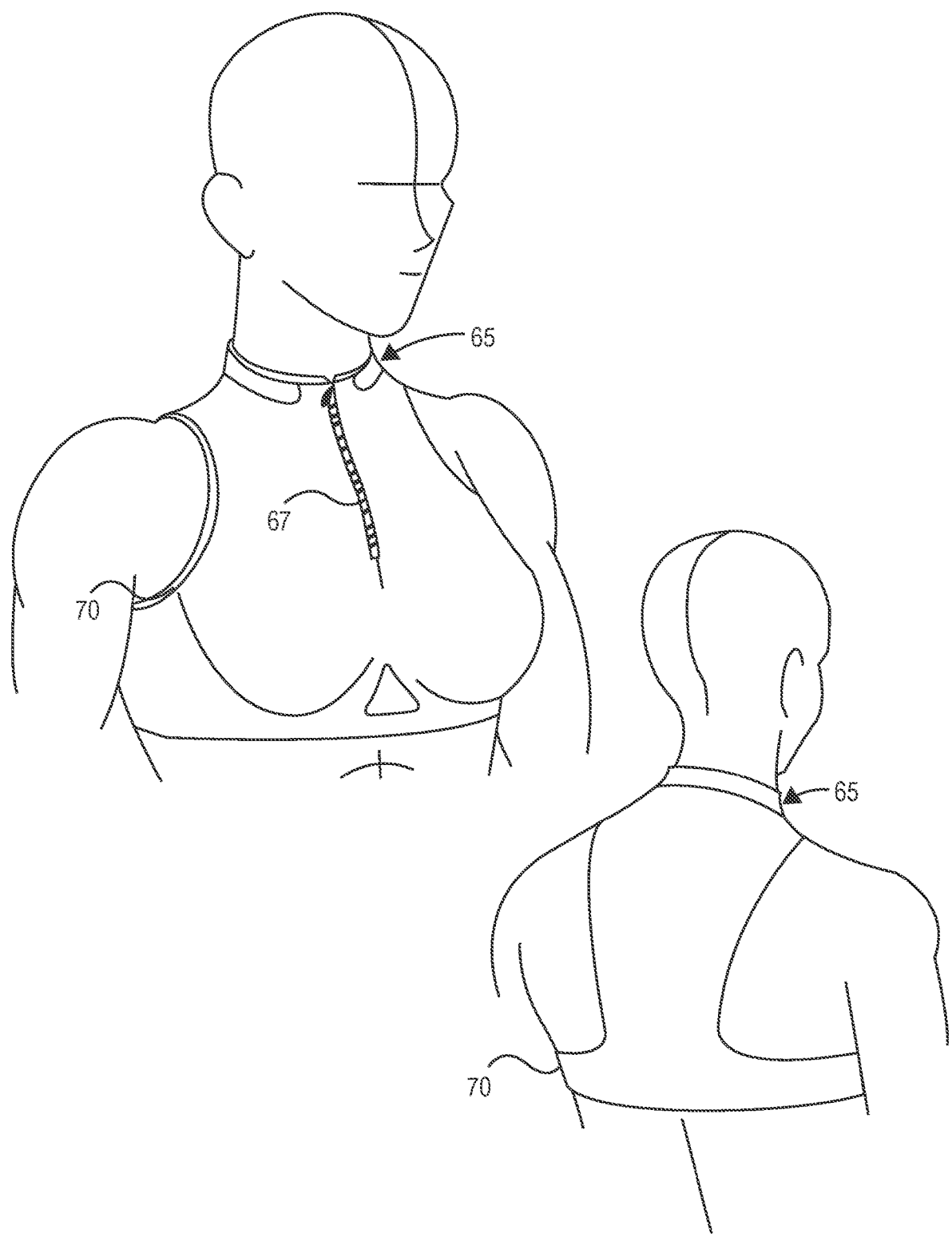
FIG. 5 is an exemplary diagram of a system embodied in a high neck sports brassier for reducing the effects of exposure to concussive events.

FIG. 5 is an exemplary diagram of a system embodied in a high neck sports bra for reducing the effects of exposure to concussive events. In the embodiment depicted in FIG. 5, the collar 65 of the sports bra 70 can employ a plurality of protuberances (not shown) applying pressure on the veins of the wearer's neck. The sports bra 70 can be constructed of different types of materials including both elastic and non-elastic fabrics. In this embodiment, elastic in the collar 65 places pressure on the protuberances located on the inside of the collar (not shown). As with other types of garments, the protuberances can be sewn into the garment. Alternatively, pockets for the protuberances can be sewn into the collar 65 of the sports bra 70. The collar 65 of the high necked sports bra 70 can be adjustable for comfort of the wearer and to vary the pressure on the veins in the neck of the wearer. The sports bra 70 can be constructed in various sizes to accommodate the physical dimensions of the wearer. In other embodiments, a collar can be inserted into a recess in the neck region of the sports bra 70 (not shown). In some embodiments, the sports bra 70 can be constructed of moisture wicking material. In some embodiments the sports bra 70 can incorporate a seam along the front of the garment. The seam 67 can be opened using a reversible closure device (e.g., zipper) to reduce pressure on the neck region of the wearer.

Figure 6:
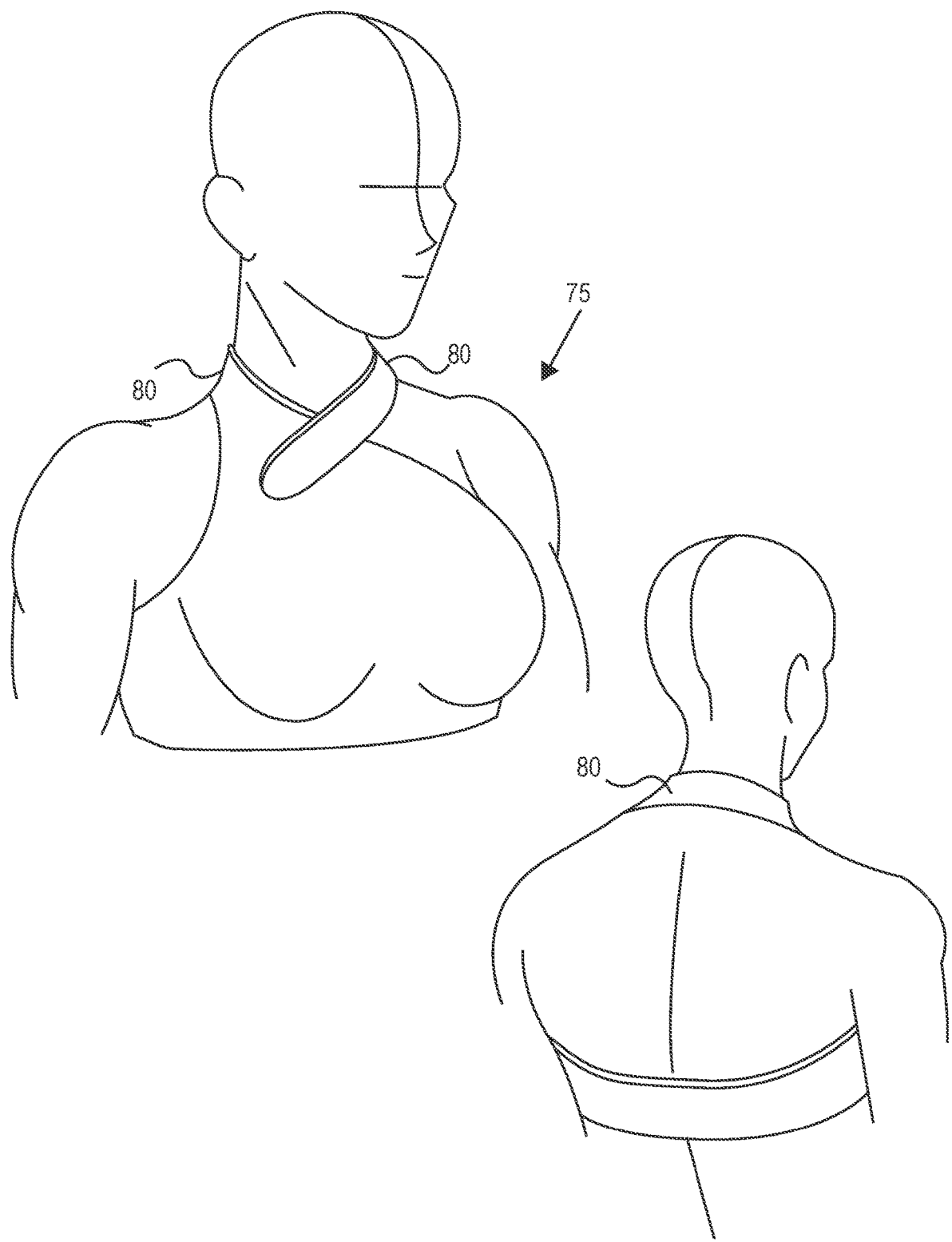
FIG. 6 is an exemplary diagram of a system embodied in a sports bra with neck straps for reducing the effects of exposure to concussive events.

FIG. 6 is an exemplary diagram of a system embodied in a sports bra with neck straps for reducing the effects of exposure to concussive events. In the embodiment depicted in FIG. 6, the sports bra 75 comprises a plurality of flaps 80 incorporated into the straps of the bra 75. The flaps 80 of the sports bra 75 can employ a plurality of protuberances (not shown) applying pressure on the veins of the wearer's neck. The flaps 80 can be positioned to place the protuberances in place over the veins in the neck of the wearer. The sports bra 75 can be constructed of different types of materials including both elastic and non-elastic fabrics. In this embodiment, elastic in the flaps 80 places pressure on the protuberances. The flaps 80 can be manufactured with elastic material to increase pressure on the neck of the wearer. The flaps 80 can comprise the ends of a continuous piece of material or can be comprised of a plurality of materials coupled together. In some embodiments, the sports bra 70 can be constructed of moisture wicking material. In the embodiment illustrated in FIG. 6, the neck strap and a lower strap encircle the wearer.

Figure 7:
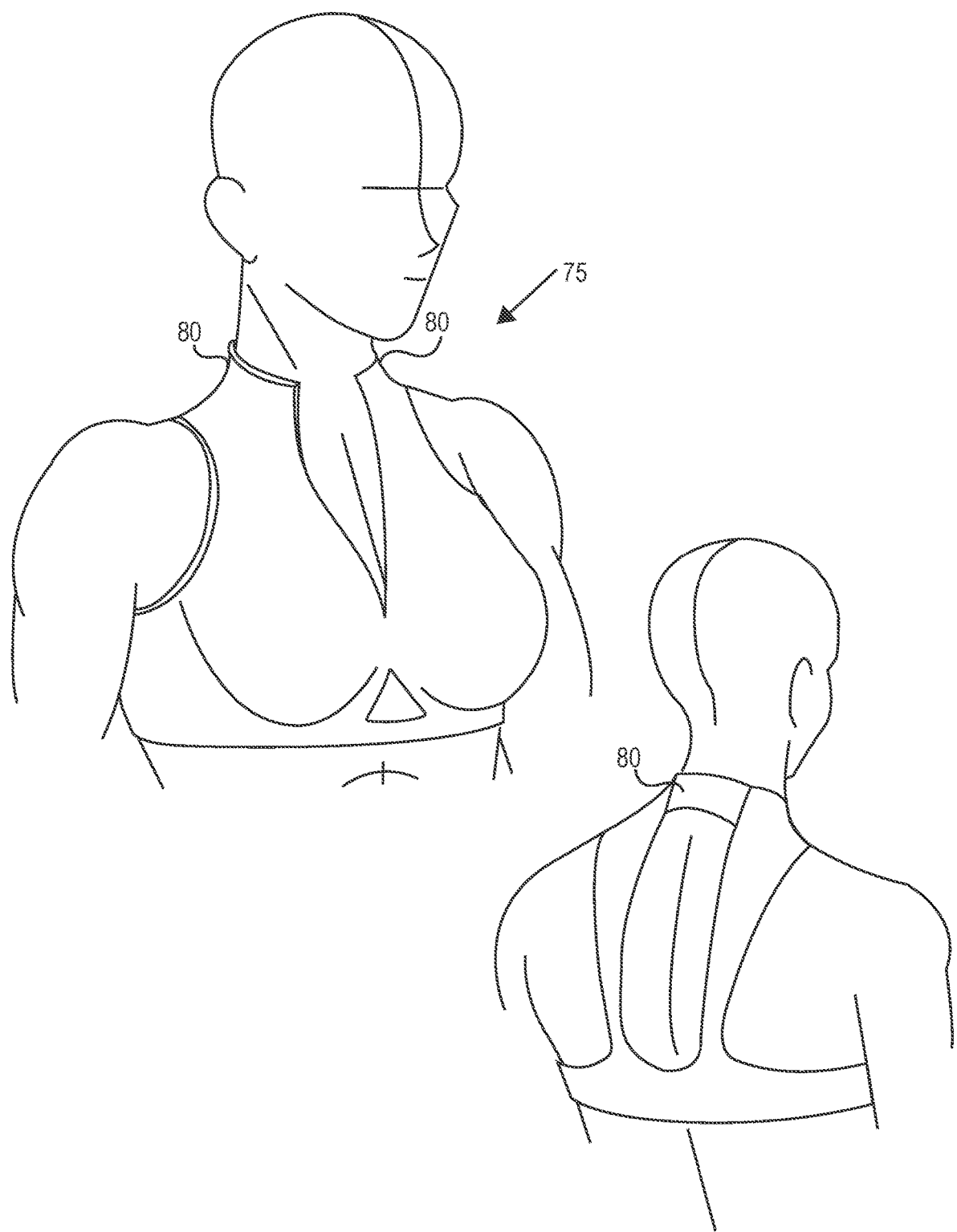
FIG. 7 is an exemplary diagram of a system embodied in a sports bra with neck straps for reducing the effects of exposure to concussive events, wherein the neck straps are unfolded.

FIG. 7 is an exemplary diagram of a system embodied in a sports bra 75 with neck straps for reducing the effects of exposure to concussive events, wherein flaps 80 are unfolded. In the embodiment depicted in FIG. 8, the flaps 80 are unfolded and rest against the neck of the wearer. The flaps can comprise a resilient material in order to apply the desired pressure. The flaps 80 can comprise a hard plastic sides on a hinge or fold in order to be moved between deployed and folded down positions. The flaps 80 can be continuous (i.e., joined around the back of the neck) or discontinuous. The flaps 80 can at least partially encircle the neck of the wearer. In the embodiment illustrated in FIG. 7, the sports bra 75 comprises two vertical straps along the back of the wearer.

Figure 8:
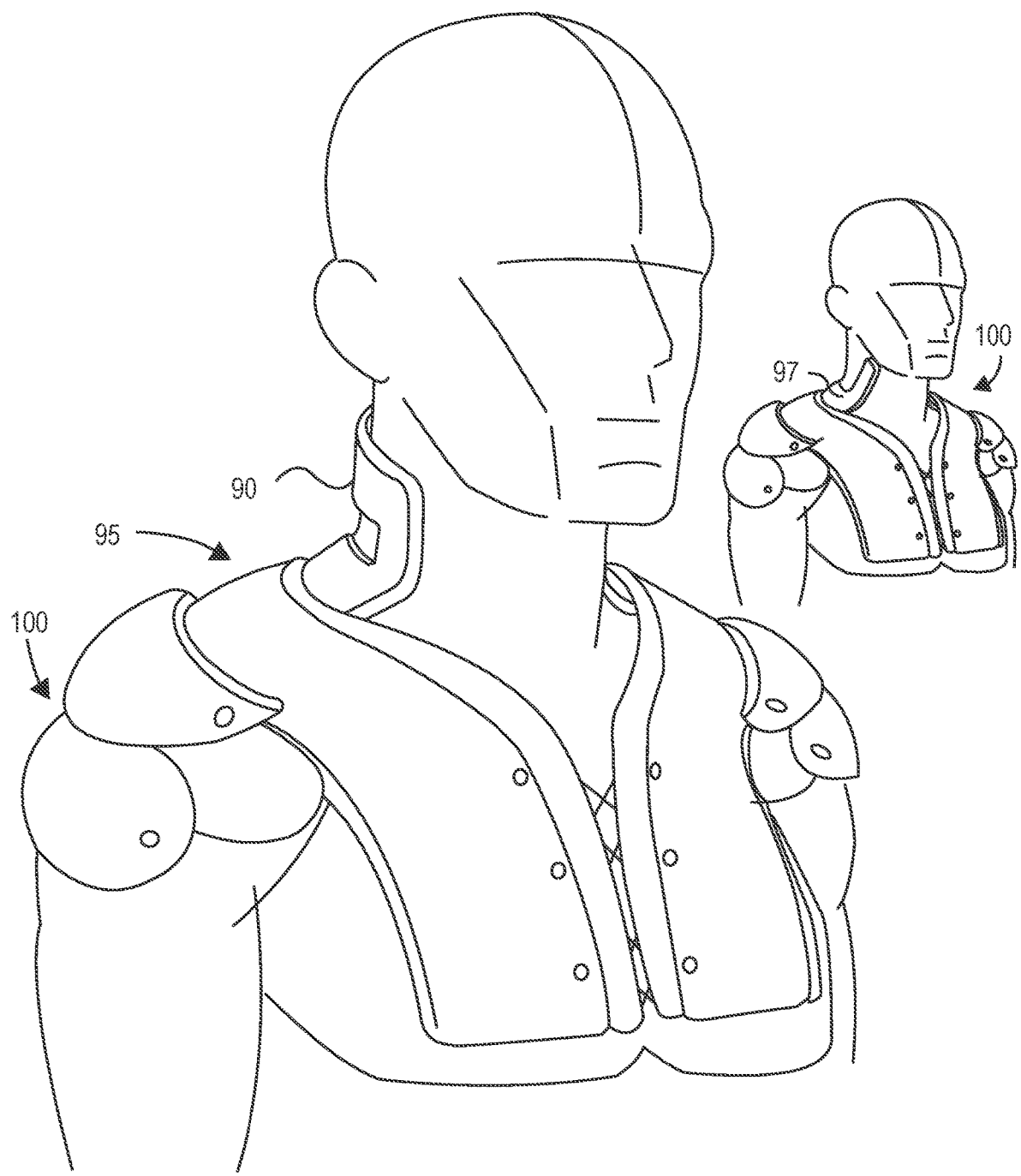
FIG. 8 is an exemplary diagram of a system embodied in an integrated shoulder pad assembly for reducing the effects of exposure to concussive events.

FIG. 8 is an exemplary diagram of a system embodied in an integrated shoulder pad assembly for reducing the effects of exposure to concussive events. In the embodiment depicted in FIG. 8, a collar assembly 95 can be coupled with a shoulder pad assembly 100 in any conventional manner such as through the use of fasteners. The collar 90 depicted in FIG. 8 can be disposed about at least a portion of the wearer's neck. The collar 90 can comprise a longitudinal axis that wraps at least partially (i.e., partially or completely) about the wearer's neck. For instance, in this embodiment, the collar 90 extends about at least a majority of a circumference of the wearer's neck. For example, in this embodiment, the collar 90 can extend about at least two-thirds of the circumference of the wearer's neck, in some cases at least three-quarters of the circumference of the wearer's neck, in some cases at least four-fifths of the circumference of the wearer's neck, and in some case even more (e.g., an entirety of the circumference of the wearer's neck).

Although the collar 90 is show in FIG. 8 as being attached the collar assembly at the end regions of the collar, coupling can occur along any point on the collar 90. The collar assembly 95 can be removably coupled or permanently affixed to the shoulder pad assembly 100. The collar 90 can incorporate protuberances (not shown) on the inside surface of the collar 90. In one embodiment, the protuberances (not shown) are relatively large such that continuous neck vein pressure is applied when the neck is rotated from side to side within the collar. In some embodiments, the protuberances are adjustable to vary the pressure on the veins of the neck of a wearer. In some embodiments, extensions 97 are coupled with the shoulder pad assembly 100. In some embodiments, protuberances (not shown) can be formed on the inside surface of the extensions 97 to apply pressure to the veins of the neck of a wearer. In some embodiments, the extensions 97 can be adjustable to properly position the protuberances over the veins of the neck.

Figure 9:
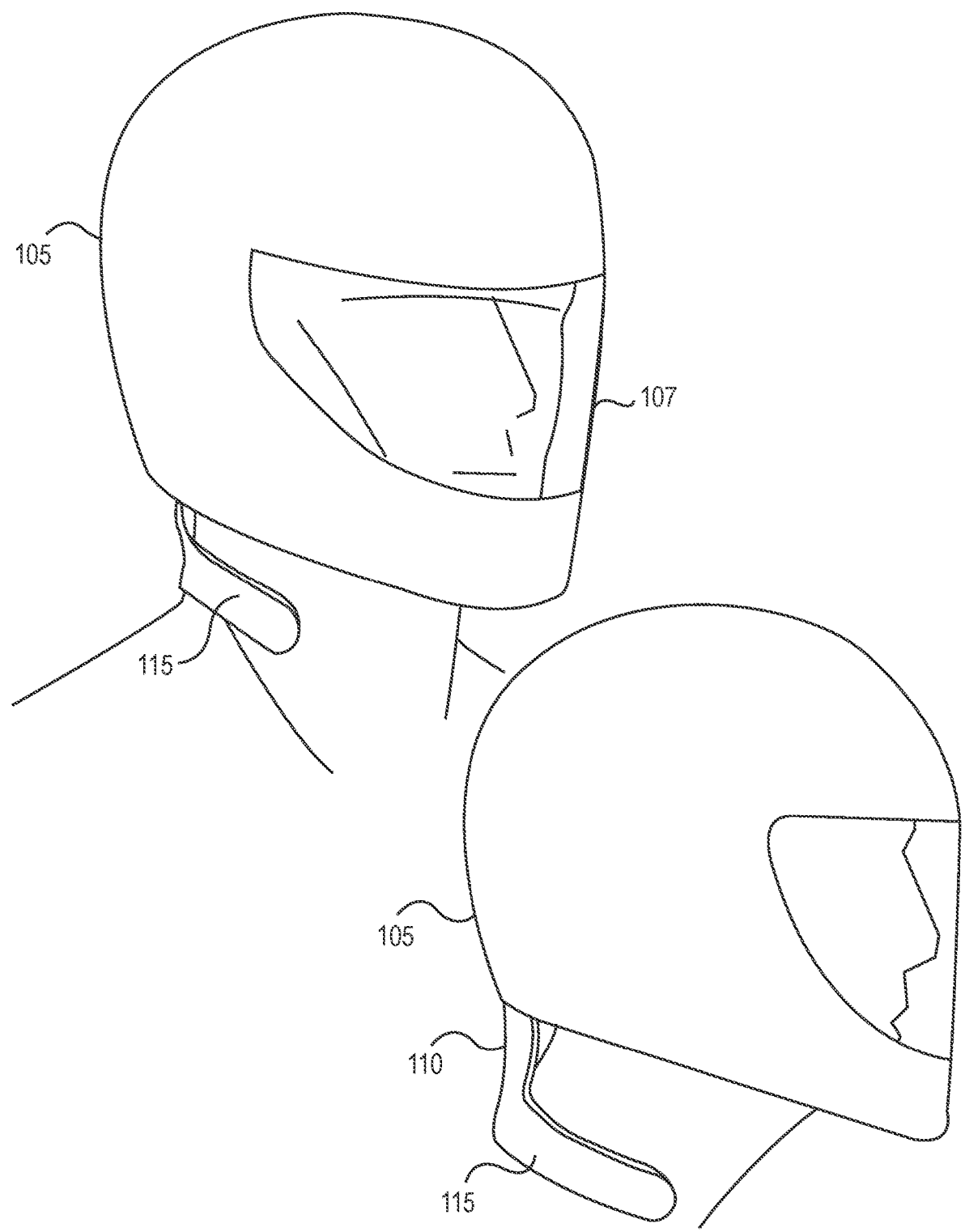
FIG. 9 is an exemplary diagram of a system embodied as part of a helmet for reducing the effects of exposure to concussive events.

FIG. 9 is an exemplary diagram of a system embodied as part of a helmet for reducing the effects of exposure to concussive events. The helmet 105 can include a face shield 107 or include a full-face design. In the embodiment depicted in FIG. 9, a single vertical extension 110 couples the collar 115 to a base of the helmet 105. In an alternate configuration, the collar 115 may be coupled to the helmet 105 by two, three, four, or more extensions 110 which typically will be placed symmetrically around the collar 115.

The collar 115 can employ a plurality of protuberances (not shown) on the inside surface of the collar 115. The protuberances (not shown) can apply pressure on the veins of the wearer's neck. In some embodiments of the helmet design depicted in FIG. 9, the extension 110 can be removably coupled to the helmet 105. In other embodiments, the collar 115 can be removably coupled to the extension 110. In other embodiments, both the extension 110 can be removably coupled to the helmet 105 and the collar 115 can be removable coupled to the extension 110. In some embodiments, the extension 110 is adjustable in length to allow for proper placement of the collar 115.

Figure 10:
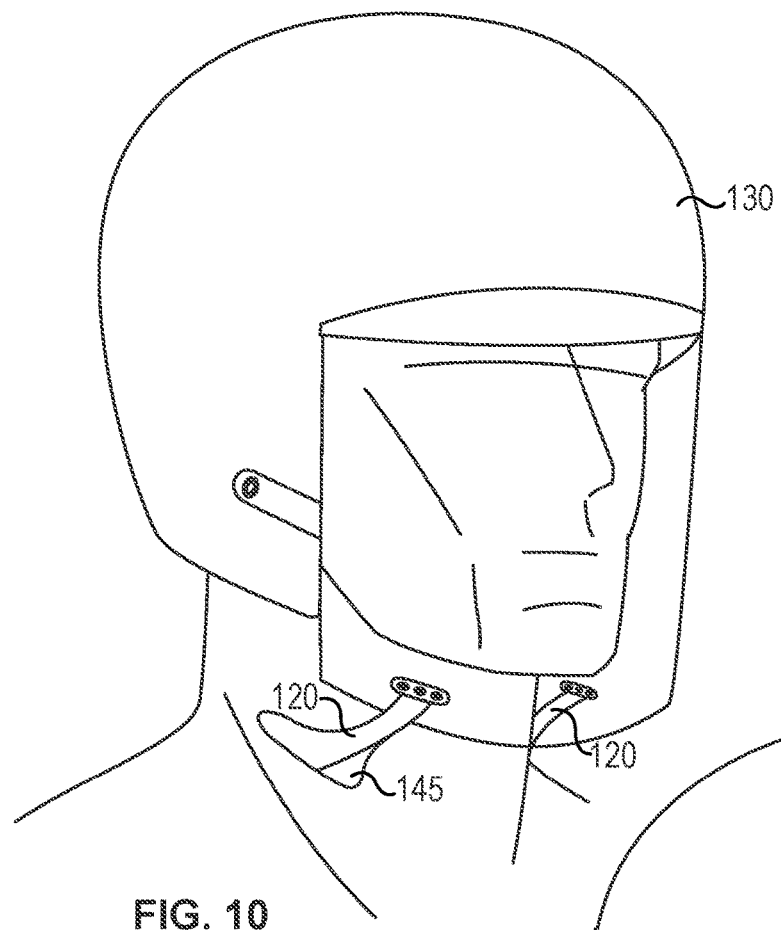
FIG. 10 is an exemplary diagram of a system embodied as part of a protective face shield for reducing the effects of exposure to concussive events.

FIG. 10 is an exemplary diagram of a system embodied as part of a protective face shield 125 for reducing the effects of exposure to concussive events. In the embodiment depicted in FIG. 10, a concussion protective device 120 can be coupled to the protective face shield 125 of a helmet 130. The concussion protective device 120 can comprise an extension 135 comprising proximal and distal end regions. The proximal end region 140 can couple to the face shield 125 in any conventional manner. The distal end region 145 can have a protuberance (not show) to apply pressure on the veins of the wearer's neck. In some embodiments, the extension 135 can be adjusted for fit of the wearer. Although FIG. 10 illustrates this embodiment as having a full and transparent face shield (e.g., make of a plastic), it is understood that the device may be adapted to any style of face shield including, for example, those with bars such as a standard football helmets. The protective shield assembly can be used in sports requiring a full-face shield such as skiing, football, hockey or lacrosse. Further, the design can be employed by law enforcement officers using a full-face shield design. The protective device 120 may be removably or permanently attached to the face shield 125.

Figure 11:
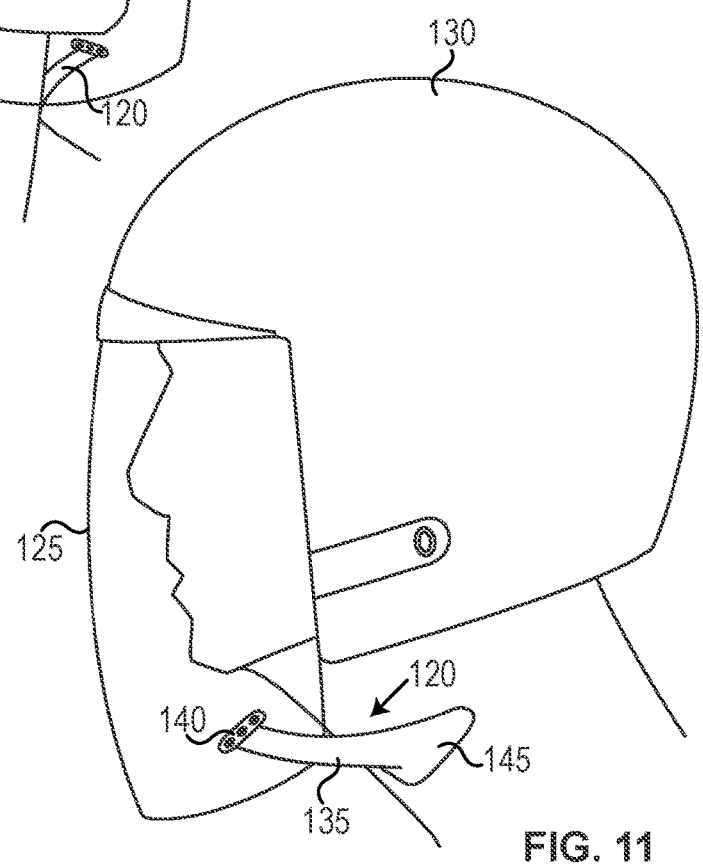
FIG. 11 is a front view of the system of FIG. 10.

FIG. 11 is a side view of the system of FIG. 10. As shown in FIG. 11, the protective shield can have a plurality of concussion protective devices 120 coupled to the protective face shield 125 of a helmet 130. In some embodiments, the extensions 135 can be adjusted for fit of the wearer.

Figure 12:
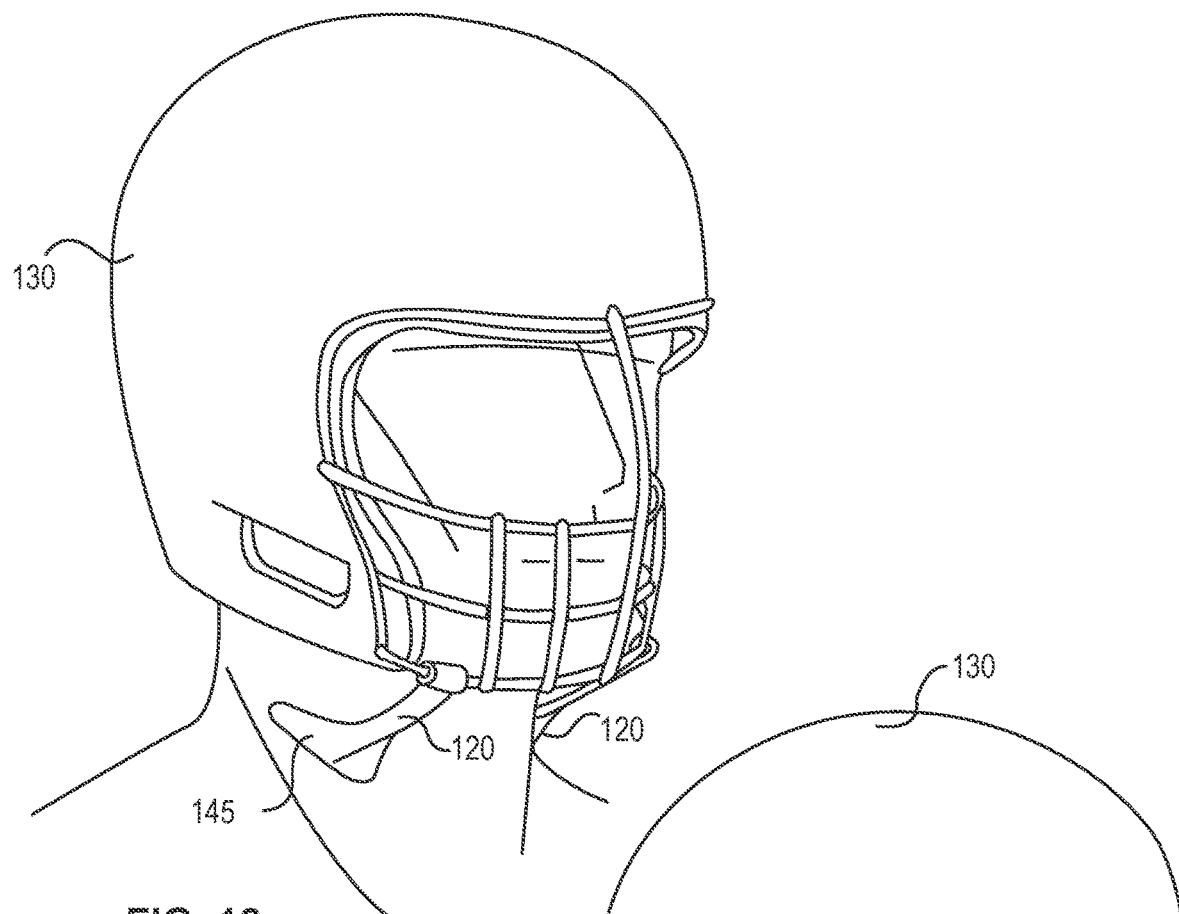
FIG. 12 is an embodiment of the system of FIG. 10 incorporated into a football helmet.
Figure 13:
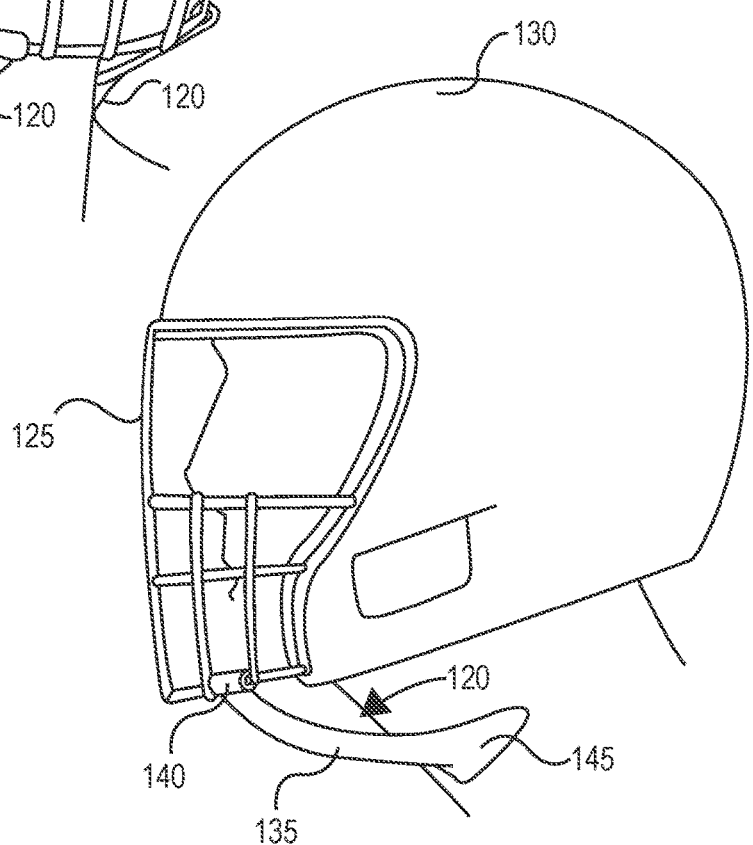
FIG. 13 illustrates a profile view of the system of FIG. 12.

FIG. 12 is a front view of an embodiment of the system of FIG. 10. In FIG. 12, the helmet 130 can be standard football helmet. In this embodiment, extensions 120 can be removably coupled to the front grill of the helmet 130 at the proximal end region 140 of the extension 120. The distal end region 145 of the extension 120 can be position over the veins in the neck of the wearer. Protuberances (not shown) can be coupled on the inside surface of the extensions 120 and apply pressure to the veins of the wearer's neck. In some embodiments, the extensions 120 can be adjustable for proper fit and comfort of the wearer. FIG. 13, depicts a profile view of the system of FIG. 12.

Figure 14:
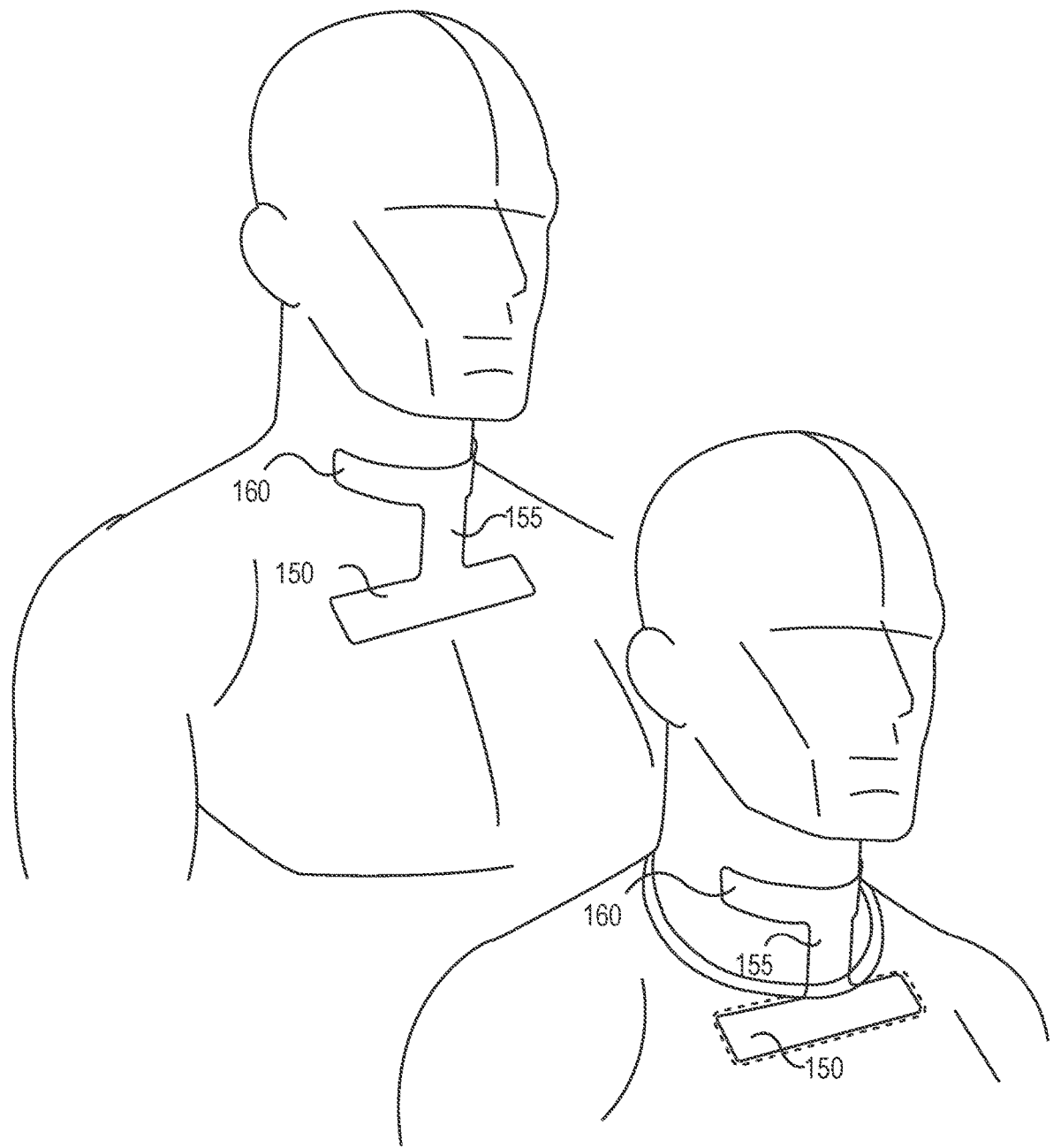
FIG. 14 is an exemplary diagram of a system extending from an anchoring point for reducing the effects of exposure to concussive events.

FIG. 14 is an exemplary diagram of a system extending from an anchoring point for reducing the effects of exposure to concussive events. In the embodiment shown in FIG. 14, a protective collar 160 can be coupled to an extension 155. The extension 155 can be coupled to an anchoring point 150. The anchoring point 150 can be attached to a garment or other equipment worn by a user. In some embodiments of the anchoring point design depicted in FIG. 14, the extension 155 can be removably coupled to the anchoring point 150. In other embodiments, the collar 160 can be removably coupled to the extension 155. In other embodiments, both the extension 155 can be removably coupled to the anchoring point 150 and the collar 160 can be removable coupled to the extension 155. In some embodiments, the extension 155 is adjustable in length to allow for proper placement of the collar 160. The collar 160 can employ a plurality of protuberances (not shown) applying pressure on the veins of the wearer's neck. In some embodiments, the extension 155 can be manufactured from a flexible plastic material to allow the head of the wearer to turn. In another embodiment, the extension 155 is positioned along the back (rather than the front) of the subject's neck and the collar 160 is open at the laryngeal prominence.

Figure 15:
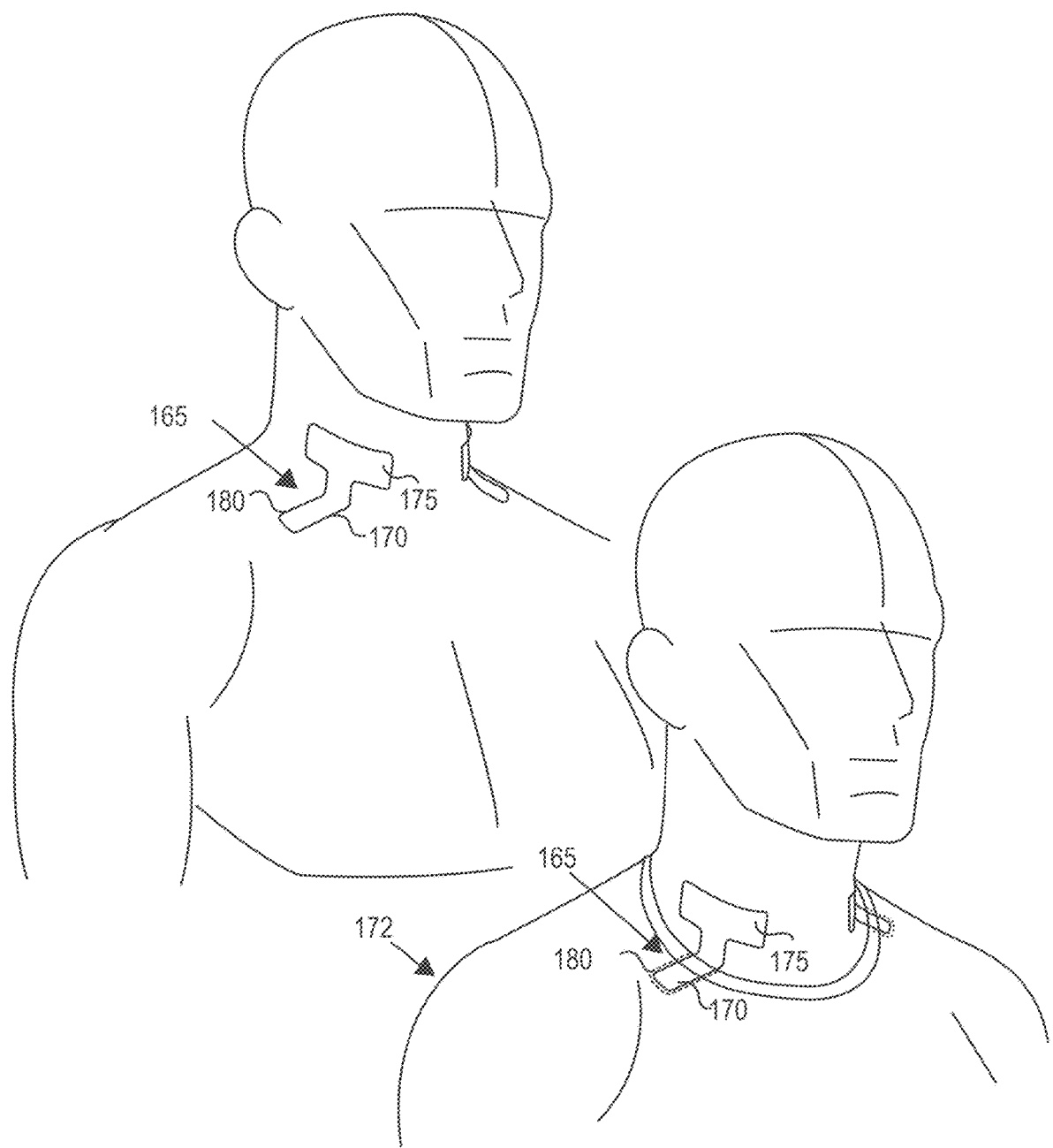
FIG. 15 is an exemplary diagram of a non-circumferential system extending from an anchoring point for reducing the effects of exposure to concussive events.

FIG. 15 is an exemplary diagram of a non-circumferential system extending from an anchoring point for reducing the effects of exposure to concussive events. In the embodiment shown in FIG. 15, a plurality of concussion protective devices 165 can be coupled with a garment. In one embodiment, the concussive protective device 165 can comprise of an extension 170 with a distal and proximal end regions. The proximal end region 175 can include protuberances (not shown) for applying pressure on the veins of the wearer's neck. The distal end region 180 can couple with an anchor point on a garment 172 or other equipment to be worn by a person. In some embodiments, the distal end region 180 can removably couple with an anchor point on the garment 172. As shown in FIG. 15, a pair of concussive protective devices 165 can be employed on each side of a wearer's neck. In some embodiments, the extension 170 can be adjustable to accommodate proper placement of the device for wearers with different dimensions.

Figure 16:
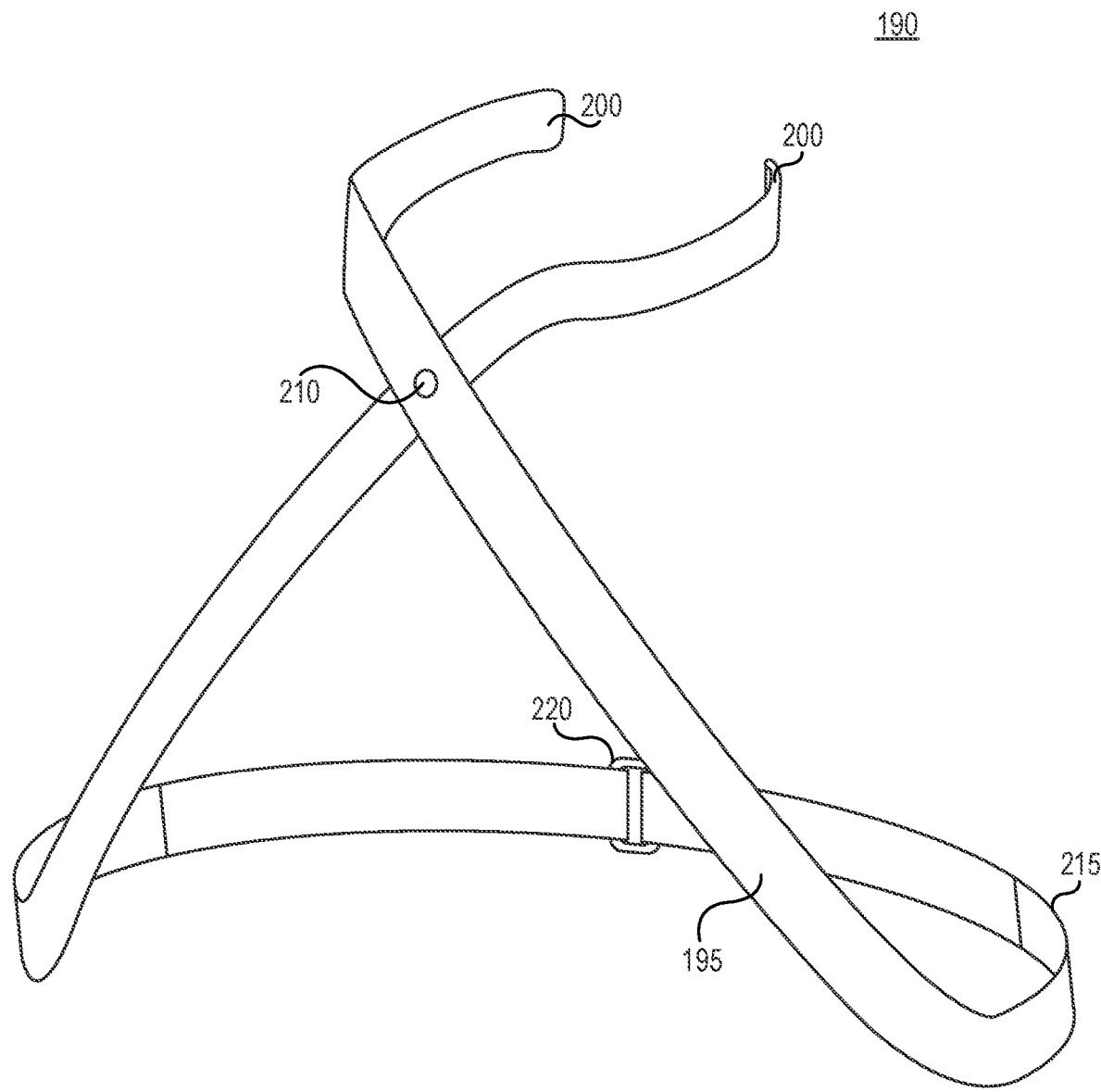
FIG. 16 is an exemplary diagram of a system embodied in an adjustable harness for reducing the effects of exposure to concussive events.

FIG. 16 is an exemplary diagram of a system embodied in an adjustable harness for reducing the effects of exposure to concussive events. In one embodiment, the adjustable harness 190 can comprise a single strap 195 constructed of elastic materials, inelastic materials, or a combination of both. The end regions of the strap 195 can comprise engagement regions 200 for applying pressure on each side of a wearer's neck when the adjustable harness 190 is worn. In some embodiments, engagement regions 200 can include protuberances (not shown) for applying pressure on the veins of the wearer's neck. The strap 195 can be adjustable through an adjustment mechanism 215 located on the strap. The adjustment mechanism 215 can lengthen or shorten the strap 195 in any conventional manner to accommodate a size of the wearer. In some embodiments, the strap 195, can cross over and couple at an attachment point 210. In some embodiments of the harness of FIG. 16, adjusting the strap 195 provides the force that is applied to the veins in the neck of the wearer. In other embodiments, the elastic material in the strap 195 provides the force that is applied to the veins in the neck of the wearer. In some embodiments of harness 190, attachment point 210 is located on the back of the device such that it positioned against the user's back. In other embodiments, attachment point 210 is positioned in the front. In yet other embodiments, harness 190 has two attachment points 210, one in the front and one in the back.

Figure 17:
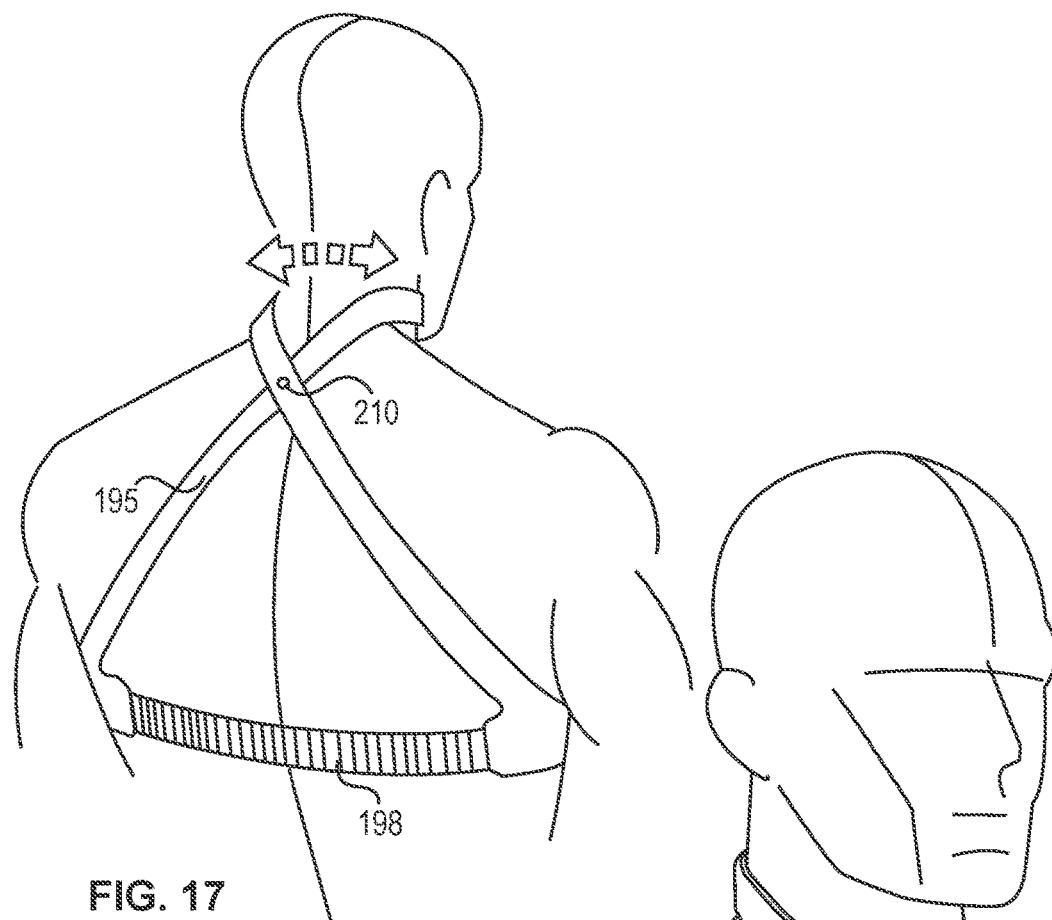
FIG. 17 is a back view of the exemplary system of FIG. 16 being worn by a person.

FIG. 17 is a back view of the exemplary system of FIG. 16 as worn by a person. In some embodiments, the location of the attachment point 210 can be adjusted to accommodate the size of a wearer. In some embodiments, the horizontal strap 198 can comprise an elastic material.

Figure 18:
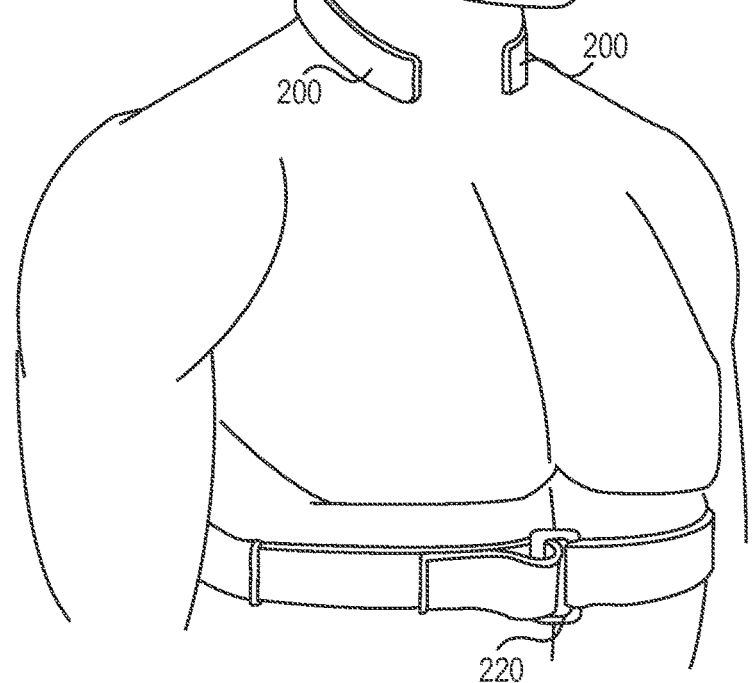
FIG. 18 is a front view of the exemplary system of FIG. 16 being worn by a person.

FIG. 18 is a front view of the exemplary system of FIG. 16, being worn by a person. As shown in FIG. 18, the engagement regions 200 are in place over the neck region of a person. In the embodiment, a coupling mechanism 220 such as a conventional coupling device (e.g., a buckle) can be used to removably couple the two sections of the strap 195 together.

Figure 19:
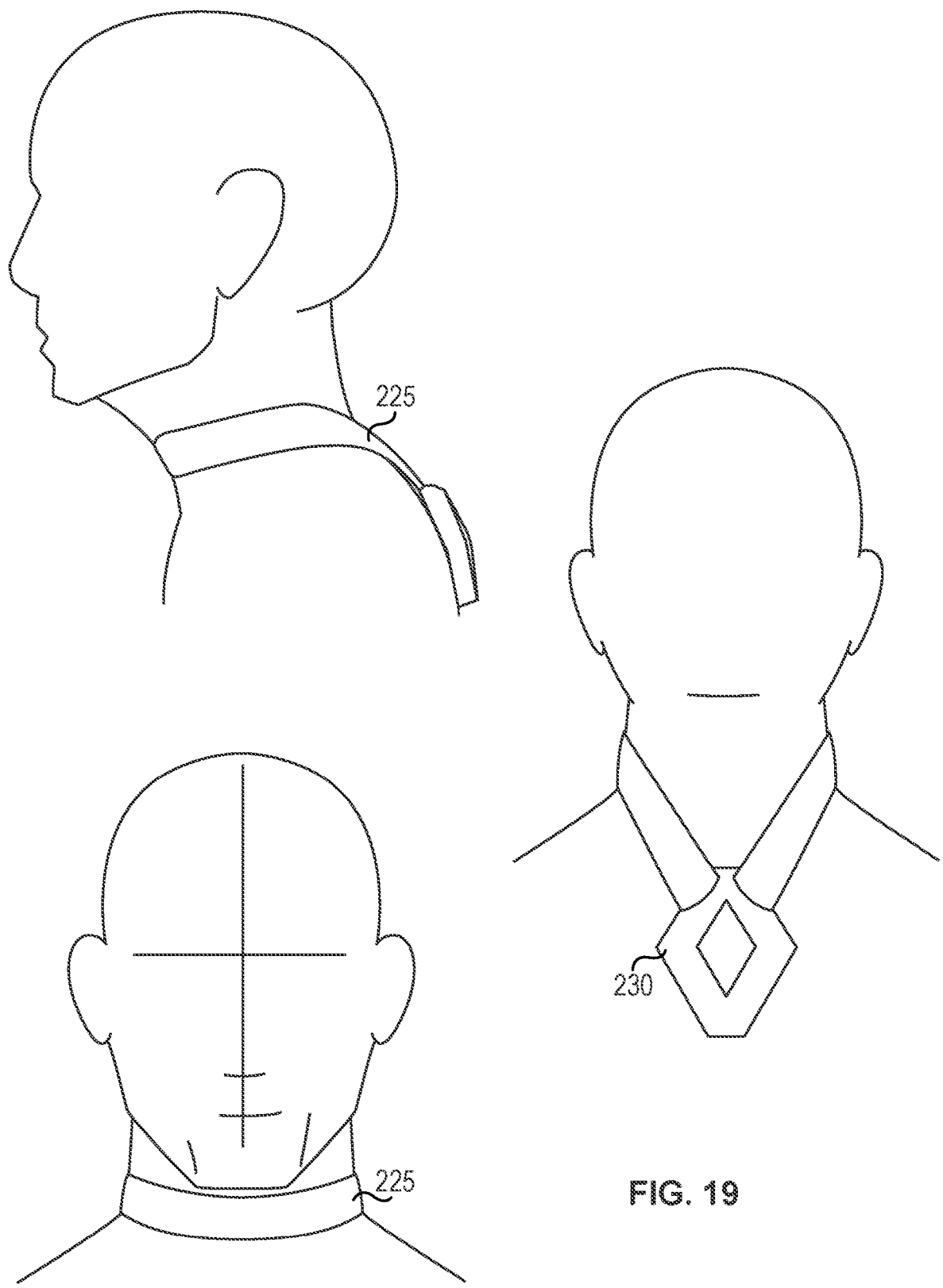
FIG. 19 is an exemplary diagram of a system embodied in a weighted reverse collar system for reducing the effects of exposure to concussive events.

FIG. 19 is an exemplary diagram of a system embodied in a weighted reverse collar system for reducing the effects of exposure to concussive events. In the embodiment depicted in FIG. 19, a strap 225 can be attached to a weighted coupling device 230. The strap 225 can be constructed of a plurality of elastic and inelastic materials. The side of the strap 225 closest to a body of a wearer can comprise engagement regions for applying pressure on each side of a wearer's neck when the weighted reverse collar is worn. In some embodiments, the inside of the strap 225 can include protuberances (not shown) for applying pressure on the veins of the wearer's neck. In some embodiments, the length of the strap 225 can be adjusted to accommodate the size of the wearer. The weighted coupling device 230 has the appropriate mass to apply the desired pressure to the neck veins consistent with the construction of the remainder of the device. The weighted coupling device can weigh about 0.25, 0.5, 0.75, 1.0, 1.5, 2.0, 2.5, 3.0 pounds or more.

Figure 20:
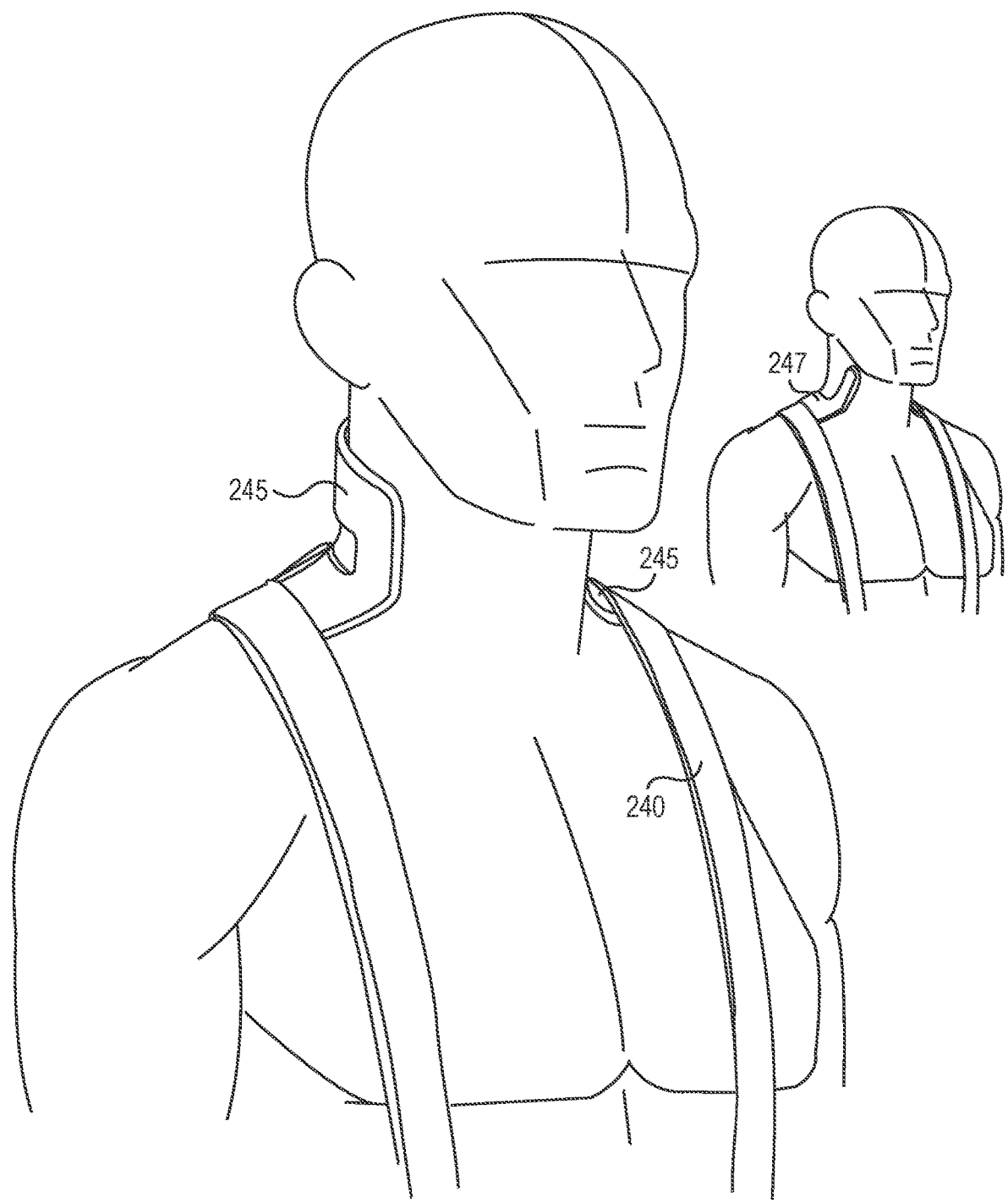
FIG. 20 is an exemplary diagram of a system embodied in suspenders for reducing the effects of exposure to concussive events.

FIG. 20 is an exemplary diagram of a system embodied in suspenders for reducing the effects of exposure to concussive events. In the embodiment show in FIG. 20, a concussion protective device 245 can be coupled to suspenders 240. In one embodiment, the concussion protective device 245 can include protuberances (not shown) for applying pressure on the veins of the wearer's neck. In some embodiments, the elastic in the suspenders can apply the force on the concussion protective device 245 to apply pressure on the veins of the wearer's neck. In some embodiments, extensions 247 can be coupled to the suspenders 240. In some embodiments, the concussion protective device 245 can be coupled to the straps of a backpack (not shown).

Figure 21:
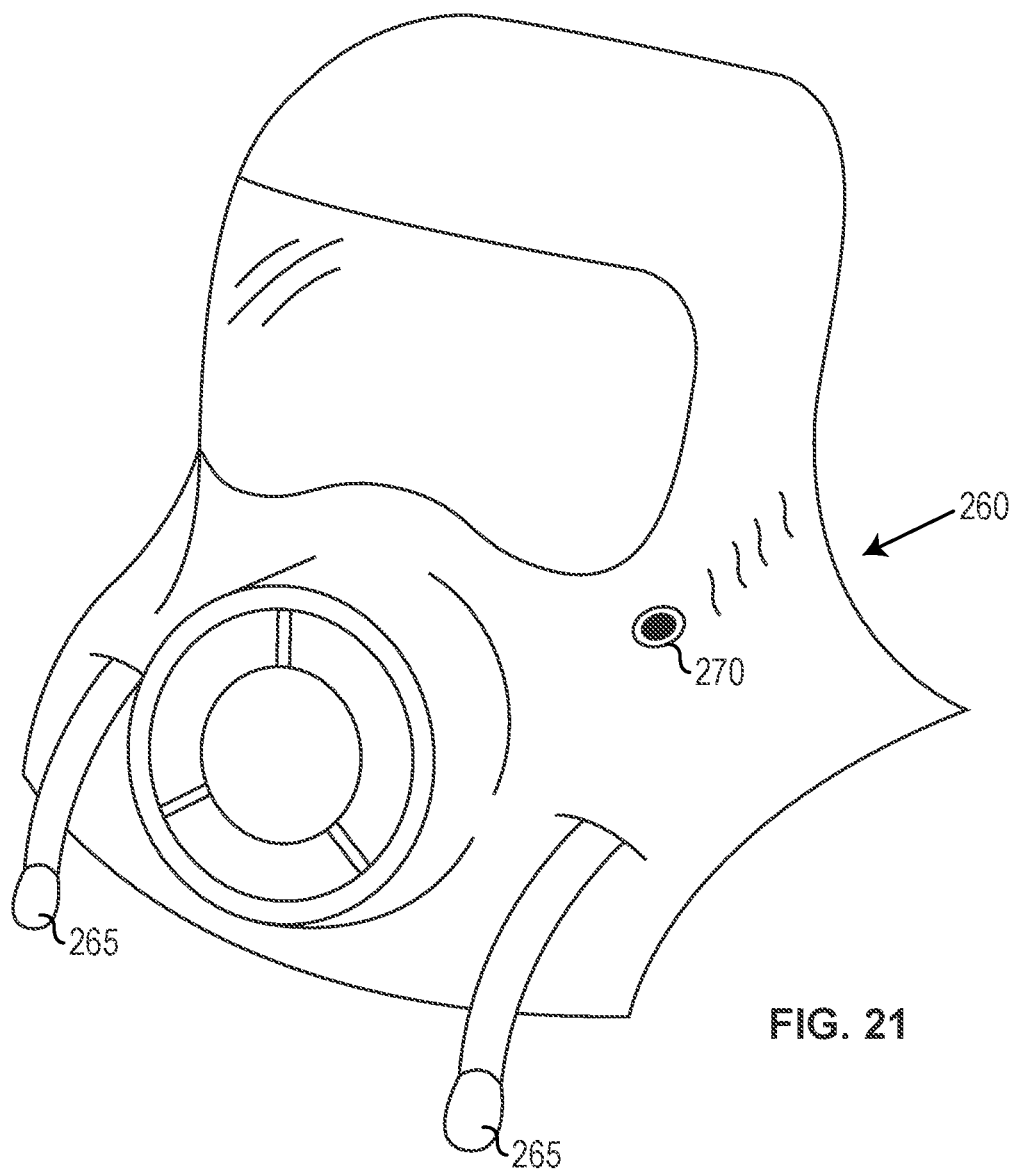
FIG. 21 is an exemplary diagram of a system embodied in a gas mask for reducing the effects of exposure to concussive events.

FIG. 21 is an exemplary diagram of a system embodied in a gas mask for reducing the effects of exposure to concussive events. In the system depicted in FIG. 21, a gas mask can be modified to incorporate features to reduce the effects of exposure to concussive effects. Pull strings 265 can be attached to an engagement region 270 of the gas mask 260. The engagement region 270 can be positioned over the veins in the neck of the wearer of the gas mask. Pulling the strings 265 downward away from the face can add pressure to the engagement region 270 of the gas mask 260. In some embodiments, engagement regions 200 can include protuberances (not shown) for applying pressure on the veins of the wearer's neck. In some embodiments, the strings 265 can be released to relieve the pressure on the engagement region 270.

Figure 22:
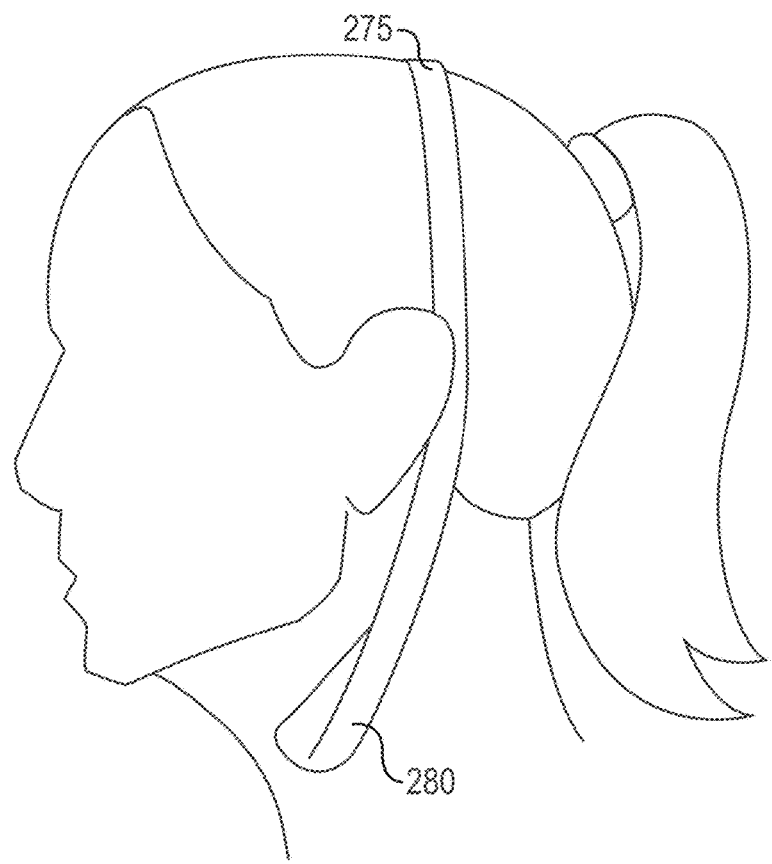
FIG. 22 is an exemplary diagram of a system embodied in a hair band for reducing the effects of exposure to concussive events.
Figure 22:
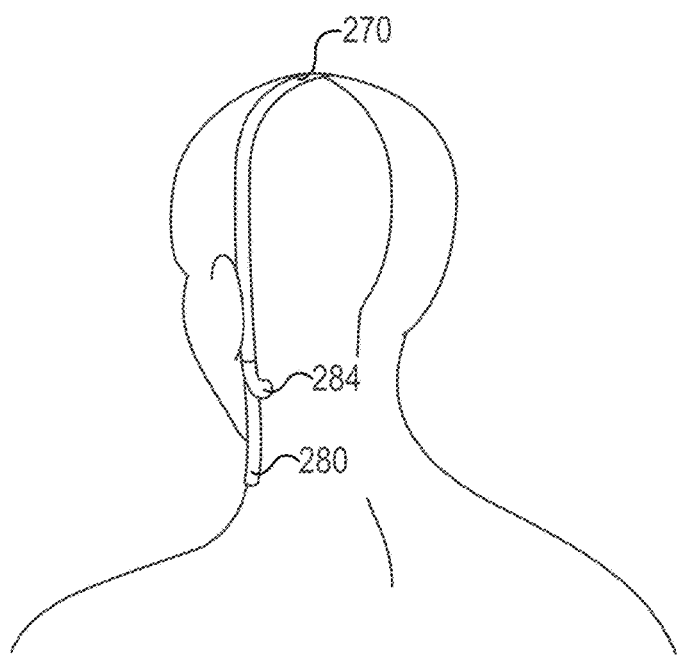

FIG. 22 is an exemplary diagram of a system embodied in a hair band for reducing the effects of exposure to concussive events. In the embodiment shown in FIG. 22, the hair band 275 can have engagement regions 280 at the distal end regions of the hairband. The inherent elasticity of the hair band 275 can apply pressure on the veins of the wearer's neck. In some embodiments, the hair band 275 can have a third leg 284 to stabilize the band on the head of a wearer. The third leg 284 may be discontinuous with one positioned on each side of the hair band 275 and extending around the back of the head. Alternatively, the third leg 284 may be continuous, thereby forming a second band to the hair band 275. The hair band 275 embodiment may be useful in women's sports such as cheerleading. The hair band 275 can be manufactured in various styles, colors, widths to meet the desires of consumers.

Figure 23A:
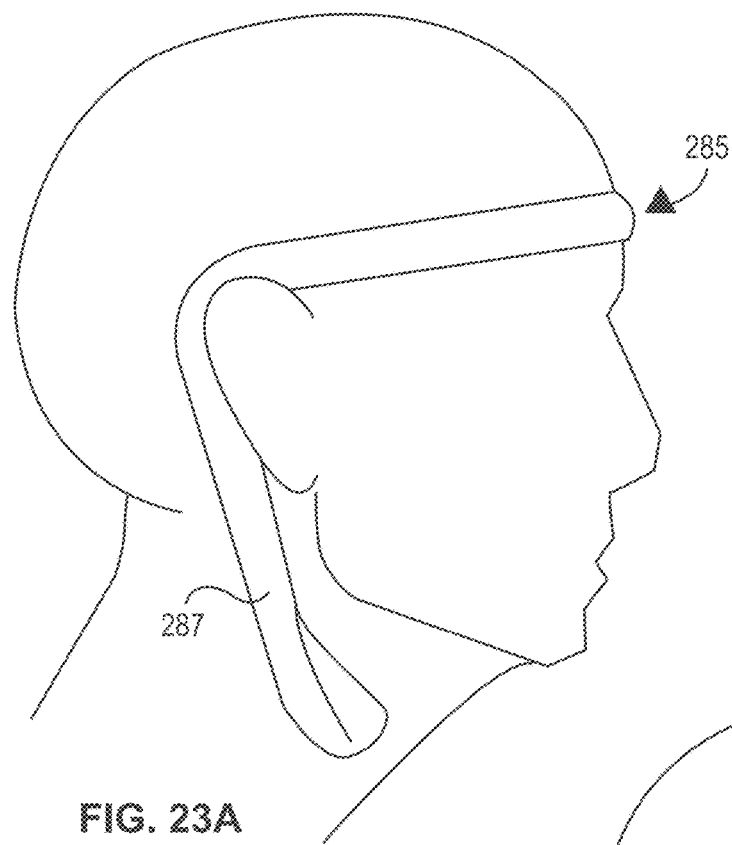
FIG. 23A is an exemplary diagram of a system embodied in a head band for reducing the effects of exposure to concussive events.
Figure 23B:
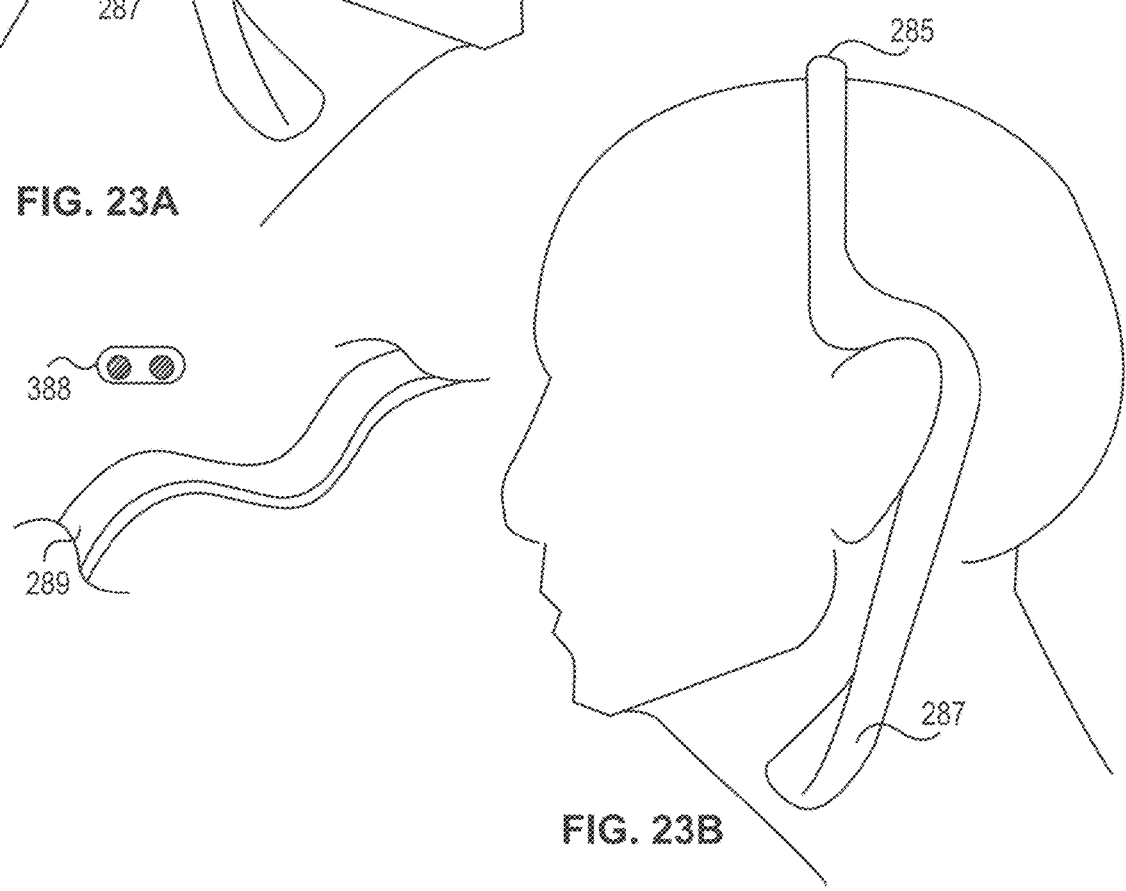
FIG. 23B is another exemplary diagram of a system embodied in a head band for reducing the effects of exposure to concussive events.

FIG. 23A is an exemplary diagram of a system embodied in a head band for reducing the effects of exposure to concussive events and/or damage to the inner ear caused by loud sounds (e.g., music) or blast waves. FIG. 23A illustrates an embodiment of head band 285 configured to rest on the forehead of the wearer. FIG. 23B illustrates an embodiment of the head band that rests on the top of the head of the wearer. In the embodiment shown in FIG. 23, a plurality of extensions 287 can be coupled with a head band 285. The head band can be worn to keep the extensions 287 properly positions over the veins of the neck of a person. In some embodiments, the headband can be constructed of a flexible, "Gumby-like" material that retains the deformed shape. Such materials can include shape-memory metal alloys encases in a rubberized coating. The inherent flexible design can be seen in the head band section 289. In some embodiments, the extensions can include protuberances 388 for applying pressure on the veins of the wearer's neck.

Figure 23C:
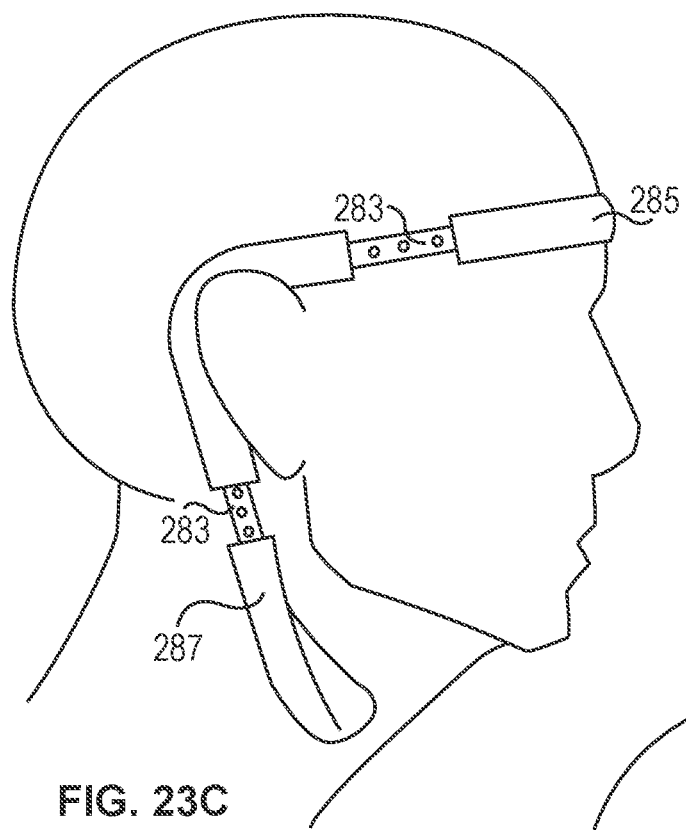
FIG. 23C is an exemplary diagram of an adjustable system embodied in a head band for reducing the effects of exposure to concussive events.
Figure 23D:
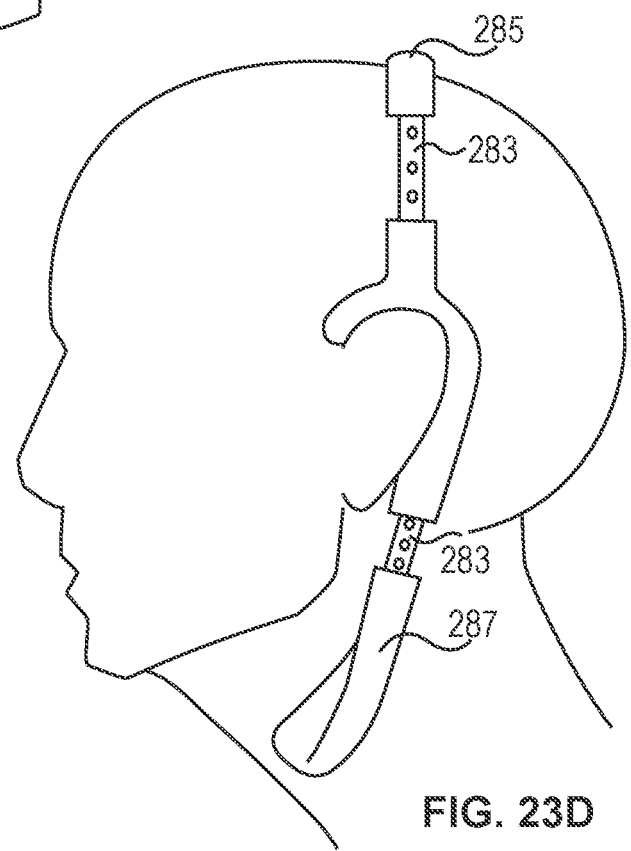
FIG. 23D is another exemplary diagram of an adjustable system embodied in a head band for reducing the effects of exposure to concussive events.

FIG. 23C illustrates an embodiment of the head band 285 of FIG. 23A in which the length of the head band can be adjusted through at least one adjustment mechanism 283. The adjustment mechanism can comprise any conventional device to increase or decrease the length of the head band 285. In FIG. 23C the adjustment mechanism 283 comprises a slidable bar. FIG. 23D illustrates an embodiment of the head band 285 of FIG. 23B in which the length of the head band can be adjusted through at least one adjustment mechanism 283. The adjustment mechanism can comprise any conventional device to increase or decrease the length of the head band 285. In FIG. 23D the adjustment mechanism 283 comprises a slidable bar.

Figure 24:
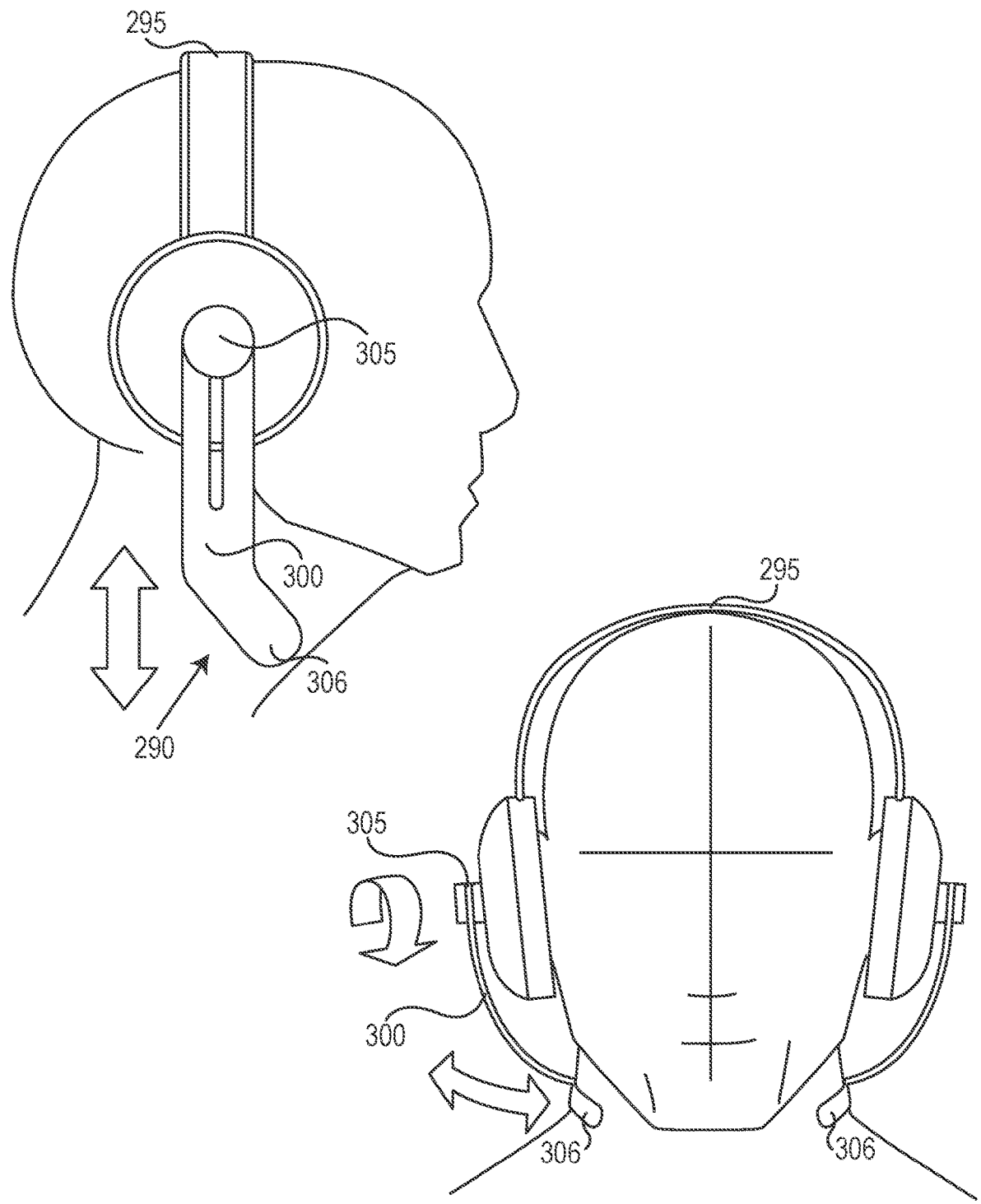
FIG. 24 is an exemplary diagram of a system embodied in head phones for reducing the effects of exposure to concussive events.

FIG. 24 is an exemplary diagram of a system embodied in head phones for reducing the effects of exposure to concussive events and/or damage to the inner ear caused by loud sounds (e.g., music) or blast waves. In the embodiment shown in FIG. 24, headphones 295 can include a concussion prevention device 290. The concussion prevention device 290 can be coupled to the headphones 295 with a pressure arm 300 extending from the headphones. In some embodiments, the headphones 295 can include a dial 305 to rotate the pressure arm 300 into position over the vein of a wearer's neck. The pressure arm 300 can have an engagement region 306 at the distal end of the pressure arm 300. In some embodiments, the extensions can include protuberances (not shown) for applying pressure on the veins of the wearer's neck.

Figure 25:
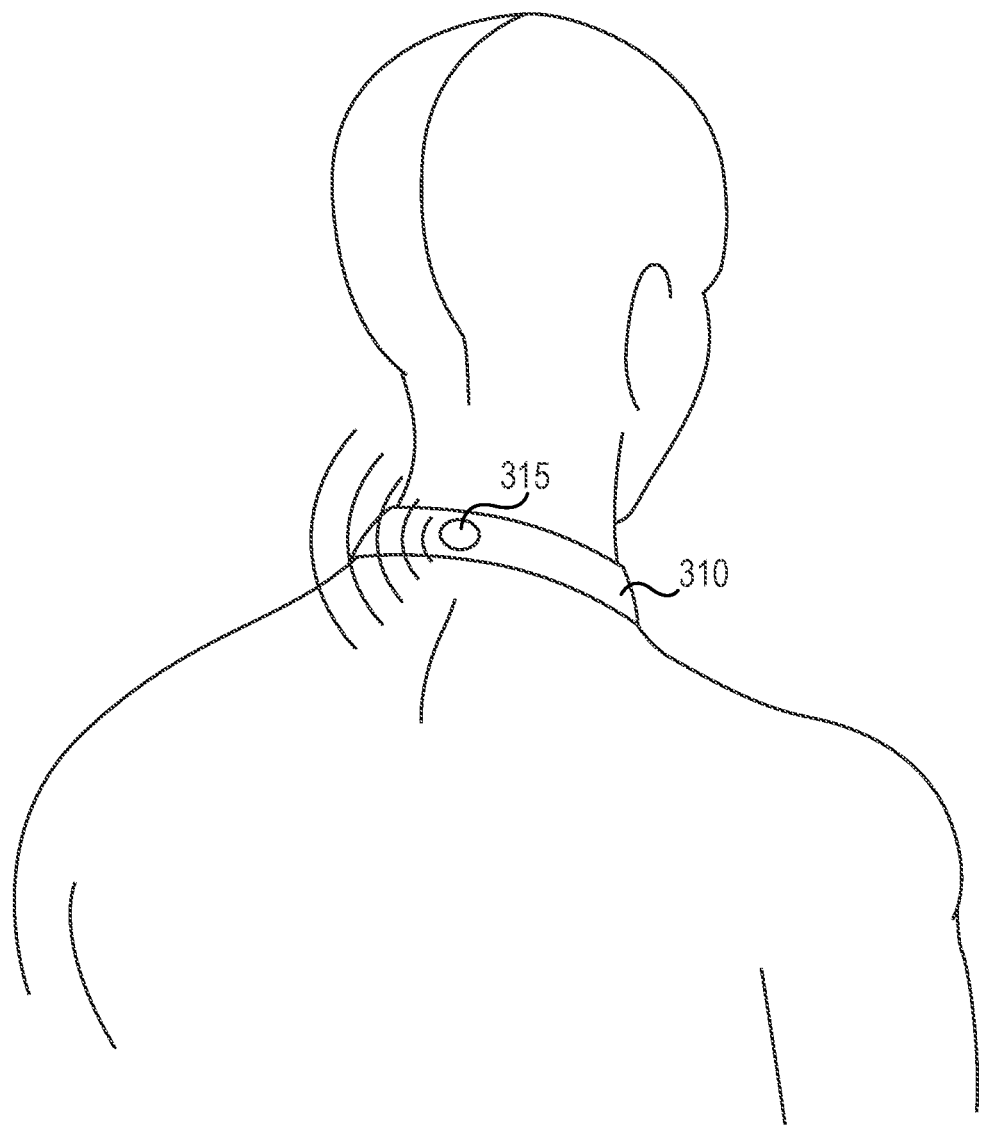
FIG. 25 is an exemplary diagram of a system with integrated electronics embodied in a collar device for reducing the effects of exposure to concussive events.

FIG. 25 is an exemplary diagram of a system with integrated electronics embodied in a collar device for reducing the effects of exposure to concussive events. In the embodiment shown in FIG. 25, the collar 310 can include one or more electronics 315. The electronics 315 can include at least one of the following: a camera, a light emitting diode (LED) light, a proximity sensor, a photo receptor, a fit check light, or a strobe light. The rear facing camera can warn runners or cyclists of traffic approaching from behind. The LED flash can be used to warn coaches when the wearer has sustained a high impact force through measurements of accelerometers. The LED can also be used to increase visibility of the wearer for cycling and running. The LED can also be used for indicating a touch in touch football. The electronics can also be used for determining a player's positioning or placement.

The electronics 315 an activity tracker, a gyroscope, an ambient light sensor, an optical heartbeat sensor, an altimeter, and an accelerometer. Other electronics can include a heart rate monitor, respiration monitor, oxygen level sensor, step counter, distance meter, global positioning sensor, and speedometer. The electronics can also include headphones or speakers. Other optional electronic can include a vibration metronome for training to a cadence. The electronics can also provide vibration alerts as a proximity alert, notify the wearer of incoming text messages, or provide an alarm or lap indicator. The electronics 315 can be used for team sports, road cycling, or running.

The electronics 315 can include a user interface module, a processing unit, a memory device, a communications device, an antenna, and an integrated power source. The integrated power source can include a battery (including rechargeable batteries), solar powered source, or a motion generated power source (electrical generator). The integrated power source can power all or selected electronics 315 incorporated into the collar device 310.

In some embodiments, the collar device 310 can improve or enhance aquatics sports such as diving, swimming, snorkeling, water polo, surfing, skiing, or any water related activity associated with impact with water surface or pressure associated with the depth of a wearer in a body of water. As such, the collar device and electronics can be sealed to prevent water intrusion into the electronics compartment.

The electronics can also be adapted for use by the military. Sensors can be incorporated to measure and report a wearer's biometrics. The electronics can also be used for communication. The electronics can be used as a blue force tracker or for location tracking of the wearer.

The electronics along with other incorporated features provide heat therapy, message, or cooling of the wears. In some embodiments, the collar can incorporate features for perspiration control. In other embodiments, the collar can provide skin transfer analgesics for pain management such as for migraine management.

Figure 26:
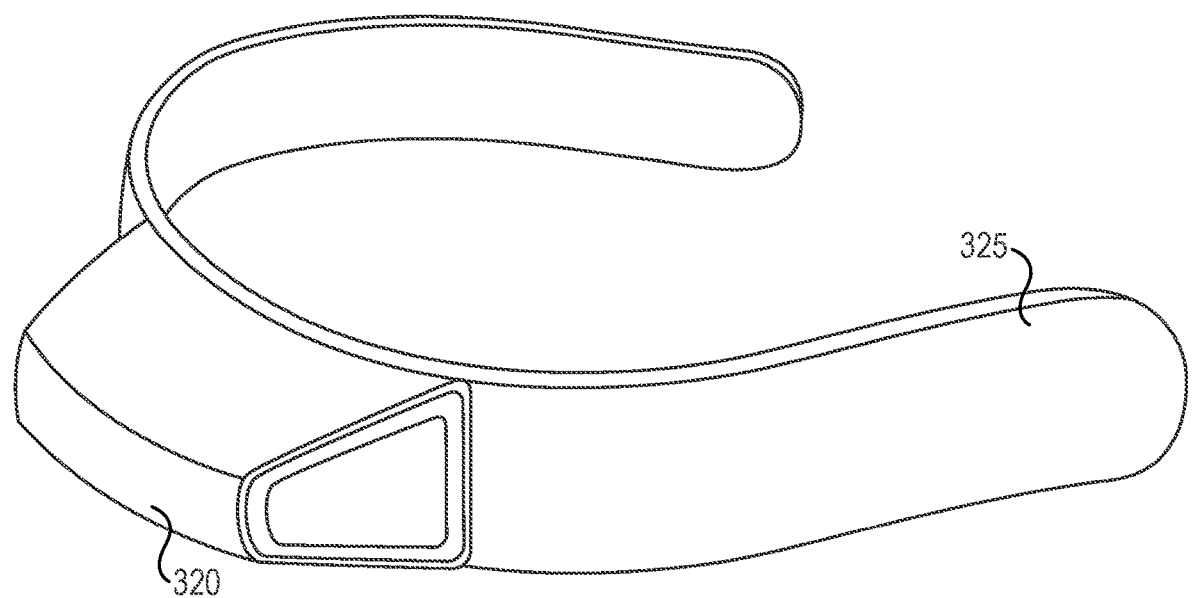
FIG. 26 is another exemplary diagram of a system with integrated electronics embodied in a collar device for reducing the effects of exposure to concussive events.

FIG. 26 is another exemplary diagram of a system with integrated electronics embodied in a collar device for reducing the effects of exposure to concussive events. The embodiment depicted in FIG. 26, provides a close up view of the integrated electronics compartment 320 which can be mounted on the collar 325. The compartment 320 can also house a power source for the integrated electronics.

Figure 27:
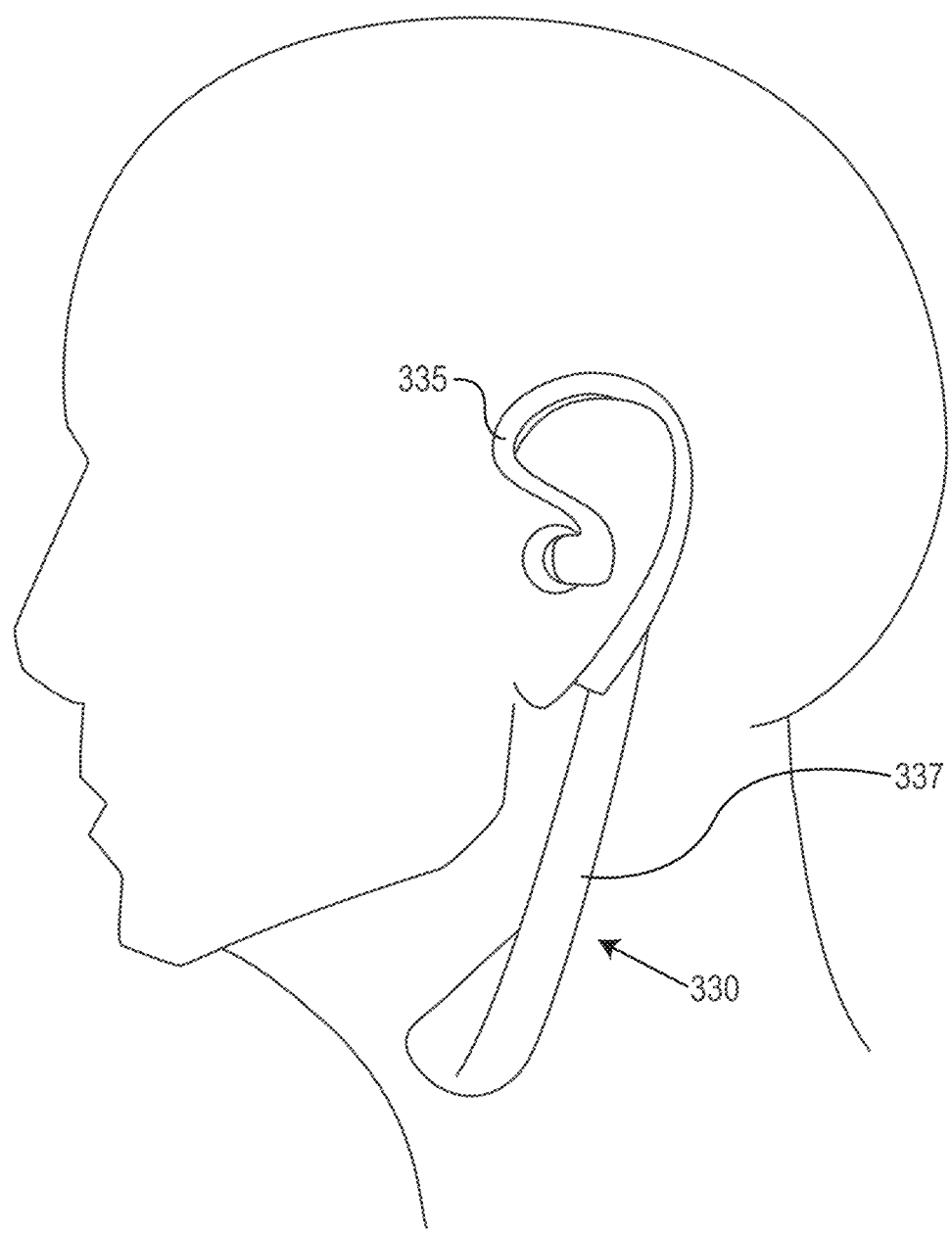
FIG. 27 is an exemplary diagram of a system incorporated into a sound system for reducing the effects of exposure to concussive events.

FIG. 27 is an exemplary diagram of a system incorporated into a sound system for reducing the effects of exposure to concussive events and/or damage to the inner ear caused by loud sounds (e.g., music) or blast waves. In the embodiment shown in FIG. 27, the device 330 can incorporate speakers 335 to communicate with the wearer. In some embodiments, the extensions 337 can incorporate microphones to allow two way communications utilizing the device 330.

Figure 28:
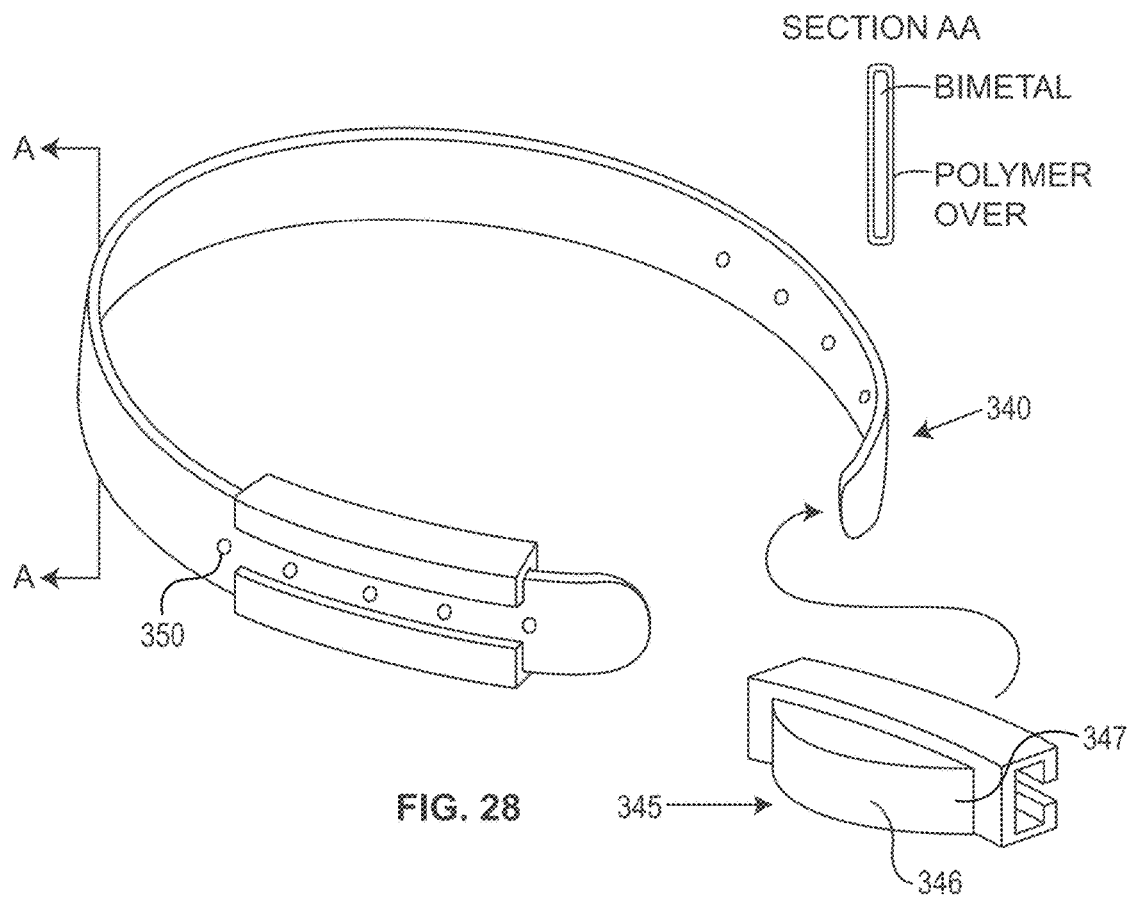
FIG. 28 is an exemplary diagram of an adjustable collar device for reducing the effects of exposure to concussive events.
Figure 29:
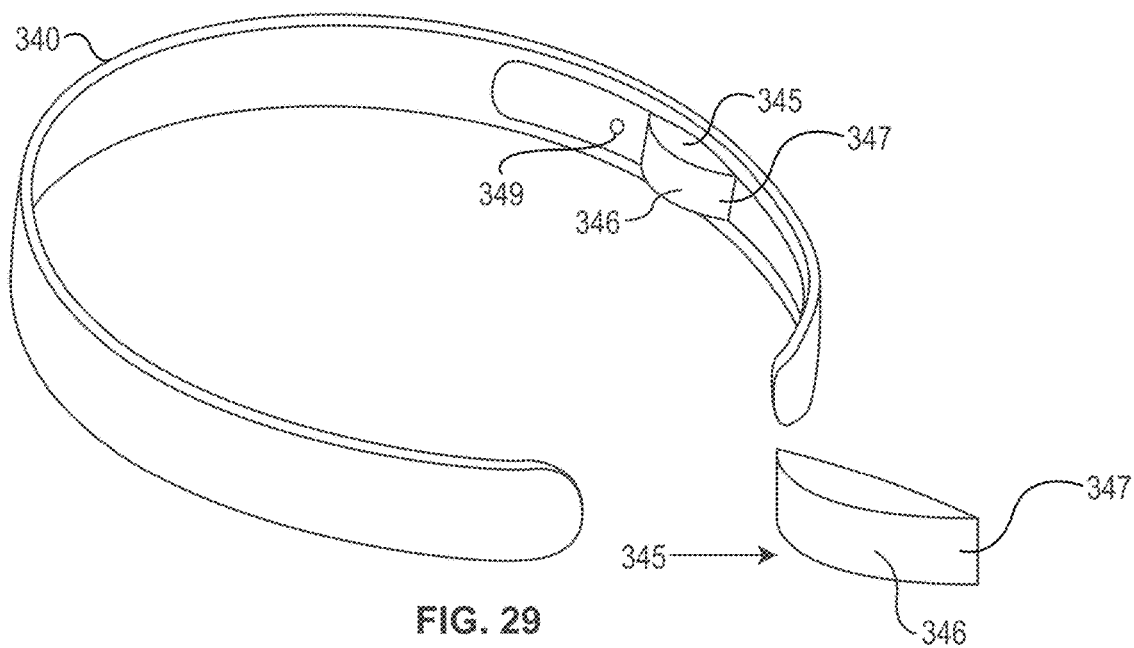
FIG. 29 is an exemplary diagram of an adjustable pressure pad integrated into a collar device for reducing the effects of exposure to concussive events.

FIGS. 28 and 29 refer to a collar 340. FIG. 28 is an exemplary diagram of an adjustable collar device for reducing the effects of exposure to concussive events. In the embodiment depicted in FIG. 28, the collar 340 can be constructed of any rigid or memory shape material (e.g, thermoplastic polymer, stainless steel, nickel-titanium (NiTi) alloy). In one embodiment, collar 340 comprises with a metal or bimetal center (e.g., a memory shape metal) covered with a polymer (e.g., a thermoplastic polymer) for comfort and to protect the inner core. One or more (e.g., two) pressure pad module(s) 345 comprising a protuberance can be slidably coupled with the collar 340. Optionally, the pressure pad module(s) 345 can be permanently affixed to, but remain slidably engaged with collar 340. Alternatively, the pressure pad module(s) 345 may be removably engaged with the collar e.g., to facilitate cleaning or replacement. The pressure pad module(s) 345 can be constructed from a soft, silicon type material. The pressure pad module(s) 345 may have a substantially uniform thickness on its body-facing surface such that it represents a thickening of the collar 340 in the region that overlies the neck veins. Alternatively, the pressure pad module(s) 345 may comprise an inwardly-directed protuberance 346 adapted to localize pressure on the target neck veins. Protuberance 346 may be a stud or other raised region that may be compressible or non-compressible. Optionally, the pressure pad module(s) 345 comprises a spring or spring-like device 347 underlying the protuberance 346 and adapted to exert an inward (in the direction of the body) pressure on the protuberance 346. When worn by the user, the spring is compressed to maintain protuberance 346 pressure on the target neck vein(s). Alternatively, protuberance 346 itself may be a spring e.g., consisting a smooth metal band with a convex bend in the body-facing direction. The position of the pressure pad module(s) 345 may be adjusted along the collar 340 through the use of positioning latching dents (not shown) on the pressure pad module(s) 345 that engage with notches or holes 350 on collar 340. It is understood that the detents and notches system illustrated in FIG. 28 may be replaced with any suitable reversible locking mechanism adapted to hold pressure pad module(s) 345 in place on collar 340. In one embodiment, the invention provides a system comprising a collar 340 and a plurality of pairs of pressure pad modules 345, wherein each pair of pressure pad modules 345 has differently-sized and/or differently-shaped protuberances relative to the other pairs. Such a system allows the subject to customize the collar fit and applied neck vein pressure.

FIG. 29 is an exemplary diagram of an adjustable/slidable pressure pad integrated into a collar device for reducing the effects of exposure to concussive events. The embodiment of FIG. 29 depicts one of the pressure pad modules 345 installed on the collar 340. In this embodiment, the pressure pad module is slidably engaged in a channel on the inner side of the collar 340 which optionally has a latching dent or similar mechanism 349 to hold the pressure pad module(s) 345 in the desired location. As shown, the collar 340 has inner and outer surfaces that are spaced opposite each other by a thickness and that extend along a length between two distal ends of the collar. The channel is defined through the inner surface only so that the channel is open only towards a center of the collar 340. The channel has a length longer than a width. A second one of the pressure pad modules 345 and channel are on an opposite side but obstructed in the perspective the view and thus not shown. Such a system allows the subject to adjust the positioning of the pressure pad module(s) 345 relative to the collar to ensure that the neck veins are adequately contacted.

Figure 30:
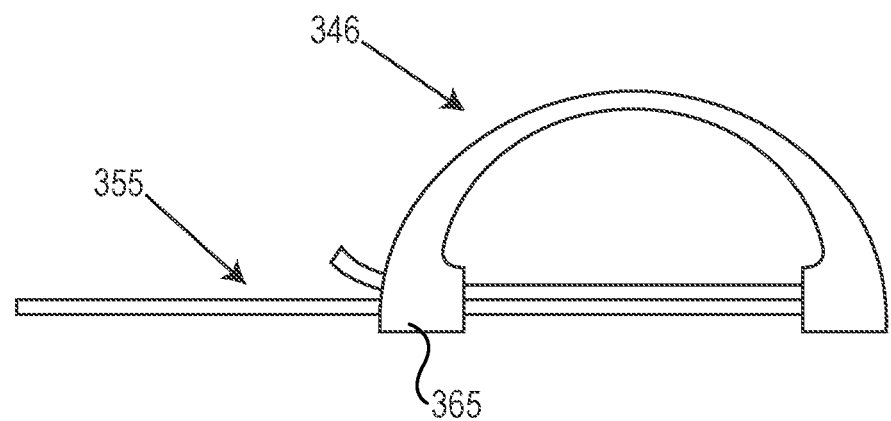
FIG. 30 is an exemplary diagram of an adjustable collar device in an unlatched position for reducing the effects of exposure to concussive events.
Figure 31:
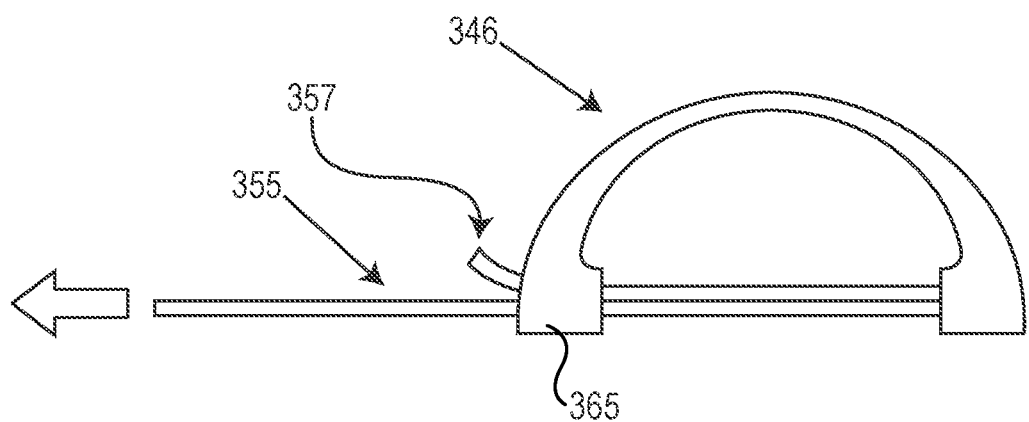
FIG. 31 is an exemplary diagram of an adjustable collar device in a latched position for reducing the effects of exposure to concussive events.

FIGS. 30 and 31 illustrate an adjustable protuberance 346 which may be used in combination with the pressure pad module(s) 345 illustrated in FIGS. 28-29, or any other embodiment of the inventions described herein. The adjustable protuberance 346 is a band formed from a flexible material such as plastic, nylon, or metal. One end of the band is permanently or reversibly fixed in place on strap 355. The other end of the band comprises opening 365 which is engaged with strap 355 in a slidable and reversibly lockable fashion. For example, opening 365 may contain a tab 357 that engages with notches in strap 355 similar to a ZIP TIE. As the band end comprising opening 365 is translocated in the direction of the fixed end, the loop defining the protuberance 346 increases in height. When applied to a collar device of the present invention, this protuberance 346 applies a greater neck vein pressure than the protuberance 346 in a more flattened configuration (i.e., having a greater distance between the fixed and slidable band ends).

Figure 32:
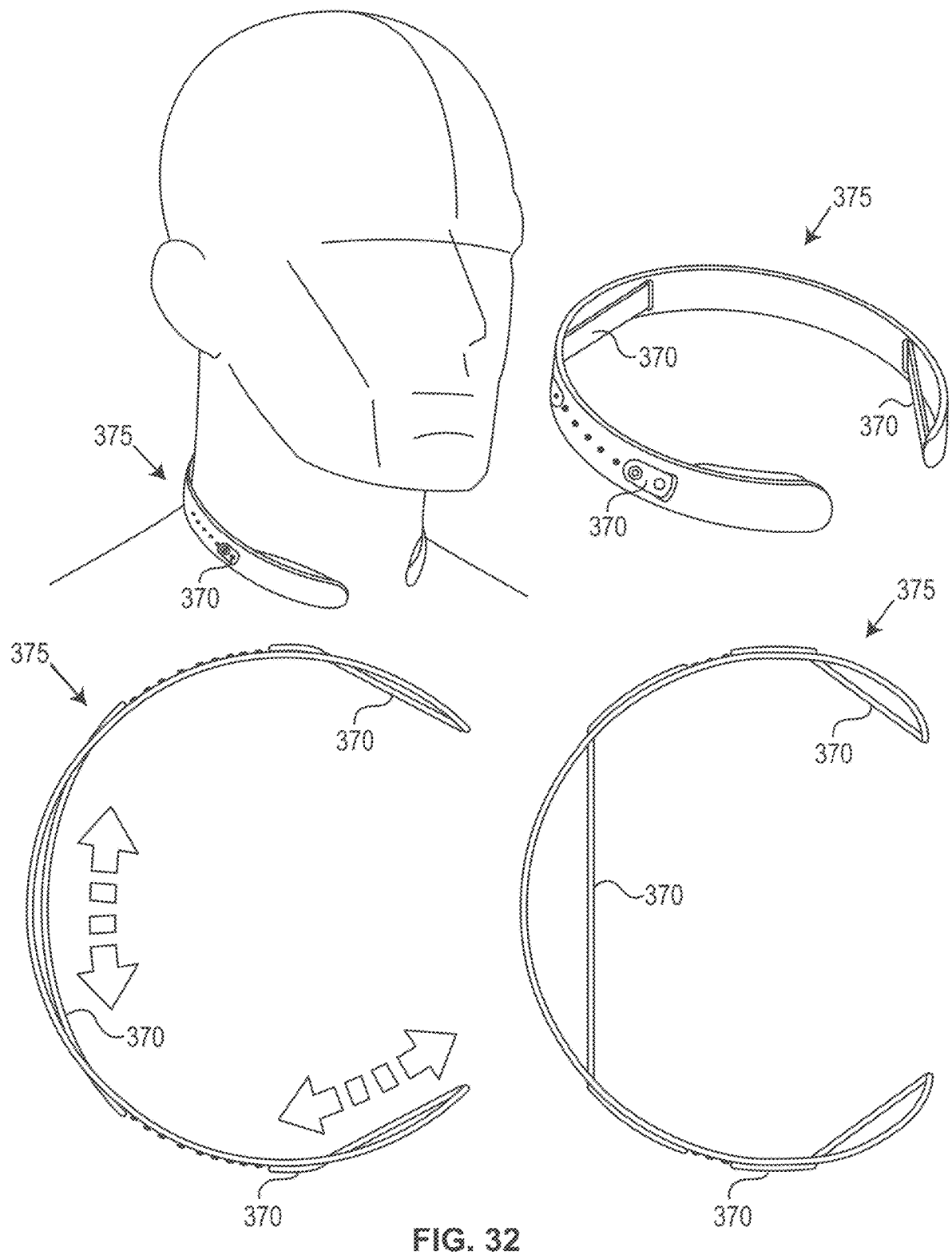
FIG. 32 is an exemplary top view of a diagram of an adjustable collar device for reducing the effects of exposure to concussive events.

FIG. 32 is an exemplary top view of a diagram of an adjustable collar device for reducing the effects of exposure to concussive events. In the embodiment depicted FIG. 32, a collar 375 can include a plurality of adjustment straps 370 to adjust the size of the collar 375 and/or increase or adjust the pressure points of the collar. The straps 370 can be pulled and released and held in desired position through the use of hook and loop, snap button detents, or other similar methods (not shown). The arrows shown in FIG. 32 depict how the straps 370 can be moved to adjust the size of the collar 375 and/or increase or adjust the pressure points of the collar. In the embodiment depicted in FIG. 32, the straps 370 provides pressure on the veins in the neck of the wearer.

Figure 33:
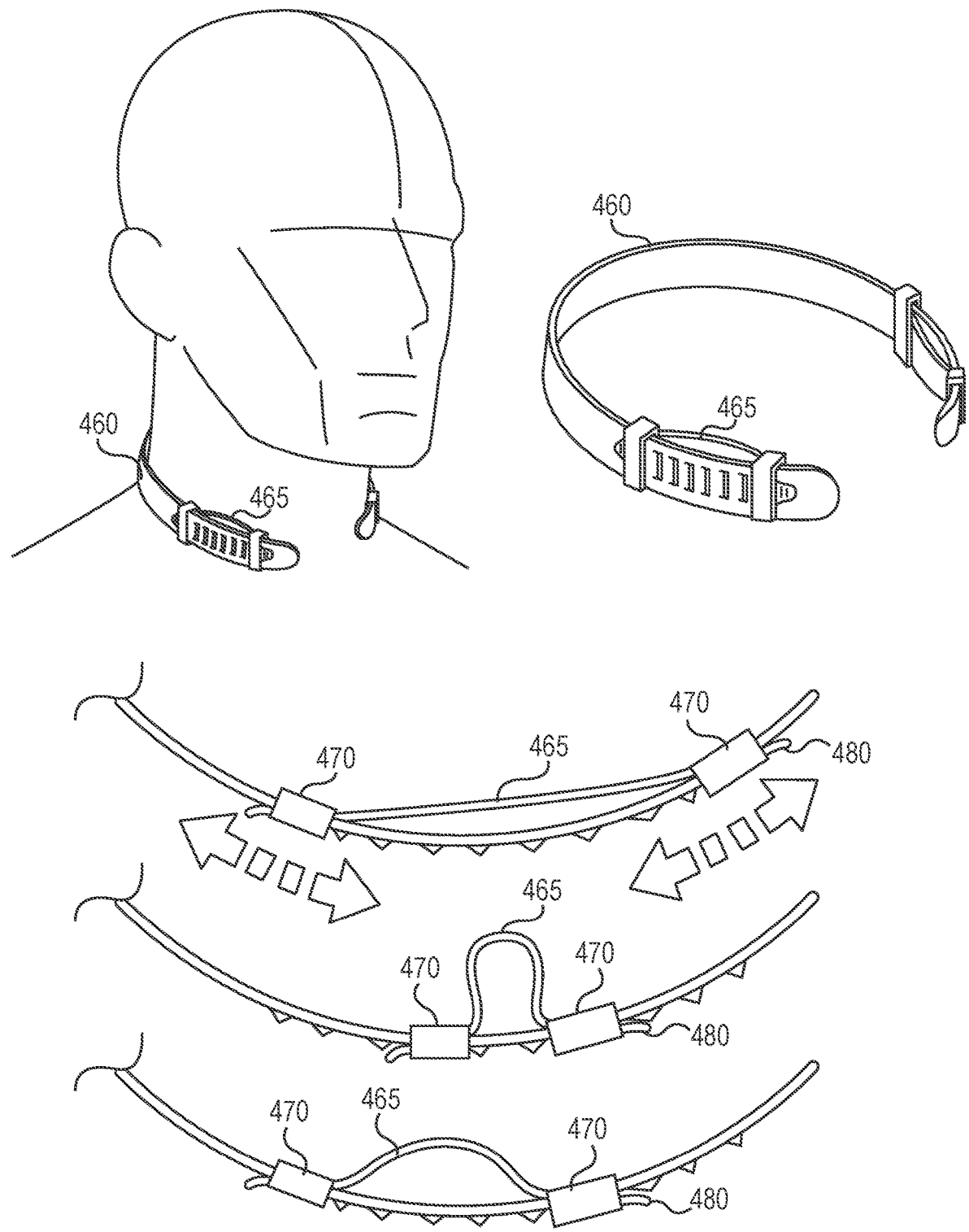
FIG. 33 is an exemplary diagram of an adjustable collar device for reducing the effects of exposure to concussive events.

FIG. 33 is an exemplary diagram of another system for producing adjustable protuberances 465 on a collar 460. In this embodiment, the protuberances 465 are formed from a flexible material, as described elsewhere herein (see, for example, FIGS. 30-31). The protuberance 465 is engaged directly with collar 460 via an engagement member 470 at each end. Optionally, one engagement member 470 is fixed to collar 460 and the other engagement member 470 is slidably attached. Alternatively, both engagement members 470 are slidably attached to collar 460. The slidable attachments of engagement members 470 reversibly hold the engagement members in place on collar 460. The engagement members 470 may comprise detents or tabs 480 that engage with notches or holes on collar 460. It is understood that any suitable reversibly locking mechanism or system may be used. In use, the protuberance 465 height is increased, in the body-facing direction, as the linear distance along collar 460 between the engagement members 470 is reduced, thereby applying more pressure to the target neck veins.

Figure 34:
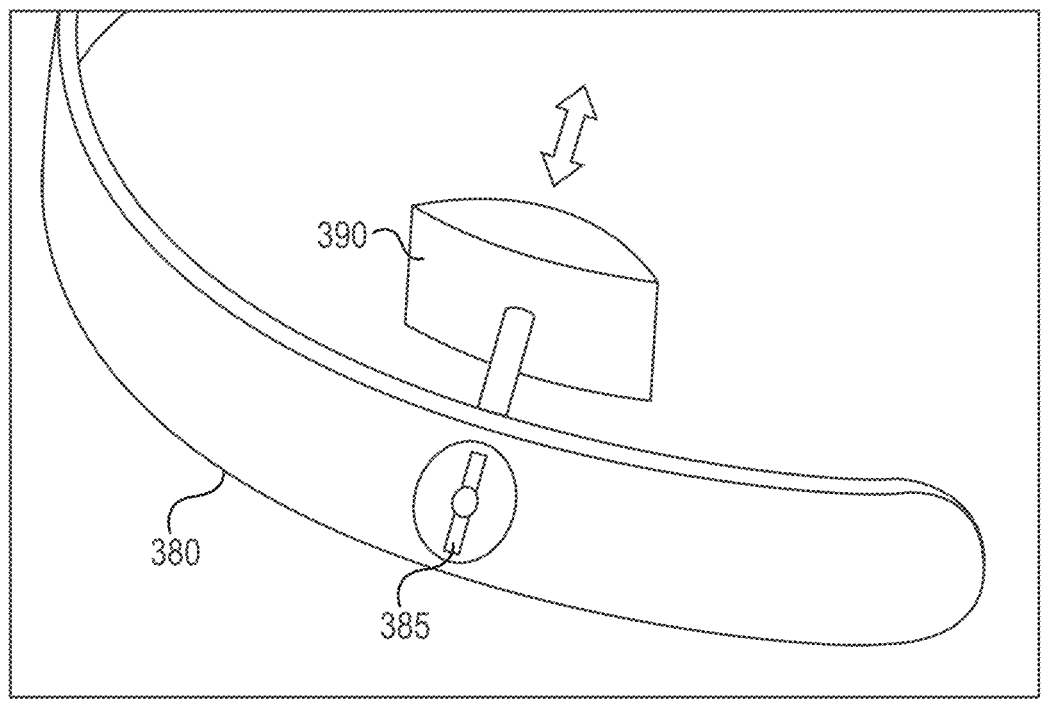
FIG. 34 is an exemplary diagram of a dial force adjustment mechanism for reducing the effects of exposure to concussive events.

FIG. 34 is an exemplary diagram of a dial force adjustment mechanism for reducing the effects of exposure to concussive events. In the collar 380 shown in FIG. 34, a force selector dial 385 can be used to adjust the force on the pressure pads 390. In one embodiment, turning the dial 385 moves an internal piston (not shown) against a spring to extend the pressure pads 390 in the body-facing direction. Turning the dial 385 in the opposite direction would reduce the tension. Alternatively, the pressure pads 390 may be mounted on a mechanical screw such that a turning of the dial 385 rotates the screw thereby moving the pressure pad 390 either towards or away from the neck.

Figure 35:
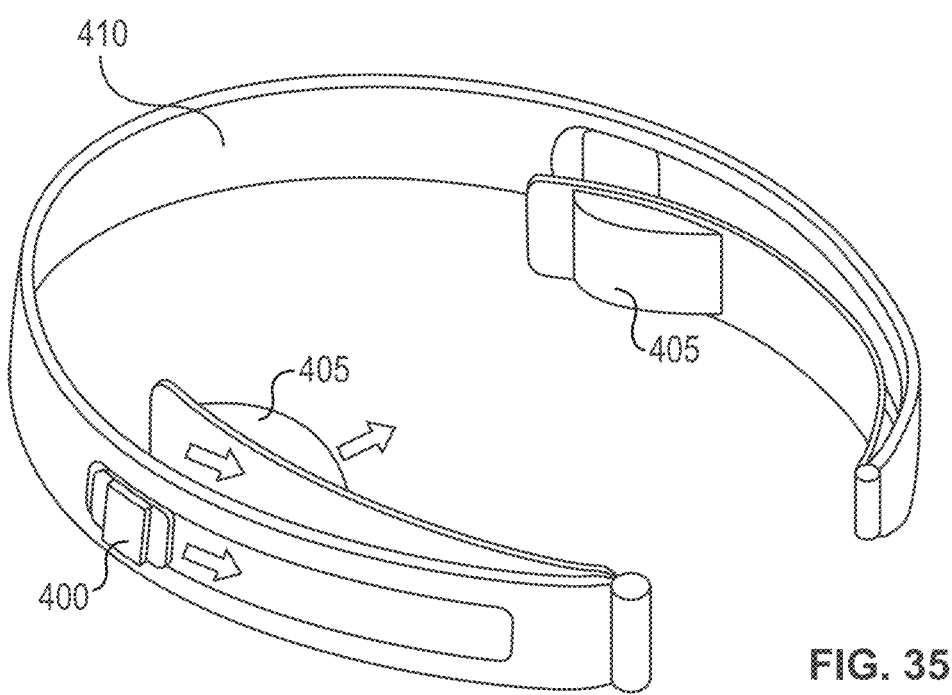
FIG. 35 is an exemplary diagram of a slider force adjustment mechanism for reducing the effects of exposure to concussive events.

FIG. 35 is an exemplary diagram of a slider force adjustment mechanism for reducing the effects of exposure to concussive events. In the collar shown in FIG. 35, a force selector slider 400 can be used to increase the pressure on the pressure pads 405. Moving the slider 400 in one direction will move the pressure pads 405 inward towards the center of the collar 410 increasing the pressure on the pads 405. Moving the slider 400 in an opposite direction will move the pressure pads 405 outward away from the center of the collar 410 reducing the pressure on the pads 405.

Figure 36:
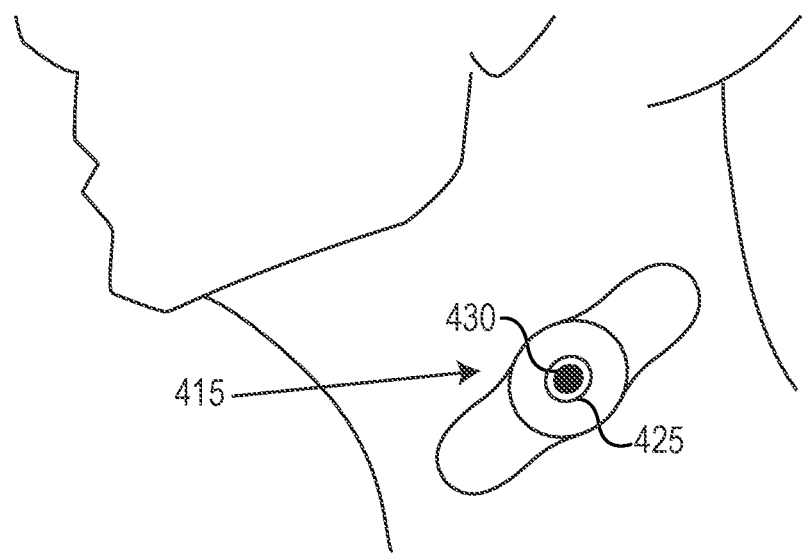
FIG. 36 is an exemplary diagram of a side view of a system embodied a pressure sensitive strip for reducing the effects of exposure to concussive events.

FIG. 36 is an exemplary diagram of a side view of a system embodied a strip (non-collar device) comprising an adhesive on the body-facing surface and having a protuberance mounted on a reversible extension mechanism for reducing the effects of exposure to concussive events. In the embodiment depicted in FIG. 36, the strip 415 can be placed over the veins of the neck. When protection (i.e., neck vein pressure) is desired, the button 425 of the strip 415 is engaged which pushes an embedded protuberance against the neck veins. When protection is no longer necessary, the button 425 can be depressed again, thereby disengaging the pressure on the veins in the neck. In some embodiments, the button, 425 can have a colored band 430 to easily verify visually if the device is engaged or disengaged.

Figure 37:
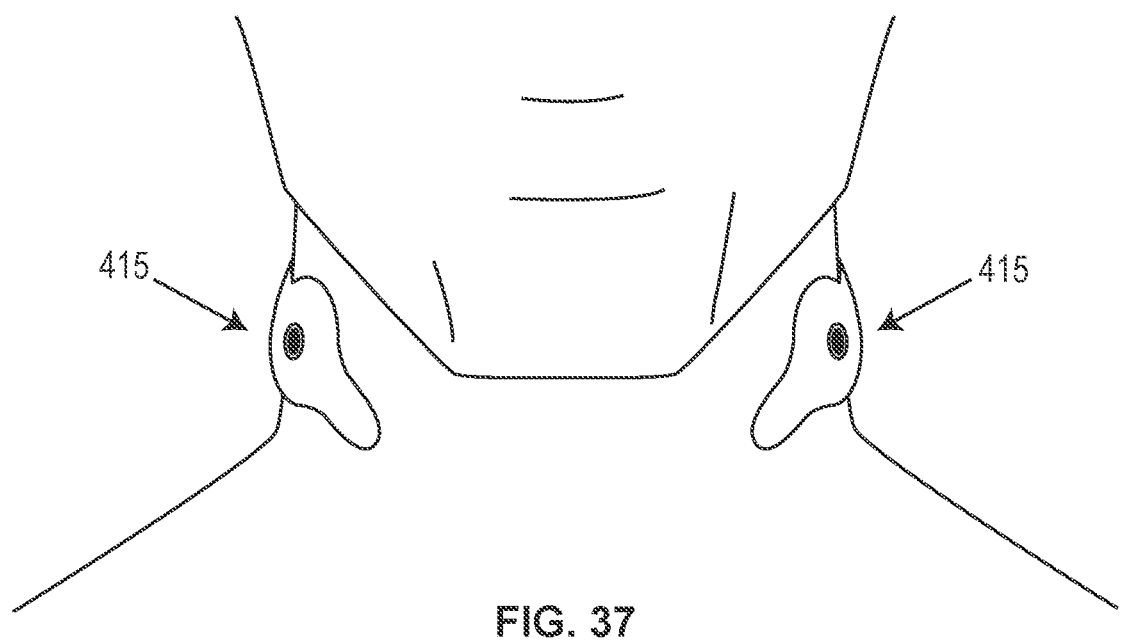
FIG. 37 is an exemplary diagram of a front view of a system embodied a pressure sensitive strip for reducing the effects of exposure to concussive events.

FIG. 37 is an exemplary diagram of a front view of a system embodied a strip for reducing the effects of exposure to concussive events. FIG. 37 depicts a pair of strips 415 positioned on the neck of a wearer. The strips 415 can be positioned over the veins of a wearer and the push-button 425 can engage the protuberances when concussive events are likely. For example, in a football game, the player can wear the strips 415 and just prior to entering the field, the push-buttons 425 can be engaged thereby increasing the pressure in the veins of the neck of the wearer.

Figure 38:
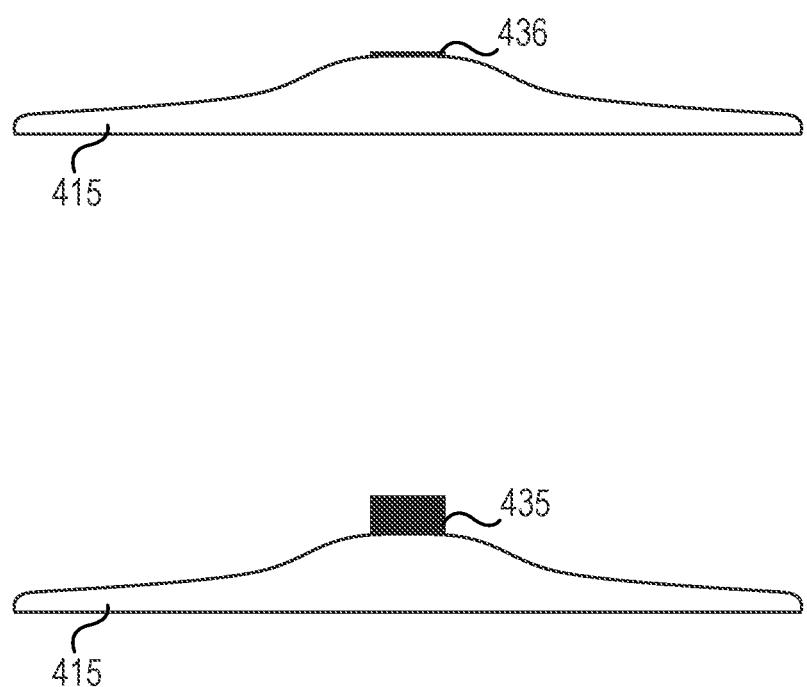
FIG. 38 is an exemplary diagram of a system embodied a pressure sensitive strip for reducing the effects of exposure to concussive events.

FIG. 38 illustrates profile views of the strip 415. FIG. 38 depicts the protuberance in the deployed position 435 and the protuberance in the retracted position 436. The protuberance can be spring-loaded with a push-button type release used to extend and retract the protuberance as desired.

Figure 39:
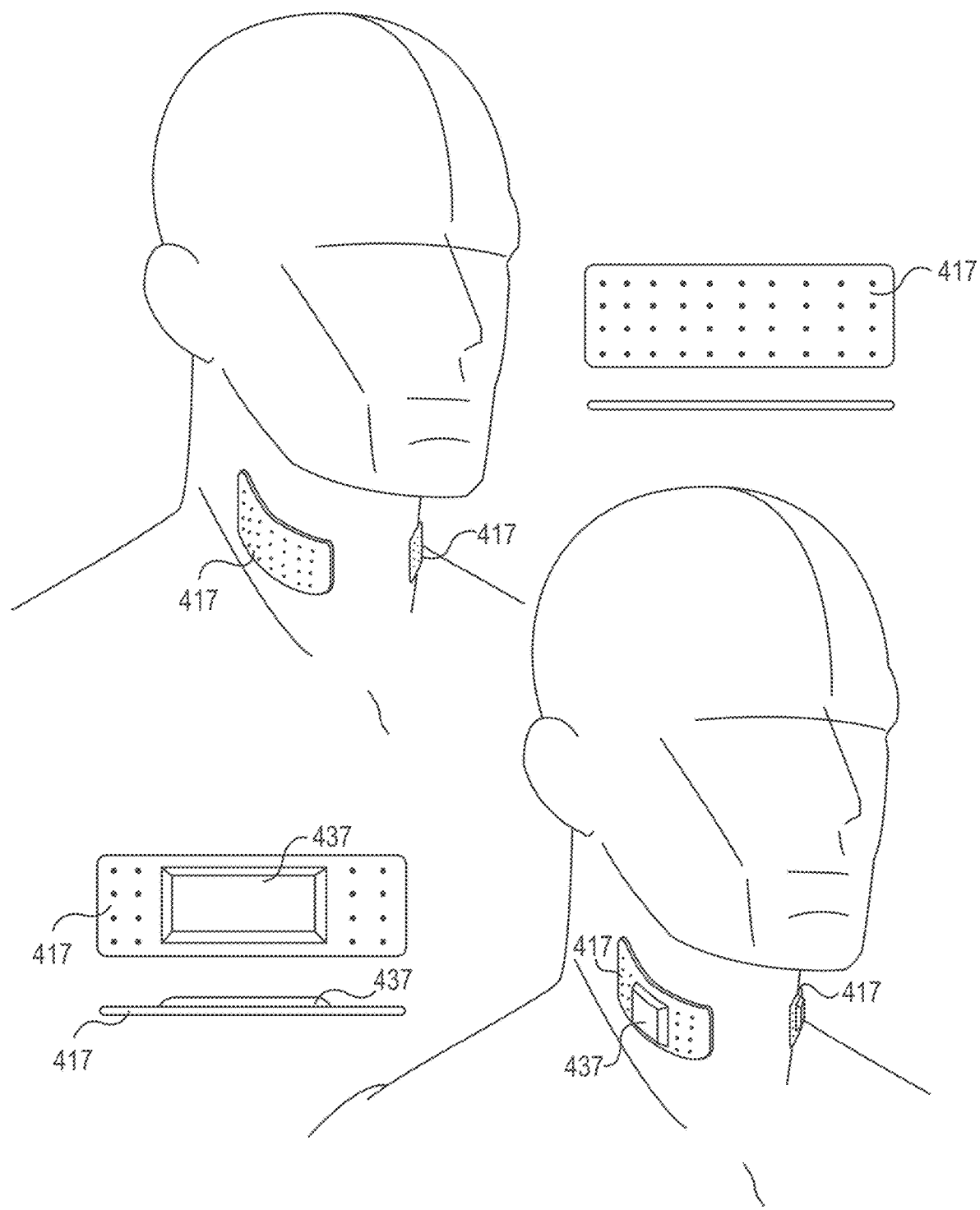
FIG. 39 is an exemplary diagram of a system embodied in a self-stick flexible pad for reducing the effects of exposure to concussive events.

FIG. 39 illustrates a flexible pad 417 having an adhesive on the body-facing surface. The pads 417 can be positioned over the veins in the neck of the wearer. Adhesive can be pre-applied to one side of the pad 417 to hold the pad in position over the veins in the neck of the wearer. Placement of the flexible pad 417 on the skin can pull the skin tight, thereby increasing the pressure on the veins of the neck of the user. Further, a rigid section 437 can be added to the pad 417 to further increase the pressure on the neck of the user. The pads 417 can be positioned on the neck when increased protection is desired and removed when the activity requiring protection from concussive events are completed.

Figure 40:
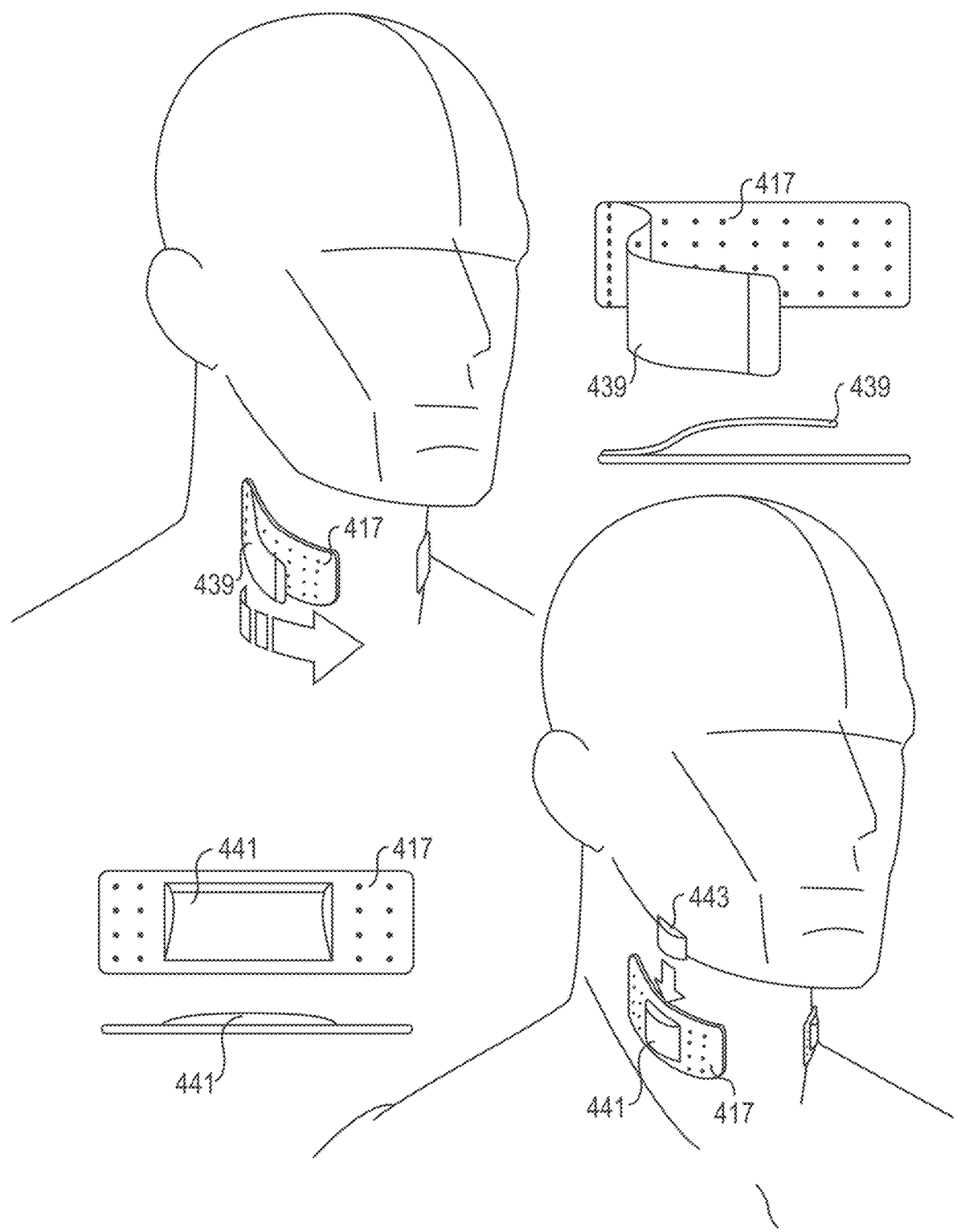
FIG. 40 is an exemplary diagram of another system embodied in a self-stick flexible pad for reducing the effects of exposure to concussive events.

FIG. 40 illustrates another embodiment of the self-stick flexible pad 417. The pads 417 can be positioned over the veins in the neck of the wearer. Adhesive can be pre-applied to one side of the pad 417 to hold the pad in position over the veins in the neck of the wearer. The embodiment illustrated in FIG. 40 incorporates an adjustable layer 439 for adjusting placement of the flexible pad over the neck of the wearer. Another embodiment of the flexible pad 417 with a flat pocket 441 integrated into the flexible pad 417 is illustrated in FIG. 40. Removable inserts 443 can be placed into the flat pocket 441 to increase the pressure on the veins in the neck of the wearer. The removable inserts 443 can be manufactured with a plurality of different sizes to adjust the pressure on the veins of the neck of the wearer.

Figure 41:
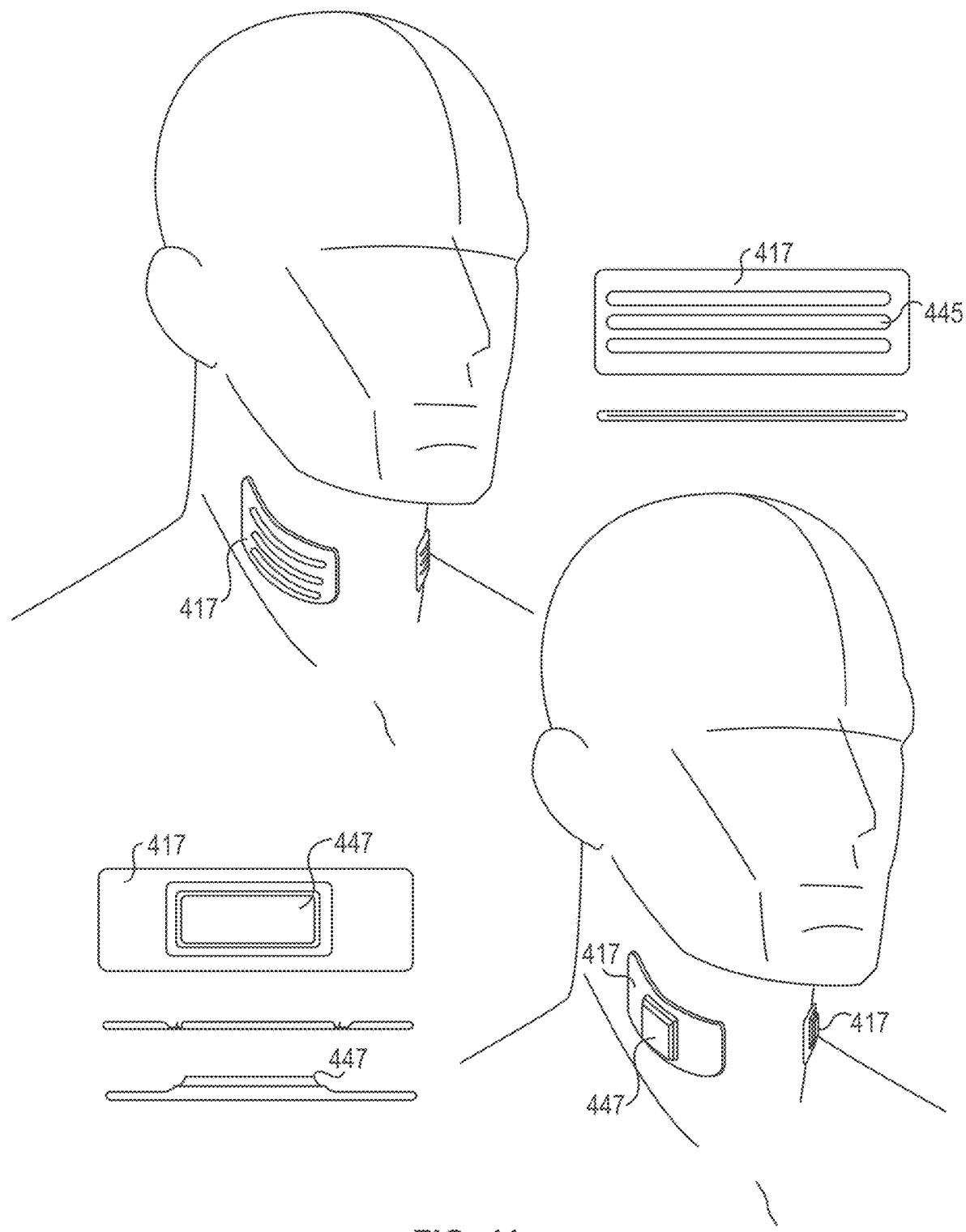
FIG. 41 is an exemplary diagram of another system embodied in a self-stick flexible pad for reducing the effects of exposure to concussive events.

FIG. 41 illustrates another embodiment of the self-stick flexible pad 417, incorporating stiffening strips 445. The stiffening strips 445 can be comprised of a flexible material (such as a memory metal) that can be depressed to increase the pressure on the veins of the neck of the wearer. The pads 417 can be positioned on the neck when increased protection is desired and removed when the activity requiring protection from concussive events are completed.

FIG. 41 also illustrates another embodiment of the self-stick flexible pad 417 incorporating a fit check indicator 447. When the flexible pad 417 is properly positioned, the fit check indicator 447 provides visual confirmation that the pad 417 is in position and engaged. In some embodiments the visual confirmation can be achieved by having an indicator button pop out when the pad 417 is properly positioned.

Figure 42:
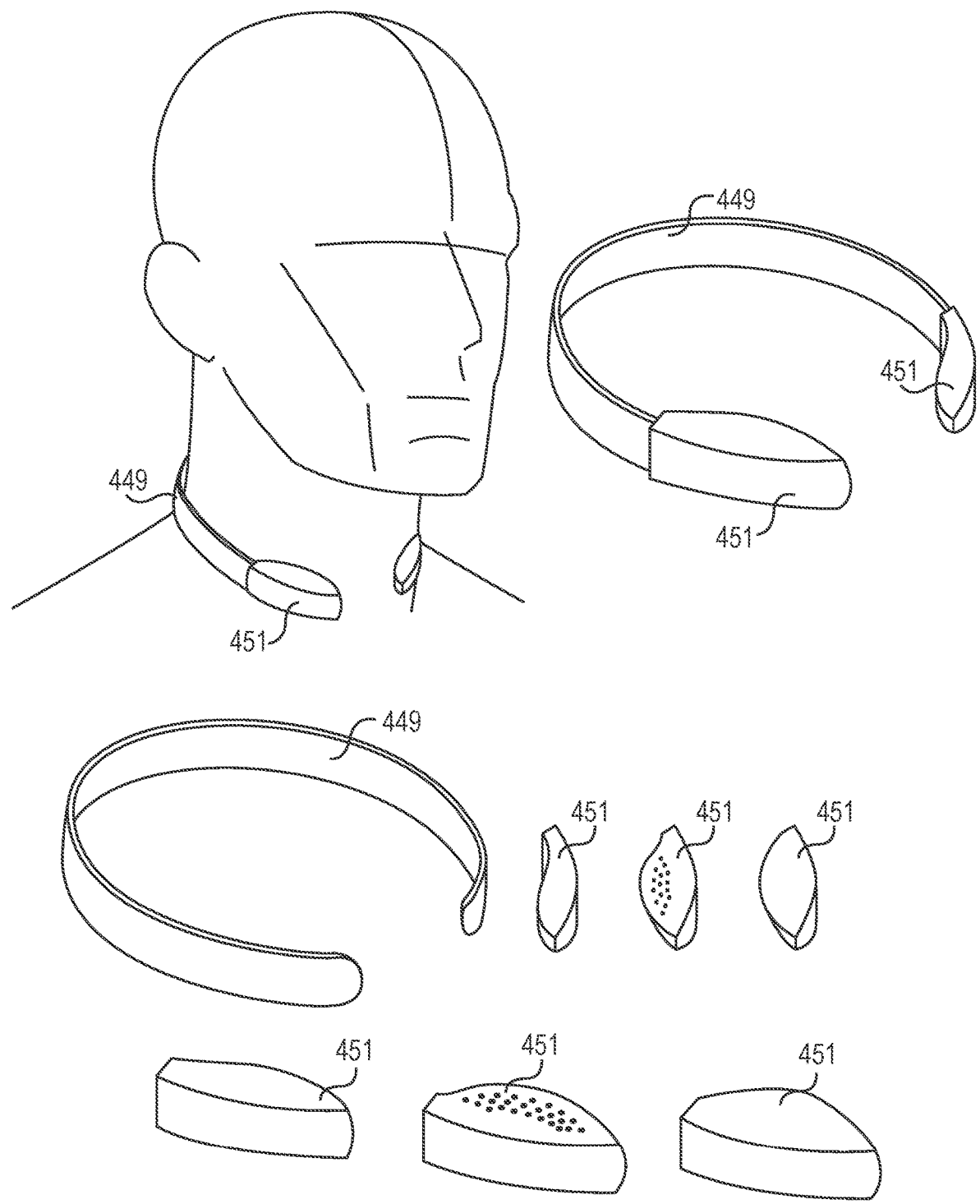
FIG. 42 is an exemplary diagram of a collar device with removable tips for reducing the effects of exposure to concussive events.

FIG. 42 illustrates an embodiment of the collar device 449 with removable tips 451 for adjustable size and comfort. The collar device 449 illustrated in FIG. 42 is an open collar configuration that encircles the neck of the wearer. The tips 451 can be coupled with the proximal and distal ends of the collar device 449. The tips 451 can be manufactured in different sizes and constructed with different materials. The pressure on the veins of the neck of the wearer can be adjusted by changing the size of the tips 451 coupled to the collar device 449.

Figure 43:
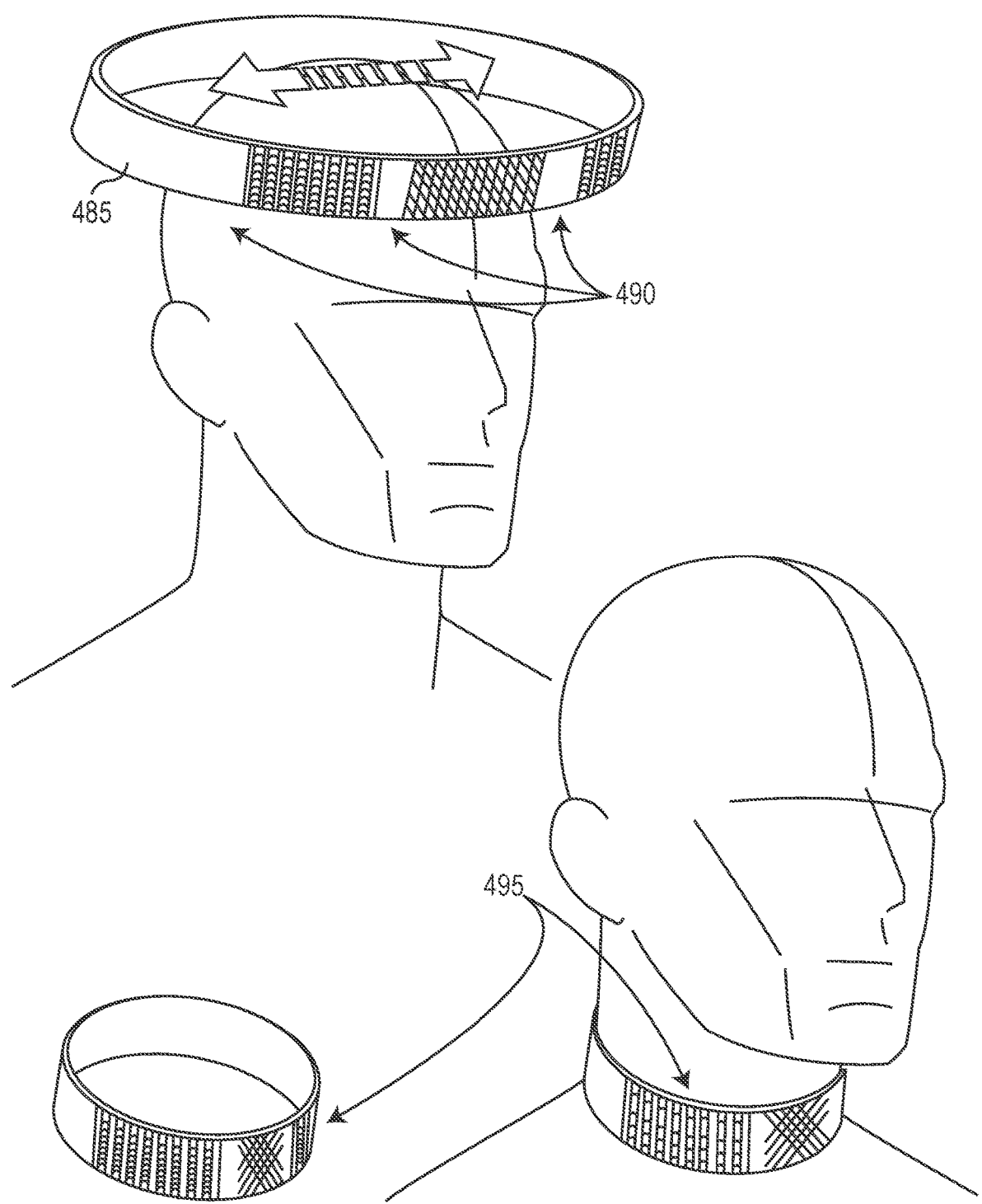
FIG. 43 is a detailed view of a system incorporating an adjustable closed collar for reducing the effects of exposure to concussive events.

FIG. 43 is a detailed view of a system incorporating an adjustable closed collar for reducing the effects of exposure to concussive events. In the embodiment depicted in FIG. 43, the collar 485 can be constructed of a seamless textile fabric with expandable elastic zones 490. The collar 485 can also include stiff non-expanding zones 495. In some embodiments, the non-expanding zones 495 can include protuberances (not shown) for applying pressure on the veins of the wearer's neck. The collar 485 can apply pressure on the area above the veins of the wearer's neck while still remaining comfortable.

Figure 44:
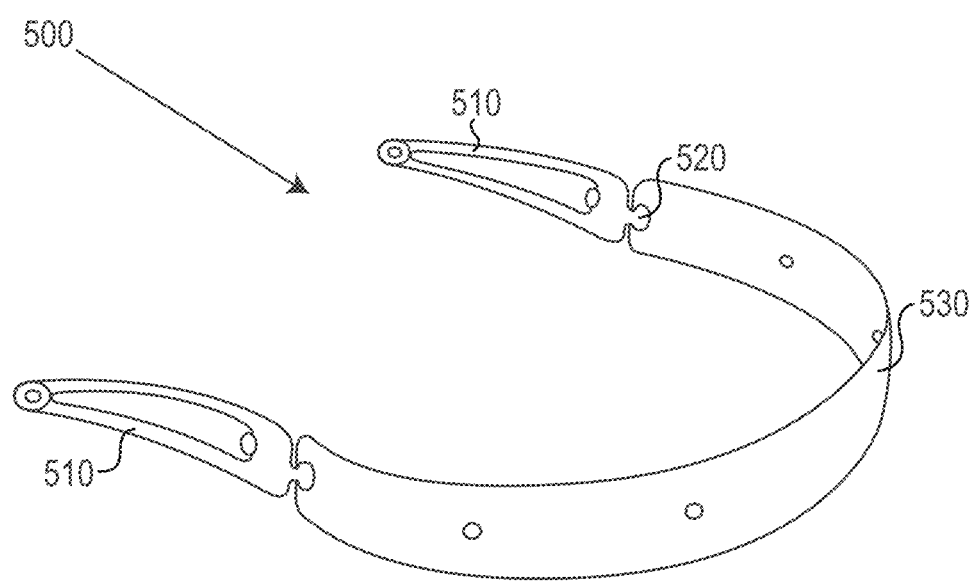
FIG. 44 is a detailed view of a system incorporating a latching mechanism for reducing the effects of exposure to concussive events.

FIG. 44 illustrates the central core 530 of a partially circumferential collar 500. The core 500 is made of a resilient material with spring-like properties (e.g., plastic or memory metal). An arm 510 is attached to each end of the core 530 by a hinge 520. When incorporated into a partially circumferential collar 500, the protuberances (not shown) are positioned on the arms 510. The hinge 520 is adapted to have a closed and an open configuration. In the closed configuration, the hinge 520 is locked such that the arms 510, and therefore the protuberances (not shown), are positioned against the veins in the neck of the wearer. In the open position, the arms 510 swing away from the subject's neck, thereby relieving the pressure of the neck veins. This configuration is advantageous for devices that are intended for intermittent use, such as in sporting equipment. Neck vein pressure may be applied or relieved without the need to don and remove the collar 500. This is particularly useful when incorporated into the embodiments in which the collar 500 or other pressure-applying device is attached to an anchor point that is not intended to be intermittently removed as frequently as the neck vein pressure (e.g., a piece of protective equipment such as shoulder pads). This system is also useful when incorporated into the various headgear embodiments described herein (e.g., helmets, headbands, headphones, etc.) because the protuberances can be positioned away from the neck when the headgear is donned or removed, thereby increasing the convenience and lessening the likelihood of damage to the protuberances and associated structures.

Figure 45:
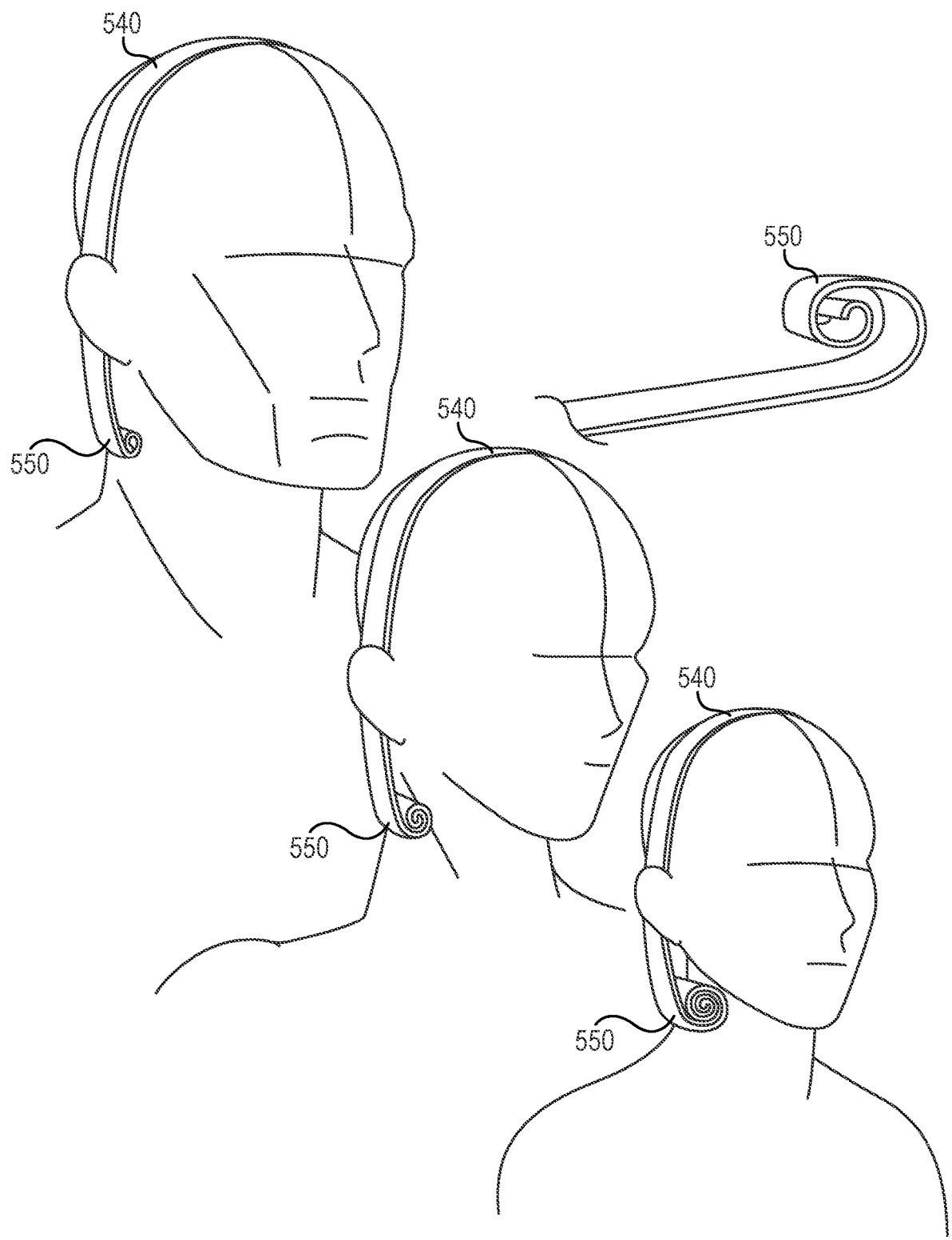
FIG. 45 is an exemplary adjustable strap for reducing the effects of exposure to concussive events.

FIG. 45 illustrates an adjustable strap for reducing the effects of exposure to concussive events. In the embodiment illustrated in FIG. 45, a strap 540 can roll up at the proximal and distal end regions of the strap 540. The proximal and distal end regions can be capable of maintaining the roll 550. The roll 550 places pressure on the veins of the neck of the wearer when positioned on the head of the user. The strap can be constructed of various materials to enable to end regions to adjust and maintain the newly configured shape. The end regions may be unrolled to adjust the size of the device thereby allowing one size to fil all by rolling or unrolling the proximal and distal end regions as necessary for the required length of the strap 540 to achieve the proper fit.

Figure 46:
FIG. 46 is an exemplary flexible neck wrap for reducing the effects of exposure to concussive events.

FIG. 46 illustrates a flexible neck wrap 560 for reducing the effects of exposure to concussive events. In the embodiment illustrated in FIG. 46, the neck wrap 560 can be wrapped around the neck of the wearer to increase pressure on the veins in the neck. In some embodiments, the flexible neck wrap 560 can incorporate protuberances (not shown) to further increase pressure in the veins of the neck. In other embodiments, the flexible neck wrap can include rigid regions to increase pressure on the veins of the neck when worn.

The disclosed embodiments are susceptible to various modifications and alternative forms, and specific examples thereof have been shown by way of example in the drawings and herein described in detail. It should be understood, however, that the disclosed embodiments are not meant to be limited to the particular forms or methods disclosed, but to the contrary, the disclosed embodiments are to cover all modifications, equivalents, and alternatives.

What is claimed is:

1. A system comprising:
a collar device having a body extending along a length between two distal ends so that the body is partially circumferential, the body having an inner and an outer surface opposite each other and spaced apart by a thickness,
wherein the collar device is sized to be worn around a human neck with the two distal ends defining an opening of the body therebetween that is positionable at a laryngeal prominence of the human neck when the collar device is worn;
a pair of channels disposed at opposite ends of the body, wherein each channel has a length that extends along a portion of the length of the body
wherein the length of each channel is longer than a width of each channel, and
wherein each channel has a depth through only the inner surface of the body and the depth is less than the thickness of the body so that each channel is open only towards a center of the collar;
a first pair of inward facing pressure pad modules,
wherein each pressure pad module of the first pair engaged in the respective channel and slidable along the length of the respective channel to position and align each pressure pad module of the first pair to a vein of a user's neck so that a pressure is applied to the vein when the collar device is worn.

2. The system of claim 1, wherein each pressure pad module comprises an inwardly-facing protuberance.

3. The system of claim 2, wherein the inwardly-facing protuberance has a shape that is adjustable.

4. The system of claim 2, wherein the inwardly-facing protuberance comprises a spring or resilient compressible material.

5. The system of claim 2, wherein the inwardly-facing protuberance comprises a band with a convex bend in the body-facing direction.

6. The system of claim 1, wherein the system is configured so that the vein to which each pressure pad module of the first pair is positionable and alignable when worn is an internal jugular vein, external jugular vein, or both.

7. The system of claim 1, wherein the collar device is adapted to apply an inward pressure on each vein of 10-80 mm Hg.

8. The system of claim 1, wherein the body is semi-rigid or rigid.

9. The system of claim 1, wherein the first pair of pressure pad modules is removably engaged with the collar.

10. The system of claim 9, further comprising a second pair of pressure pad modules that, upon removal of the first pair of pressure pad modules, are removably engageable with the collar.

11. The system of claim 1, wherein the collar device comprises a memory shape material.

12. The system of claim 1, wherein the system comprises two or more pairs of pressure pad modules.

13. The system of claim 1, wherein each pressure pad module of the first pair is held at a desired location along the length of the collar by a fastener.

* * * * *